US008937063B2

(12) United States Patent
Bachovchin et al.

(10) Patent No.: US 8,937,063 B2
(45) Date of Patent: Jan. 20, 2015

(54) NIACIN MIMETICS, AND METHODS OF USE THEREOF

(75) Inventors: William W. Bachovchin, Cambridge, MA (US); Hung-sen Lai, Andover, MA (US); Daniel P. O'Connell, Boston, MA (US); Wengen Wu, Medford, MA (US); Christopher P. Kiritsy, Waban, MA (US)

(73) Assignees: Trustees of Tufts College, Boston, MA (US); Arisaph Pharmaceuticals, Inc., Boston, MA (US)

( * ) Notice: Subject to any disclaimer, the term of this patent is extended or adjusted under 35 U.S.C. 154(b) by 349 days.

(21) Appl. No.: 13/168,629

(22) Filed: Jun. 24, 2011

(65) Prior Publication Data

US 2012/0077808 A1 Mar. 29, 2012

Related U.S. Application Data

(60) Provisional application No. 61/358,245, filed on Jun. 24, 2010.

(51) Int. Cl.
| | | |
|---|---|---|
| *A61K 31/167* | (2006.01) | |
| *A61K 31/192* | (2006.01) | |
| *C07D 213/80* | (2006.01) | |
| *A61K 31/455* | (2006.01) | |
| *A61K 31/22* | (2006.01) | |
| *A61K 31/366* | (2006.01) | |
| *A61K 31/397* | (2006.01) | |
| *A61K 31/40* | (2006.01) | |
| *A61K 31/404* | (2006.01) | |
| *A61K 31/44* | (2006.01) | |
| *A61K 31/47* | (2006.01) | |
| *A61K 31/505* | (2006.01) | |
| *A61K 31/5377* | (2006.01) | |
| *A61K 31/616* | (2006.01) | |
| *A61K 45/06* | (2006.01) | |

(52) U.S. Cl.
CPC ............ *A61K 31/455* (2013.01); *A61K 31/167* (2013.01); *A61K 31/192* (2013.01); *A61K 31/22* (2013.01); *A61K 31/366* (2013.01); *A61K 31/397* (2013.01); *A61K 31/40* (2013.01); *A61K 31/404* (2013.01); *A61K 31/44* (2013.01); *A61K 31/47* (2013.01); *A61K 31/505* (2013.01); *A61K 31/5377* (2013.01); *A61K 31/616* (2013.01); *A61K 45/06* (2013.01); *C07D 213/80* (2013.01)
USPC .................... 514/232.2; 514/235.5; 544/131; 544/82

(58) Field of Classification Search
None
See application file for complete search history.

(56) References Cited

U.S. PATENT DOCUMENTS

| | | |
|---|---|---|
| 3,420,788 A | 1/1969 | Solms |
| 3,426,011 A | 2/1969 | Parmerter |
| 3,453,257 A | 7/1969 | Parmerter |
| 3,453,259 A | 7/1969 | Parmerter |
| 3,459,731 A | 8/1969 | Gramera et al. |
| 4,021,436 A | 5/1977 | Cavazza |
| 4,235,871 A | 11/1980 | Papahadjopoulos et al. |
| 4,503,223 A | 3/1985 | Reilly, Jr. |
| 4,737,323 A | 4/1988 | Martin et al. |
| 5,134,127 A | 7/1992 | Stella et al. |
| 6,603,000 B2 | 8/2003 | Yee et al. |
| 2007/0105793 A1 | 5/2007 | Hendrix |
| 2008/0139628 A1* | 6/2008 | Behan et al. ................... 514/356 |
| 2009/0054499 A1 | 2/2009 | Cefali |
| 2009/0312355 A1 | 12/2009 | Bachovchin et al. |
| 2009/0326013 A1 | 12/2009 | Hendrix |

FOREIGN PATENT DOCUMENTS

| | | |
|---|---|---|
| WO | WO-96/14057 | 5/1996 |
| WO | WO-2004/111004 A1 | 12/2004 |
| WO | WO-2008/106227 A1 | 9/2008 |
| WO | WO-2010/056549 A1 | 5/2010 |

OTHER PUBLICATIONS

Swanson, D. M. et al., "Heterocyclic Replacement of the Central Phenyl Core of Diamine-based Histamine H3 Receptor Antagonists." Euro. J. of Med. Chemistry, 44:4413-4425 (2009).
Berge, S. M. et al., "Pharmaceutical Salts", *J. Pharm. Sci.*, 66(1):1-19 (USA, Jan. 1977).
Blankenhorn, D. H. et al., "Beneficial Effects of Combined Colestipol-Niacin Therapy on Coronary Atherosclerosis and Coronary Venous Bypass Grafts", *JAMA*, 257(23):3233-3240 (USA, Jun. 19, 1987).
Canner, P. L. et al., "Fifteen Year Mortality in Coronary Drug Project Patients: Long-Term Benefit With Niacin", *J. Am. Coll. Cardiol.*, 8(6):1245-1255 (USA, Dec. 1986).
Carlson, L. A., "Nicotinic acid and inhibition of fat mobilizing lipolysis. Present status of effects on lipid metabolism", *Adv. Exp. Med. Biol.*, 109:225-238 (USA, 1978).
Carlson, L. A. et al., "Nicotinic Acid in the Rat. II. Acute Effects of Nicotinic Acid on Plasma, Liver, Heart, and Muscle Lipids", *Acta Med. Scand.*, 180(5):571-579 (Stockholm, Sweden,1966).
Cashin-Hemphill, L. et al., "Beneficial Effects of Colestipol-Niacin on Coronary Artherosclerosis. A 4-year Follow-up", *JAMA*, 264(23):3013-3017 (USA, Dec. 19, 1990).
Dordunoo, S. K. et al., "Preformulation Studies on Solid Dispersions Containing Triamterene or Temezepam in Polyethylene Glycols or Gelucire 44/14 for Liquid Filling of Hard Gelatin Capsules", *Drug Development and Industrial Pharmacy*, 17(12):1685-1713 (Marcel Dekker, Inc., UK, 1991).
Kashyap, M. L. et al., "New Combination Niacin/Statin Formulation Shows Pronounced Effects on Major Lipoproteins and is Well Tolerated", *J. Am. Coll. Card. Suppl.*, 35:326A (2000) (Abstract).
McKenney, J. M. et al., "A Comparison of the Efficacy and Toxic Effects of Sustained- vs. Immediate-Release Niacin in Hypercholesterolemic Patients", *Jama*, 271(9):672-677 (USA, Mar. 2, 1994).

(Continued)

*Primary Examiner* — Brandon Fetterolf
*Assistant Examiner* — Ana Z Muresan
(74) *Attorney, Agent, or Firm* — Dana M. Gordon; Foley Hoag LLP

(57) ABSTRACT

Disclosed are heterocyclylalkyl-substituted and heteroaralkyl-substituted pyridines, and pharmaceutically acceptable salts and prodrugs thereof, that are active against a range of mammalian therapeutic indications.

29 Claims, 28 Drawing Sheets

(56) References Cited

OTHER PUBLICATIONS

Priego, J. G. et al., "Action of etofibrate, clofibrate and nicotinic acid of the metabolism of lipids in normolipemic rats. Short term effects and methods of action", *Arch. Farmacol. Toxicol.*, 29:29-42 (1979).

Sheen, P. C. et al., "Bioavailability of a Poorly Water-Soluble Drug from Tablet and Solid Dispersion in Humans", *J. Pharm. Sci.*, 80(7):712-714 (American Pharmaceutical Assoc., USA, Jul. 1991).

Soga, T. et al., "Molecular identification of nicotinic acid receptor", Biochem. Biophys. Res. Comm., 303:364-369 (Elsevier Academic Press, 2003).

Stafford, R. S. et al., "Variations in Cholesterol Management Practices of U.S. Physicians", J. Am. Coll. Cardiol., 29(1):139-146 (USA, Jan. 1997).

Van Uden, W. et al., "Cyclodextrins as a useful tool for bioconversions in plant cell biotechnology", Plant Cell Tiss. Org. Cult., 38:103-113 (Kluwer Academic Publishers, The Netherlands, 1994).

Walters, R. W. et al., "β-Arrestin1 mediates nicotinic acid-induced flushing, but not its antilipolytic effect, in mice", J. Clin. Invest., 119(5):1312-1321 (USA, May 2009).

Wenz, G., "Cyclodextrins as Building Blocks for Supramolecular Structures and Functional Units", *Agnew. Chem. Int. Ed. Engl.*, 33:803-822 (Weinheim, 1994).

Wise, A. et al., "Molecular Identification of High and Low Affinity Receptors for Nicotinic Acid", *J. Biol. Chem.*, 278(11):9869-9874 (USA, Mar. 14, 2003).

The Coronary Drug Project Research Group, "Clofibrate and Niacin in Coronary Heart Disease", *JAMA*, 231(4):360-381 (USA, Jan. 27, 1975).

Niaspan® product label downloaded from http://www.pdr.net/drugpages/productlabelingprintaspx?mpcode=00403000 dated Jan. 31, 2012.

International Search Report and Written Opinion of the International Searching Authority from PCT application PCT/US2011/041869 filed Jun. 24, 2011.

Extended European Search Report from corresponding European regional application EP 11799002.8 dated Nov. 13, 2013.

\* cited by examiner

NIACIN MIMETICS, AND METHODS OF USE THEREOF

RELATED APPLICATION

This application claims the benefit of priority to U.S. Provisional Patent Application Ser. No. 61/358,245, filed Jun. 24, 2010, the contents of which are hereby incorporated by reference.

BACKGROUND

Hyperlipidemia and hypercholesterolemia are conditions that have a well established correlation with increased risk of other conditions, such as heart attacks, atherosclerosis, and other deleterious ailments. There are numerous agents available for lowering cholesterol and lipid levels, including gemfibrizol, probucol, and, more recently, the "statins" (e.g., lovastatin).

Niacin (nicotinic acid), a water soluble B-complex vitamin, is used orally for the treatment of hyperlipidemia. Niacin has been shown to be effective in reducing total plasma cholesterol (C), low-density lipoproteins LDL-C and very low density lipoprotein triglycerides (VLDL-triglycerides), all of which are associated with health risks. Simultaneously, niacin raises serum levels of high density lipoproteins (HDL-C), which are considered a "healthy" lipoprotein, in patients with types II, III, IV, and V hyperlipoproteinemia.

Although the mechanism by which niacin alters lipid profiles has not been well defined, its mechanisms of action have been shown to include inhibition of free fatty acid release from adipose tissue (see Carlson, L. A., Froberg, S. O. and Nye, E. R., Nicotinic acid in the rat. 11. Acute effects of nicotinic acid on plasma, liver, heart, and muscle lipids, Acta Med Scand 180: 571-579, 1966), and increased lipoprotein lipase activity (see Priego, J. G., Pina, M., Armijo, M., Sunkel, C. and Maroto, M. L., Action of etofibrate, clofibrate and nicotinic acid on the metabolism of lipids in normolipemic rats. Short term effects and method of action, Arch Farmacol Toxicol 5: 29-42, 1979). More than 30 million Americans have elevated blood LDL-C levels. HMG-CoA reductase inhibitors (statins) are the most widely used class of drugs for treating patients with elevated levels of LDL-C. Niacin, however, is the only drug recommended by the American Heart Association for HDL improvement in primary prevention of cardiovascular diseases in addition to lowering LDL-C. Niacin therapy is not only cost-effective as a monotherapy, but it is also beneficial as a combination therapy because it complements the effects of other classes of lipid-lowering drugs. However, niacin is a second or third choice for isolated hypercholesterolemia because of a high incidence of side effects associated with oral niacin therapy. Nevertheless, it has a therapeutic advantage as a monotherapy when reduction of both LDL-C and triglycerides are desired, such as for patients with severe combined hyperlipidemia.

Niacin may also be used in combination with other cholesterol-lowering agents, such as the "statins", to maximize lipid-lowering activity. One study showed that a niacin/lovastatin combination is highly effective in lowering LDL-C, triglycerides and lipoprotein (a) (Lp(a)) while retaining niacin's potency in raising HDL-C (Kashyap, M. L., Evans R., Simmons, P. D., Kohler, R. M. and McGoven, M. E., New combination niacin/statin formulation shows pronounced effects on major lipoproteins and well tolerated, J Am Coll Card Suppl. A 35: 326, 2000).

Niacin has been widely used for reducing serum cholesterol levels because it is considered a cost-effective therapy. Daily oral doses of 2-3 g niacin in humans reduce levels of total-C and LDL-C by an average of 20% to 30%, reduce triglyceride levels 35% to 55%, increase HDL-C 20% to 35%, and reduce Lp(a). Niacin also reduces total mortality as well as mortality from coronary artery disease (see The Coronary Drug Project Research Group, JAMA 231: 360-381, 1975; and Canner, P. L., Berge, K. G., Wenger, N. K., Stamler, J., Friedman, L., Prineas, R. J. and Friedewald, W., Fifteen year mortality in Coronary Drug Project patients: long-term benefit with niacin, J Am Coll Cardiol 8: 1245-1255, 1986.) and it helps to slow or reverse the progression of atherosclerosis (see Blankenhorn, D. H., Nessim, S. A., Johnson, R. L., Samnarco, M. E., Azen, S. P. and Cashin-Hemphill, L., Beneficial effects of combined colestipol-niacin therapy on coronary atherosclerosis and coronary venous bypass grafts, JAMA 257: 3233-3240, 1987; and Cashin-Hemphill L.; Mack, W. J., Pogoda, J. M., Samnarco, M. E., Azen, S. P. and Blankenhorn, D. H., Beneficial effects of colestipol-niacin on coronary atherosclerosis. A 4-year follow-up, JAMA 264: 3013-3017, 1990).

Unfortunately, oral niacin therapy has side effects that limit its utility. Although niacin is a vitamin, it must be used in therapeutic doses to lower cholesterol. At these doses, both immediate-release and sustained-release niacin can have several side effects. The most common side effect of niacin is flushing, a warm feeling in the skin usually associated with redness and sometimes itching. Flushing is not dangerous, but most patients find it very uncomfortable, which seriously limits patient compliance with niacin therapy. Niacin-induced flushing can be substantially attenuated by pretreatment with cyclooxygenase inhibitors, suggesting that the vasodilation is caused by a prostaglandin-mediated mechanism (see Carlson, L. A., Nicotinic acid and inhibition of fat mobilizing lipolysis. Present status, of effects on lipid metabolism, Adv Exp Med Biol 109: 225-23 8, 1978).

Liver function tests are always monitored in patients taking niacin since elevation of serum transaminase levels has been associated with niacin treatment, and sustained-release niacin formulations have been associated with more serious liver problems (see McKenney, J. M., Proctor, J. D., Harris, S., and Chinchili, V. M., A comparison of the efficacy and toxic effects of sustained- vs immediate-release niacin in hypercholesterolemic patients, JAMA 271: 672-777, 1994; and Stafford, R. S., Blumenthal, D. and Pasternak, R. C., Variations in cholesterol management practices of U.S. physicians, J Am Coll Cardiol 29: 139-146, 1997). Other known side effects of oral niacin therapy include activation of peptic ulcers, gout, and worsening of diabetes control. Accordingly, the safety and efficacy of oral niacin therapy is undermined by the need for careful clinical monitoring and the compound's side-effect profile.

SUMMARY

One aspect of the present invention relates to niacin analogs, as defined herein, and methods of use thereof against one or more mammalian or human therapeutic indications.

One aspect of the present invention relates to heterocyclylalkyl-substituted and heteroaralkyl-substituted pyridines, and pharmaceutically acceptable salts thereof, that are active against a range of mammalian maladies. In certain embodiments, said pyridines or salts thereof comprise at the 3-position or 5-position a substituent comprising a functional group that is substantially anionic at physiological pH. In certain embodiments, said pyridines or salts thereof comprise at the 2-position or 6-position a substituent comprising a functional group that is electron donating to the pyridine ring. In certain embodiments, said pyridines or salts thereof comprise at the 5-position a substituent comprising a functional group that is substantially anionic at physiological pH; and at the 2-position a substituent comprising a functional group that is electron donating to the pyridine ring.

An aspect of the invention is a method of reducing a serum or plasma level of at least one lipid selected from the group consisting of total cholesterol, low-density lipoprotein (LDL) cholesterol, triglycerides, and lipoprotein (a), comprising orally administering to a human in need thereof an effective amount of a niacin analog or a pharmaceutically acceptable salt thereof, wherein said oral administration is characterized by reduced flushing and reduced hepatocellular damage, as compared to oral administration of an equimolar dose of immediate-release niacin.

In one embodiment, peak concentration ($C_{max}$) for the niacin analog is 40 percent or less of $C_{max}$ for the equimolar oral dose of immediate-release niacin.

In one embodiment, the ratio of peak concentration to area under the curve at 24 hours ($C_{max}/AUC_{0-24}$) for the niacin analog is 0.35 $h^{-1}$ or less.

In one embodiment, the time to peak concentration ($t_{max}$) for the niacin analog is in the range of 1 to 5 hours.

In one embodiment, the niacin analog has an $EC_{50}$ for β-arrestin-mediated GPR109A function which is at least 10 times greater than the $EC_{50}$ of niacin for β-arrestin-mediated GPR109A function.

In one embodiment, the niacin analog when administered orally to a human also increases a serum or plasma level of high-density lipoprotein (HDL) cholesterol.

In one embodiment, the oral administration is characterized by substantially no increase in serum levels of aspartate aminotransferase (AST), alanine aminotransferase (ALT), or both.

In one embodiment, the method further comprises administering to the human a statin. In one embodiment, the statin is selected from the group consisting of atorvastatin, cerivastatin, fluvastatin, lovastatin, mevastatin, pitavastatin, pravastatin, rosuvastatin and simvastatin.

In one embodiment, the method further comprises administering to the human at least one additional therapeutic agent selected from the group consisting of 11β HSD-1 inhibitors, 5HT transporter inhibitors, 5HT2c agonists, 5-LO or FLAP inhibitors, α-glucosidase inhibitors, ABCA1 enhancers, ACC inhibitors, AcylCoA:cholesterol O-acyltransferase inhibitors, acyl-estrogens, antidiabetic agents, anti-dyslipidemic agents, anti-hypertensive agents, anti-oxidants, Apo A1 mimetics, Apo A1 modulators, Apo E mimetics, apolipoprotein-B secretion/microsomal triglyceride transfer protein (apo-B/MTP) inhibitors, appetite suppressants, aspirin, β3 agonists, bile acid reabsorption inhibitors, bile acid sequestrants, bombesin agonists, BRS3 agonists, $CB_1$ antagonists/inverse agonists, CCK-A agonists, cholesterol absorption inhibitor, cholesterol transport inhibitors, cholesteryl ester transfer protein (CETP) inhibitors, CNTF, CNTF agonists/modulators, a combination of ezetimibe and simvastatin and/or atorvastatin, CSL-111, dehydroepiandrosterone, delipidated HDL, DGAT antisense oligos, DGAT1 inhibitors, DGAT2 inhibitors, dicarboxylate transporter inhibitors, dopamine agonists, DP receptor antagonists, ezetimibe, FAS inhibitors, fatty acid binding protein (FABP) inhibitors, fatty acid transporter inhibitors, fatty acid transporter protein (FATP) inhibitors, flush inhibitors, FXR receptor modulators, galanin receptor antagonists, gemcabene, ghrelin antagonists, ghrelin antibodies, GLP-1 agonists, glucagon-like peptide-1 receptor agonists, glucocorticoid agonists/antagonists, glucose transporter inhibitors, HDL mimetics, HMG CoA reductase inhibitor compounds, HMG-CoA synthetase inhibitors, hormone sensitive lipase antagonists, human agouti-related proteins (AGRP), $H_3$ antagonists/inverse agonists, inorganic cholesterol sequestrants, L-4f, lapaquistat, leptin agonists/modulators, leptins, lipase inhibitors, lipoprotein synthesis inhibitors, lorapoprant, low density lipoprotein receptor inducers or activators, Lp(a) reducers, LXR receptor agonists, lyn kinase inhibitor, Mc3r agonists, Mc4r agonists, MCH1R antagonists, MCH2R agonists/antagonists, melanin concentrating hormone antagonists, mGluR5 antagonists, microsomal triglyceride transport inhibitors, monoamine reuptake inhibitors, natural water soluble fibers, NE transporter inhibitors, neuromedin U receptor agonists, neuropeptide-Y antagonists, niacin or niacin receptor agonists, nicotinic acid, noradrenergic anorectic agents, NPY1 antagonists, NPY2 agonists, NPY4 agonists, NPY5 antagonists, non-steroidal anti-inflammatory drug (NSAID) agents, omega-3 fatty acids, opioid antagonists, orexin receptor antagonists, PDE inhibitors, phentermine, phosphate transporter inhibitors, phytopharm compound 57, plant stanols and/or fatty acid esters of plant stanols, platelet aggregation inhibitors, PPAR-α agonists, PPAR-δ agonists, PPAR-δ partial agonists, PPAR-γ agonists, probucol, renin angiotensin inhibitors, reversed-4F, SCD-1 inhibitors, serotonin reuptake inhibitors, SGLT2 inhibitors, squalene epoxidase inhibitors, squalene synthesis inhibitors, sterol biosynthesis inhibitors, sympathomimetic agonists, thyroid hormone β agonists, thyromimetic agents, topiramate, triglyceride synthesis inhibitors, UCP-1 activators, UCP-2 activators, UCP-3 activators, and urocortin binding protein antagonists.

An aspect of the invention is a pharmaceutical composition, comprising a niacin analog or a pharmaceutically acceptable salt thereof, and at least one pharmaceutically acceptable excipient; wherein said composition is formulated for oral administration; the niacin analog when administered orally to a human reduces a serum or plasma level of at least one lipid selected from the group consisting of total cholesterol, low-density lipoprotein (LDL) cholesterol, triglycerides, and lipoprotein (a); and oral administration of the composition is characterized by reduced flushing and reduced hepatocellular damage, as compared to administration of an equimolar oral dose of niacin.

In certain embodiments, the invention relates to any one of the aforementioned compositions, wherein peak serum or plasma concentration ($C_{max}$) for the niacin analog is 40 percent or less of $C_{max}$ for the equimolar oral dose of niacin. In one embodiment, peak serum or plasma concentration ($C_{max}$) for the niacin analog is 35 percent or less of $C_{max}$ for the equimolar oral dose of niacin. In one embodiment, peak serum or plasma concentration ($C_{max}$) for the niacin analog is 30 percent or less of $C_{max}$ for the equimolar oral dose of niacin. In one embodiment, peak serum or plasma concentration ($C_{max}$) for the niacin analog is 25 percent or less of $C_{max}$ for the equimolar oral dose of niacin. In one embodiment, peak serum or plasma concentration ($C_{max}$) for the niacin analog is 20 percent or less of $C_{max}$ for the equimolar oral dose of niacin. In one embodiment, peak serum or plasma concentration ($C_{max}$) for the niacin analog is 15 percent or less of $C_{max}$ for the equimolar oral dose of niacin. In one embodiment, peak serum or plasma concentration ($C_{max}$) for the niacin analog is 10 percent or less of $C_{max}$ for the equimolar oral dose of niacin. In one embodiment, peak serum or plasma concentration ($C_{max}$) for the niacin analog is 5 percent or less of $C_{max}$ for the equimolar oral dose of niacin. In one embodiment, peak serum or plasma concentration ($C_{max}$) for the niacin analog is 1 percent or less of $C_{max}$ for the equimolar oral dose of niacin. For each of the foregoing embodiments, it is to be understood that comparison is made with an immediate release formulation of niacin. Methods useful for measuring the concentration are disclosed in detail hereinbelow.

In certain embodiments, the invention relates to any one of the aforementioned compositions, wherein the ratio of peak serum or plasma concentration ($C_{max}$) to area under the curve at 24 hours ($AUC_{0-24}$) (i.e., the ratio $C_{max}/AUC_{0-24}$) for the niacin analog is $0.35\ h^{-1}$ or less. In one embodiment, the ratio of peak concentration to area under the curve at 24 hours ($C_{max}/AUC_{0-24}$) for the niacin analog is $0.30\ h^{-1}$ or less. In one embodiment, the ratio of peak concentration to area under the curve at 24 hours ($C_{max}/AUC_{0-24}$) for the niacin analog is $0.25\ h^{-1}$ or less. In one embodiment, the ratio of peak concentration to area under the curve at 24 hours ($C_{max}/AUC_{0-24}$) for the niacin analog is $0.20\ h^{-1}$ or less. In one embodiment, the ratio of peak concentration to area under the curve at 24 hours ($C_{max}/AUC_{0-24}$) for the niacin analog is $0.15\ h^{-1}$ or less. In one embodiment, the ratio of peak concentration to area under the curve at 24 hours ($C_{max}/AUC_{0-24}$) for the niacin analog is $0.10\ h^{-1}$ or less. In one embodiment, the ratio of peak concentration to area under the curve at 24 hours ($C_{max}/AUC_{0-24}$) for the niacin analog is $0.05\ h^{-1}$ or less. In one embodiment, the ratio of peak concentration to area under the curve at 24 hours ($C_{max}/AUC_{0-24}$) for the niacin analog is $0.01\ h^{-1}$ or less.

In certain embodiments, the invention relates to any one of the aforementioned compositions, wherein the time to peak serum or plasma concentration ($t_{max}$) for the niacin analog is in the range of 30 minutes to 5 hours. In one embodiment, the time to peak concentration ($t_{max}$) for the niacin analog is in the range of 1 to 5 hours. In one embodiment, the time to peak concentration ($t_{max}$) for the niacin analog is in the range of 1 to 4 hours. In one embodiment, the time to peak concentration ($t_{max}$) for the niacin analog is in the range of 1 to 3 hours. In one embodiment, the time to peak concentration ($t_{max}$) for the niacin analog is in the range of 1 to 2 hours.

In an embodiment, the niacin analog has an $EC_{50}$ for β-arrestin-mediated GPR109A function which is at least 10 times greater than the $EC_{50}$ of niacin for β-arrestin-mediated GPR109A function.

In an embodiment, the niacin analog, when administered orally to a human, also increases a serum or plasma level of high-density lipoprotein (HDL) cholesterol.

In an embodiment, the niacin analog, when administered orally to a human, induces substantially no increase in serum levels of aspartate aminotransferase (AST), alanine aminotransferase (ALT), or both.

In an embodiment, the niacin analog, when administered orally to a human, induces substantially no increase in serum levels of uric acid, glucose, or both.

Another aspect of the invention relates to a pharmaceutical composition, comprising a compound of the present invention or a pharmaceutically acceptable salt thereof; and a pharmaceutically acceptable excipient. Yet another aspect of the invention relates to a pharmaceutical composition, comprising a compound of the present invention or a pharmaceutically acceptable salt thereof; niacin; and a pharmaceutically acceptable excipient.

Another aspect of the invention relates to a pharmaceutical composition, comprising a compound of the present invention or a pharmaceutically acceptable salt thereof; a statin selected from the group consisting of atorvastatin, cerivastatin, fluvastatin, lovastatin, mevastatin, pitavastatin, pravastatin, rosuvastatin and simvastatin; and a pharmaceutically acceptable excipient. The present invention also relates to a pharmaceutical composition, comprising a compound of the present invention or a pharmaceutically acceptable salt thereof; niacin; a statin selected from the group consisting of atorvastatin, cerivastatin, fluvastatin, lovastatin, mevastatin, pitavastatin, pravastatin, rosuvastatin and simvastatin; and a pharmaceutically acceptable excipient. Additional therapeutic agents which can be co-administered with compounds of the invention are discussed below.

Niacin, or nicotinic acid, has established efficacy for the treatment of dyslipidemia, but the clinical use of niacin has been limited by cutaneous flushing, a well-recognized associated adverse effect. Flushing, which is estimated at a prevalence as high as 25% to 40%, has been cited as the major reason for the discontinuation of niacin therapy. A number of studies have established that moderate doses of prostaglandin inhibitors reduce the cutaneous flushing response from niacin administration. Other strategies for reducing flushing include regular consistent dosing, the use of extended-release formulations, patient education, dosing with meals or at bedtime, and the avoidance of alcohol, hot beverages, spicy foods, and hot baths or showers close to or after dosing. In certain embodiments, compounds of the present invention can have reduced occurrence or severity of flushing when administered to an animal, particularly a human patient.

For instance, compounds of the present invention do not cause flushing in the male C57BL/6 murine model of flushing, as measured by laser Doppler flowmetry, when administered at doses of up to 100 mg/kg, and even more preferably when administered at doses up to 200, 300, or even 500 mg/kg.

In certain embodiments, compounds of the present invention can be characterized by causing less flushing when administered orally when compared to the amount equivalent molar amount of NIASPAN® (niacin extended-release tablets, Abbott Laboratories). In certain embodiments, compounds of the present invention when administered orally to an average patient population, shows a reduction in the number of patients reporting flushing of greater than or equal to 5 on the visual analog scale orally when compared to the equivalent molar amount of NIASPAN®.

The present invention also relates to a method of treating a disease, disorder, or condition selected from the group consisting of hyperlipidemia, hypercholesterolemia, lipodystrophy, dyslipidemia, atherosclerosis, and coronary artery disease, comprising the step of administering to a mammal in need thereof a therapeutically effective amount of a compound or pharmaceutical composition of the present invention.

Another aspect of the present invention relates to a method of treating a disease, disorder, or condition selected from the group consisting of metabolic syndrome, obesity, fatty liver disease, and diabetes, comprising the step of administering to a mammal in need thereof a therapeutically effective amount of a compound or pharmaceutical composition of the present invention.

Another aspect of the present invention relates to a method of raising serum high-density lipoprotein (HDL) levels, comprising the step of: administering to a mammal in need thereof a therapeutically effective amount of a compound or pharmaceutical composition of the present invention.

Another aspect of the present invention relates to a method of lowering serum low-density lipoprotein (LDL) levels or lowering serum lipoprotein (a) levels, comprising the step of administering to a mammal in need thereof a therapeutically effective amount of a compound or pharmaceutical composition of the present invention.

Another aspect of the present invention relates to a method of increasing the serum total concentrations of adiponectin, comprising the step of administering to a mammal in need thereof a therapeutically effective amount of a compound or pharmaceutical composition of the present invention.

Another aspect of the present invention relates to a method of treating a disease, disorder, or condition selected from the group consisting of congestive heart failure, cardiovascular disease, hypertension, coronary heart disease, angina, pellagra, Hartnup's syndrome, carcinoid syndrome, arterial occlusive disease, hypothyroidism, vasoconstriction, osteoarthritis, rheumatoid arthritis, Alzheimer's disease, disorders of the peripheral and central nervous system, hematological diseases, cancer, inflammation, respiratory diseases, and gastroenterological diseases, comprising the step of administering to a mammal in need thereof a therapeutically effective amount of a compound or pharmaceutical composition of the present invention.

The invention further provides a packaged pharmaceutical preparation of the invention, including an insert, label or other form of instruction to the patient to take the niacin analog once-a-day within 2 or 3 hours of waking, optionally with food.

Additional aspects, embodiments, and advantages of the invention are discussed below in detail.

BRIEF DESCRIPTION OF THE FIGURES

FIG. 12A, aspartate aminotransferase (AST).

DETAILED DESCRIPTION

Figure 1:
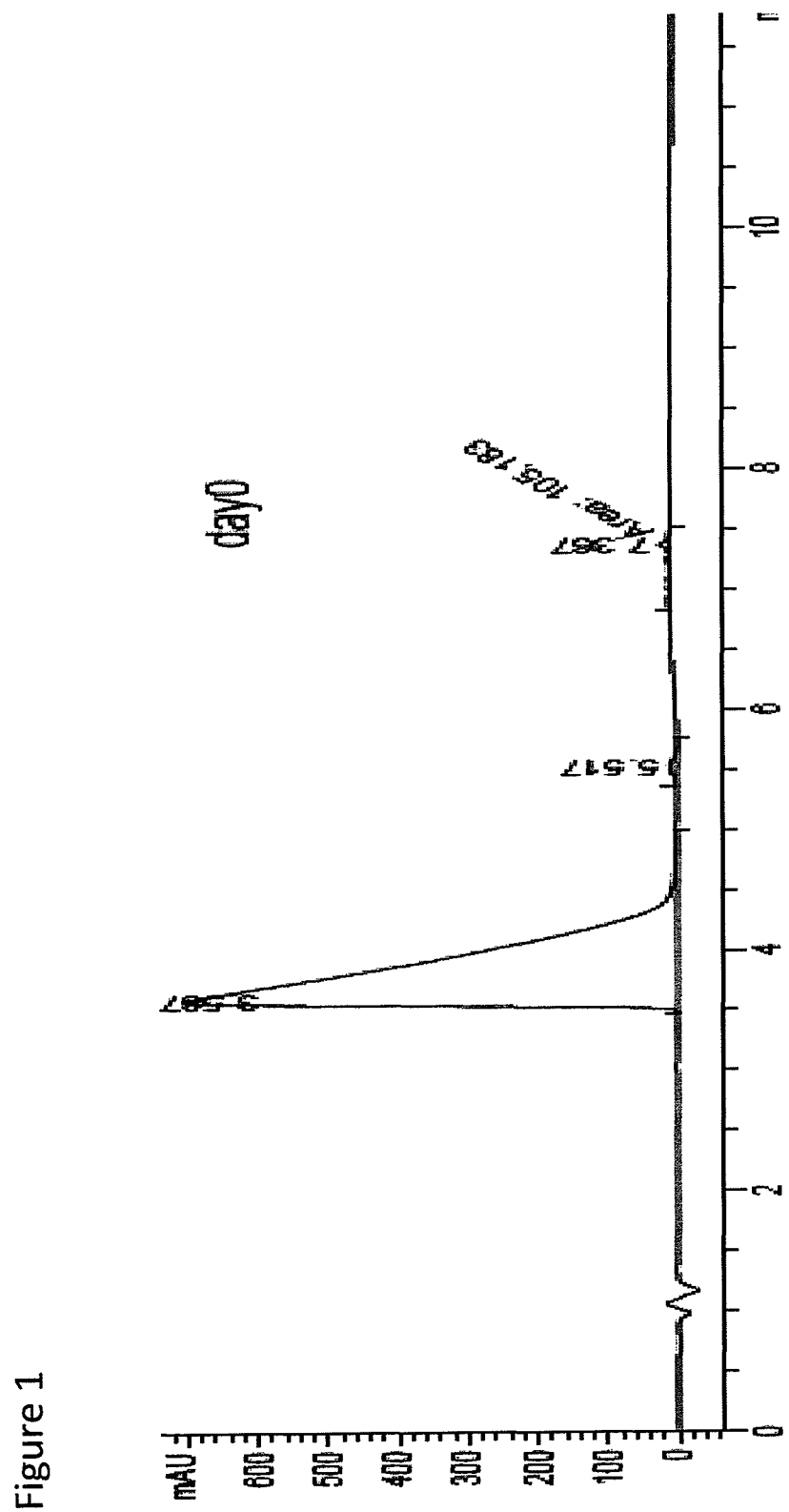
FIG. 1. Liquid chromatography-mass spectroscopy (LC-MS) trace for ARI-001 received from Shanghai SpeedChem (Shanghai, China). UV absorption at 215 nm was used to determine purity. The area of the peak at 3.59 min represents 98.9% of the total peak area of the trace.

One aspect of the invention relates to niacin analogs for use in raising serum HDL levels in mammals. In certain embodiments, the compounds of the invention have equal or greater HDL-raising ability than niacin while having less or no propensity to induce flushing, an undesirable side effect of niacin itself when used in doses sufficient to raise serum HDL levels. Some non-flushing niacin analogs are described in U.S. Patent Application Publication No. 2009/0312355, which is hereby incorporated by reference in its entirety. In certain embodiments, key structural features of the compounds disclosed herein appear to include the placement of a heterocyclylalkyl or heteroaralkyl group para to the carboxyl group in niacin.

DEFINITIONS

For convenience, certain terms employed in the specification, examples, and appended claims are collected here. All definitions, as defined and used herein, supersede dictionary definitions, definitions in documents incorporated by reference, and/or ordinary meanings of the defined terms.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "solvate" refers to a pharmaceutically acceptable form of a specified compound, with one or more solvent molecules, that retains the biological effectiveness of such compound. Examples of solvates include compounds of the invention in combination with solvents such, for example, water (to form the hydrate), isopropanol, ethanol, methanol, dimethyl sulfoxide, ethyl acetate, acetic acid, ethanolamine, or acetone. Also included are formulations of solvate mixtures such as a compound of the invention in combination with two or more solvents.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms.

The term "lower" when appended to any of the groups listed below indicates that the group contains less than seven carbons (i.e., six carbons or less). For example "lower alkyl" refers to an alkyl group containing 1-6 carbons, and "lower alkenyl" refers to an alkyenyl group containing 2-6 carbons.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged). "Monocyclic" refers to compounds and/or groups with one ring; and "bicyclic" refers to compounds/and or groups with two rings.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this invention, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to 20, 1 to 15, or 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, 1-(1-ethylcyclopropyl)ethyl and 1-cyclohexylethyl.

The term "cycloalkyl" is a subset of alkyl which refers to cyclic hydrocarbon radical containing from 3 to 15, 3 to 10, or 3 to 7 carbon atoms. Representative examples of cycloalkyl include, but are not limited to, cyclopropyl and cyclobutyl.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene," is art-recognized, and as used herein pertains to a diradical obtained by removing two hydrogen atoms of an alkyl group, as defined above.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein refers to a radical of a non-aromatic, ring system, including, but not limited to, monocyclic, bicyclic and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxyl, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substiuents bound to the heterocyclyl group through an alkylene moiety (e.g., methylene).

The term "aryl," as used herein means a phenyl, naphthyl, phenanthrenyl, or anthracenyl group. The aryl groups of the present invention can be optionally substituted with 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxyl, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said subsituents bound to the heterocyclyl group through an alkylene moiety (e.g., methylene).

The term "arylene," is art-recognized, and as used herein pertains to a diradical obtained by removing two hydrogen atoms of an aryl ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-yl-ethyl.

The term "biaryl," as used herein means an aryl-substituted aryl, an aryl-substituted heteroaryl, a heteroaryl-substituted aryl or a heteroaryl-substituted heteroaryl, wherein aryl and heteroaryl are as defined herein. Representative examples include 4-(phenyl)phenyl and 4-(4-methoxyphenyl)pyridinyl.

The term "heteroaryl" as used herein include radicals of aromatic ring systems, including, but not limited to, monocyclic, bicyclic and tricyclic rings, which have 3 to 12 atoms including at least one heteroatom, such as nitrogen, oxygen, or sulfur. For purposes of exemplification, which should not be construed as limiting the scope of this invention: aminobenzimidazole, benzimidazole, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyoxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxyl, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said subsituents bound to the heteroaryl group through an alkylene moiety (e.g., methylene).

The term "heteroarylene," is art-recognized, and as used herein pertains to a diradical obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "fused bicyclyl" as used herein means the radical of a bicyclic ring system wherein the two rings are ortho-fused, and each ring, contains a total of four, five, six or seven atoms (i.e., carbons and heteroatoms) including the two fusion atoms, and each ring can be completely saturated, can contain one or more units of unsaturation, or can be completely unsaturated (e.g., in some case, aromatic). For the avoidance of doubt, the degree of unsaturation in the fused bicyclyl does not result in an aryl or heteroaryl moiety.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein some or all of the hydrogens are replaced with fluorines.

The term "haloalkylene," as used herein pertains to diradical obtained by removing two hydrogen atoms of an haloalkyl group, as defined above.

The term "hydroxy" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkyenyloxy", "alkynyloxy", "carbocyclyloxy", and "heterocyclyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethyl-phenylethoxy, and 2,3-dimethylpyridinylmethoxy.

The term "sulfhydryl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkyenylthio", "alkynylthio", "carbocyclylthio", and "heterocyclylthio" are likewise defined.

The term "arylthio" as used herein means an aryl group, as defined herein, appended to the parent molecular moiety through an sulfur. The term "heteroarylthio" is likewise defined.

The term "arylalkylthio" or "aralkylthio" as used herein means an arylalkyl group, as defined herein, appended to the parent molecular moiety through a sulfur. The term "heteroarylalkylthio" is likewise defined.

The term "sulfonyl" as used herein refers to —S(=O)$_2$— group.

The term "sulfonic acid" as used herein refers to —S(=O)$_2$ OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluororalkylsulfonyl", "alkenylsulfonyl", "alkynylsulfonyl", "carbocyclylsulfonyl", "heterocyclylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl. The terms "haloalkoxysulfonyl", "fluoroalkoxysulfonyl", "alkenyloxysulfonyl", "alkynyloxysulfonyl", "carbocyclyloxysulfonyl", "heterocyclyloxysulfonyl", "aryloxysulfonyl", "aralkyloxysulfonyl", "heteroaryloxysulfonyl" and "heteroaralkyloxysulfonyl" are likewise defined.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "aminosulfonyl" as used herein means an amino group, as defined herein, appended to the parent molecular moiety through a sulfonyl group.

The term "sulfinyl" as used herein refers to —S(=O)— group. Sulfinyl groups are as defined above for sulfonyl groups. The term "sulfinic acid" as used herein refers to —S(=O)OH.

The term "oxy" refers to a —O— group.

The term "carbonyl" as used herein means a —C(=O)— group.

The term "thiocarbonyl" as used herein means a —C(=S)— group.

The term "formyl" as used herein means a —C(=O)H group.

The term "acyl" as used herein refers to any group or radical of the form —C(=O)R, where R is an organic group. An example of the acyl group is the acetyl group (—C(=O)CH$_3$).

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenylcarbonyl", "alkynylcarbonyl", "carbocyclylcarbonyl", "heterocyclylcarbonyl", "arylcarbonyl", "aralkylcarbonyl", "heteroarylcarbonyl", and "heteroaralkylcarbonyl" are likewise defined.

The term "carboxyl" as used herein means a —CO$_2$H group.

An "isostere of a carboxyl group" as used herein refers to a group which is isosteric to a carboxyl group. Examples of isosters of a carboxyl group include tetrazolyl, oxazolidinonyl, 3-isoxazolyl, hydroxyisoxazolyl, sulfonic acid, sulfinic acid, acylsulphonamide, phosphonic acid, phosphinic acid, hydantoin, pyrrolidionyl, boronic acid, hydroxamic acid, acylcyanamide and oxadiazolonyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "haloalkoxycarbonyl", "fluoroalkoxycarbonyl", "alkenyloxycarbonyl", "alkynyloxycarbonyl", "carbocyclyloxycarbonyl", "heterocyclyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "haloalkylcarbonyloxy", "fluoroalkylcarbonyloxy", "alkenylcarbonyloxy", "alkynylcarbonyloxy", "carbocyclylcarbonyloxy", "heterocyclylcarbonyloxy", "arylcarbonyloxy", "aralkylcarbonyloxy", "heteroarylcarbonyloxy", and "heteroaralkylcarbonyloxy" are likewise defined.

The term "alkylsulfonyloxy" as used herein means an alkylsulfonyl group, as defined herein, appended to the parent molecular moiety through an oxygen atom. The terms "haloalkylsulfonyloxy", "fluoroalkylsulfonyloxy", "alkenylsulfonyloxy", "alkynylsulfonyloxy", "carbocyclylsulfonyloxy", "heterocyclylsulfonyloxy", "arylsulfonyloxy", "aralkylsulfonyloxy", "heteroarylsulfonyloxy", "heteroaralkylsulfonyloxy", "haloalkoxysulfonyloxy", "fluoroalkoxysulfonyloxy", "alkenyloxysulfonyloxy", "alkynyloxysulfonyloxy", "carbocyclyloxysulfonyloxy", "heterocyclyloxysulfonyloxy", "aryloxysulfonyloxy", "aralkyloxysulfonyloxy", "heteroaryloxysulfonyloxy" and "heteroaralkyloxysulfonyloxy" are likewise defined.

The term "amino" or "amine" as used herein refers to —$NH_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "cyano" as used herein means a —C≡N group.

The term "nitro" as used herein means a —$NO_2$ group.

The term "azido" as used herein means a —$N_3$ group.

The term "phosphinyl" or "phosphino" as used herein includes —$PH_3$ and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "phosphoryl" as used herein refers to —P(=O)$OH_2$ and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "silyl" as used herein includes $H_3Si$— and substituted derivatives thereof wherein one, two or three of the hydrogens are independently replaced with substitutuents selected from alkyl, haloalkyl, fluoroalkyl, alkenyl, alkynyl, carbocyclyl, heterocyclyl, aryl, aralkyl, heteroaryl, and heteroaralkyl. Representitive examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

The term "treating" as used herein, encompasses the administration and/or application of one or more compounds described herein, to a subject, for the purpose of providing prevention of or management of, and/or remedy for a condition. "Treatment" for the purposes of this disclosure, may, but does not have to, provide a cure; rather, "treatment" may be in the form of management of the condition. When the compounds described herein are used to treat unwanted proliferating cells, including cancers, "treatment" includes partial or total destruction of the undesirable proliferating cells with minimal destructive effects on normal cells. A desired mechanism of treatment of unwanted rapidly proliferating cells, including cancer cells, at the cellular level is apoptosis.

The term "to treat" as used herein thus embraces not only to cure, but also to slow the progression of and/or reduce the severity of a disease, disorder, or condition. In one embodiment, "treat" can encompass "prevent".

The term "preventing" as used herein includes either preventing or slowing the onset of a clinically evident disease progression altogether or preventing or slowing the onset of a preclinically evident stage of a disease in individuals at risk. This includes prophylactic treatment of those at risk of developing a disease.

The term "subject" for purposes of treatment includes any human or animal subject who has been diagnosed with, has symptoms of, or is at risk of developing a disorder. For methods of prevention the subject is any human or animal subject.

The term "optionally deuterated" as used herein refers to any radical, as described above, wherein one or more hydrogens has been replaced with a deuterium. Examples of deuterated alkyl include —$CD_2H$ and —$CD_3$.

The term "polyol" as used herein refers to small molecules and polymers which have more than one hydroxyl.

As used herein, a "carbohydrate" (or, equivalently, a "sugar") is a saccharide (including monosaccharides, oligosaccharides and polysaccharides) and/or a molecule (including oligomers or polymers) derived from one or more monosaccharides, e.g., by reduction of carbonyl groups, by oxidation of one or more terminal groups to carboxylic acids, by replacement of one or more hydroxy group(s) by a hydrogen atom, an amino group, a thiol group or similar heteroatomic groups, etc. The term "carbohydrate" also includes derivatives of these compounds. In some cases, the carbohydrate may be a pentose (i.e., having 5 carbons) or a hexose (i.e., having 6 carbons); and in certain instances, the carbohydrate may be an oligosaccharide comprising pentose and/or hexose units, e.g., including those described above.

"Carbohydrate" and "sugar" as used herein also includes sugar-mimetics and sugar-like moieties. Sugar-mimetics are well known to one of ordinary skill in the art and include those described in detail in "Essentials of Glycobiology" Edited by Varki, A., et al, Cold Spring Harbor Laboratory Press. Cold Spring Harbor, N.Y. 2002. For example, sugar-mimetic groups contemplated by the present invention include cyclitols, such as a cycloalkane containing one hydroxyl group on each of three or more ring atoms, as defined by IUPAC convention. In other embodiments, such cyclitol moieties include inositols such as scyllo-inositol. Suitable sugar-like moieties include acyclic sugar groups. Such groups include linear alkylols and erythritols, to name but a few. It will be appreciated that sugar groups can exist in either cyclic or acyclic form. Accordingly, acyclic forms of a sugar group are contemplated by the present invention as a suitable sugar-like moieties.

The term "polythiol" as used herein refers to small molecules and polymers which have more than one thiol.

Compounds

Niacin, also known as nicotinic acid, has the structure

One aspect of the invention relates to a compound represented by structure I, or a pharmaceutically acceptable salt thereof:

I wherein

A is a heterocyclyl or heteroaryl, optionally deuterated, containing from 5 to 12 ring atoms, including X and N, which is optionally substituted with 1-3 substituents, independently selected from the group consisting of alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;

X is O, S, N or N($R^6$);

Z is or an isostere of a carboxyl group;

$X^1$ is O or S;

$X^2$ is O or S;

R is hydrogen, alkyl, haloalkyl, alkenyl, alkynyl, carbocyclyl, heterocyclyl, heterocyclylalkyl, aryl, aralkyl, heteroaryl, heteroaralkyl, fused bicyclyl, carboxyalkyl, arylalkenylaryl, amido-substituted acetylaminoalkyl, carboxy-substituted acetylaminoalkyl, hydroxyalkylthioalkylthioalkyl, alkoxycarbonyloxyalkyl, alkylcarbonyloxyalkyl, or amidoalkyl;

$R^2$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;

$R^3$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;

$R^5$ is selected independently for each occurrence from the group consisting of hydrogen, alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;

$R^6$ is hydrogen or lower alkyl; and m is 1, 2, 3, or 4.

In certain embodiments, the invention relates to any one of the aforementioned compounds, wherein A represents a heterocyclyl.

In certain embodiments, the invention relates to any one of the aforementioned compounds, wherein A represents a heteroaryl.

In certain embodiments, the invention relates to any one of the aforementioned compounds, wherein A is a radical of a monocyclic ring having 5, 6 or 7 ring atoms.

In certain embodiments, the invention relates to any one of the aforementioned compounds, wherein A is a radical of a bicyclic ring having 9, 10, 11 or 12 ring atoms.

In certain embodiments, the invention relates to any one of the aforementioned compounds, wherein X is O.

In certain embodiments, the invention relates to any one of the aforementioned compounds, wherein X is S.

In certain embodiments, the invention relates to any one of the aforementioned compounds, wherein X is N.

In certain embodiments, the invention relates to any one of the aforementioned compounds, wherein X is N($R^6$).

In certain embodiments, the invention relates to any one of the aforementioned compounds, wherein X is N(H).

In certain embodiments, the invention relates to any one of the aforementioned compounds, wherein A is pyrrolidinyl, imidazolidinyl, thiazolidinyl, isothiazolidinyl, oxazolidinyl, oxadiazolidinyl, piperidinyl, piperazinyl, thiomorpholinyl or morpholinyl.

In certain embodiments, the invention relates to any one of the aforementioned compounds, wherein A is imidazolyl, pyrazolyl, isoxoazolyl, oxazolyl, isothiazolyl, thiazolyl, oxinyl, furazanyl, oxadiazolyl, thiadiazolyl, triazolyl, dithiazolyl, diazinyl, oxazinyl, thiazinyl, triazinyl, tetrazinyl, diazepinyl or thiazepinyl.

In certain embodiments, the invention relates to any one of the aforementioned compounds, wherein A is substituted with 1-3 substituents independently selected from the group consisting of lower alkyl, halogen, nitro, cyano, sulfonic acid, hydroxyl, alkoxyl, thiol, alkylthio, formyl, acyl, formyloxy, acyloxy, formylthio, acylthio, amine, alkylamine, formylamine, acylamine and carboxyl.

In certain embodiments, the invention relates to any one of the aforementioned compounds, wherein A is substituted with 1 substituent independently selected from the group consisting of lower alkyl, halogen, nitro, cyano, sulfonic acid, hydroxyl, alkoxyl, thiol, alkylthio, formyl, acyl, formyloxy, acyloxy, formylthio, acylthio, amine, alkylamine, formylamine, acylamine and carboxyl.

In certain embodiments, the invention relates to any one of the aforementioned compounds, wherein A is not substituted.

In certain embodiments, the invention relates to any one of the aforementioned compounds, wherein $R^2$ is hydrogen or lower alkyl.

In certain embodiments, the invention relates to any one of the aforementioned compounds, wherein $R^2$ is hydrogen.

In certain embodiments, the invention relates to any one of the aforementioned compounds, wherein $R^3$ is hydrogen or lower alkyl.

In certain embodiments, the invention relates to any one of the aforementioned compounds, wherein $R^3$ is hydrogen.

In certain embodiments, the invention relates to any one of the aforementioned compounds, wherein $R^2$ is hydrogen; and $R^3$ is lower alkyl.

In certain embodiments, the invention relates to any one of the aforementioned compounds, wherein $R^2$ is lower alkyl; and $R^3$ is hydrogen.

In certain embodiments, the invention relates to any one of the aforementioned compounds, wherein $R^2$ is hydrogen; and $R^3$ is hydrogen.

In certain embodiments, the invention relates to any one of the aforementioned compounds, wherein m is 1.

In certain embodiments, the invention relates to any one of the aforementioned compounds, wherein m is 2.

In certain embodiments, the invention relates to any one of the aforementioned compounds, wherein m is 3.

In certain embodiments, the invention relates to any one of the aforementioned compounds, wherein m is 4.

In certain embodiments, the invention relates to any one of the aforementioned compounds, wherein $R^5$ is selected independently for each occurrence from the group consisting of hydrogen, lower alkyl, halogen, nitro, cyano, sulfonic acid, hydroxyl, alkoxyl, thiol, alkylthio, formyl, acyl, formyloxy, acyloxy, formylthio, acylthio, amine, alkylamine, formylamine, acylamine and carboxyl.

In certain embodiments, the invention relates to any one of the aforementioned compounds, wherein $R^5$ is hydrogen.

In certain embodiments, the invention relates to any one of the aforementioned compounds, wherein Z is carboxyl.

In certain embodiments, the invention relates to any one of the aforementioned compounds, wherein Z is a carboxyl isostere.

In certain embodiments, the invention relates to any one of the aforementioned compounds, wherein Z is tetrazolyl, oxazolidinonyl, sulfonic acid, sulfinic acid, acylsulphonamide, phosphonic acid, phosphinic acid, hydantoin, pyrrolidione, 3-isoxazolyl, or boronic acid.

In certain embodiments, the invention relates to any one of the aforementioned compounds, wherein Z is

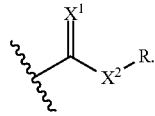

In certain embodiments, the invention relates to any one of the aforementioned compounds, wherein $X^1$ is O.

In certain embodiments, the invention relates to any one of the aforementioned compounds, wherein $X^1$ is S.

In certain embodiments, the invention relates to any one of the aforementioned compounds, wherein $X^2$ is O.

In certain embodiments, the invention relates to any one of the aforementioned compounds, wherein $X^2$ is S.

In certain embodiments, the invention relates to any one of the aforementioned compounds, wherein $X^1$ is O; and $X^2$ is O.

In certain embodiments, the invention relates to any one of the aforementioned compounds, wherein R is lower alkyl.

In certain embodiments, the invention relates to any one of the aforementioned compounds, wherein R is hydrogen.

In certain embodiments, the invention relates to any one of the aforementioned compounds, wherein R is

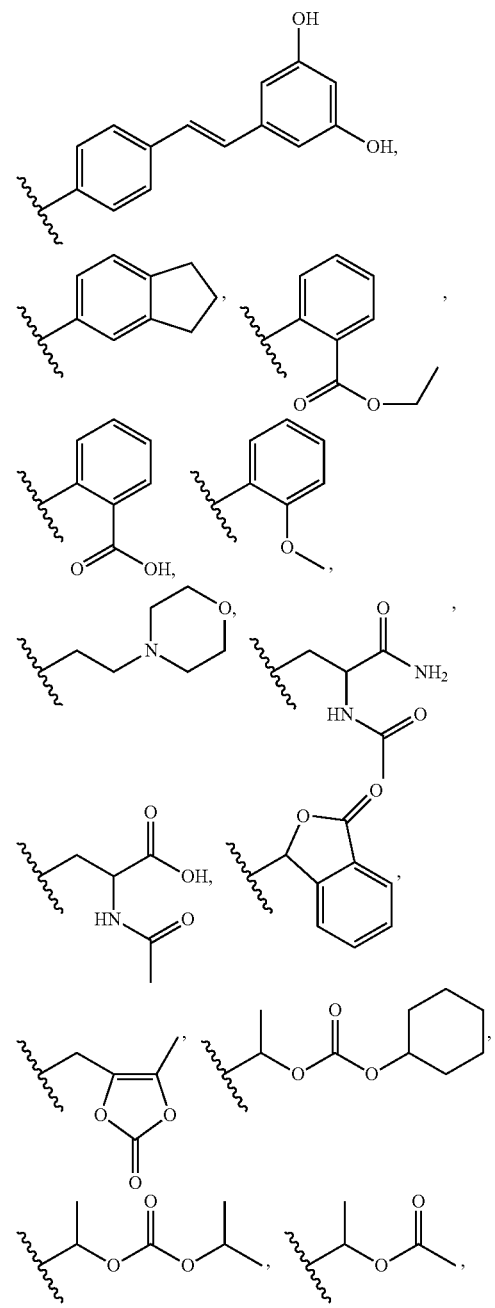

-continued

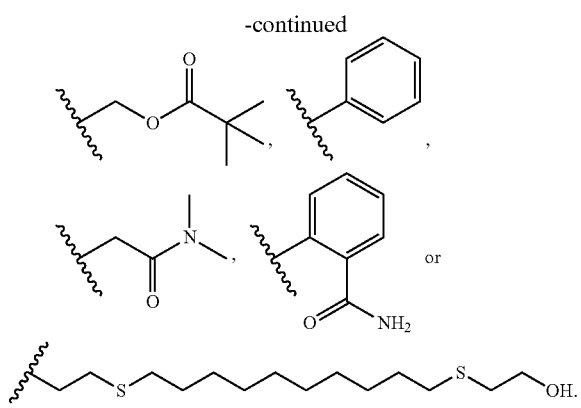

In certain embodiments, the invention relates to any one of the aforementioned compounds, wherein R represents an aliphatic group which is hydrolyzed to carboxyl under physiological conditions.

Another aspect of the invention relates to a compound represented by structure II, or a pharmaceutically acceptable salt thereof,

  II wherein, independently for each occurrence,
W is a polyol or polythiol;
p is 2-500 inclusive;
$R^1$ is

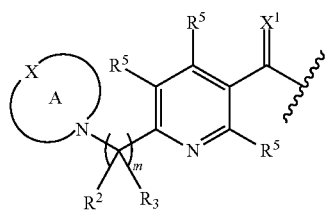

and is either appended to the polyol through an oxygen atom of the polyol or is appended to the polythiol through a sulfur atom of the polythiol;

A is a heterocyclyl or heteroaryl, optionally deuterated, containing from 5 to 12 ring atoms, including X and N, which is optionally substituted with 1-3 substituents, independently selected from the group consisting of alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;
X is O, S, N or $N(R^6)$;
$X^1$ is O or S;

$R^2$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;

$R^3$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;

$R^5$ is selected independently for each occurrence from the group consisting of hydrogen, alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;

$R^6$ is hydrogen or lower alkyl; and m is 1, 2, 3, or 4.

In certain embodiments, the invention relates to any one of the aforementioned compounds, wherein W is a polythiol.

In certain embodiments, the invention relates to any one of the aforementioned compounds, wherein W is a polyol.

In certain embodiments, the invention relates to any one of the aforementioned compounds, wherein said polyol is a carbohydrate.

In certain embodiments, the invention relates to any one of the aforementioned compounds, wherein said polyol is maltitol, sorbitol, xylitol or isomalt.

In certain embodiments, the invention relates to any one of the aforementioned compounds, wherein said polyol is sorbitol.

In certain embodiments, the invention relates to any one of the aforementioned compounds, wherein said polyol is inositol.

In certain embodiments, the invention relates to any one of the aforementioned compounds, wherein p is 2, 3, 4, 5, or 6.

In certain embodiments, the invention relates to any one of the aforementioned compounds, wherein p is 2-100 inclusive. In certain embodiments, the invention relates to any one of the aforementioned compounds, wherein p is 2-50 inclusive. In certain embodiments, the invention relates to any one of the aforementioned compounds, wherein p is 2-10 inclusive.

In certain embodiments, the invention relates to any one of the aforementioned compounds, wherein p is 2. In certain embodiments, the invention relates to any one of the aforementioned compounds, wherein p is 3. In certain embodiments, the invention relates to any one of the aforementioned compounds, wherein p is 4. In certain embodiments, the invention relates to any one of the aforementioned compounds, wherein p is 5. In certain embodiments, the invention relates to any one of the aforementioned compounds, wherein p is 6.

It has been discovered that at least certain of the compounds of the invention have desirable physiological attributes of niacin, with reduced undesirable physiological side effects of niacin. For example, compounds of the invention have the ability to modulate at least one lipid in a desirable fashion, without restrictive side effects, or without the degree of restrictive side effects, characteristic of niacin.

Additionally, it has been discovered that at least certain of the compounds of the invention do not appear to engage the high-affinity niacin receptor GPR109A in a manner similar to niacin. GPR109A, also referred to as PUMA-G and HM74A, is a member of the nicotinic acid receptor family of G protein-coupled redeptors (GPCRs). Wise A et al. (2003) *J Biol Chem* 278:99-74; Soga T et al. (2003) *Biochem Biophys Res Comm* 303:364-9. In GPR109A knockout mice, the effects of niacin on both lipids and flushing are eliminated. The flushing effect, but not the lipid modifying effects, of niacin has been ascribed to GPR109A activation of ERK 1/2 MAP kinase, mediated by arrestin beta 1 (beta (β)-arrestin). In arrestin beta 1 knockout mice, niacin's effect on flushing has been reported to be greatly reduced while the lipid modifying effects are maintained. Walters R W et al. (2009) *J Clin Invest* 119:1312-21. Significantly, at least certain of the compounds of the invention have greatly reduced ability to induce recruitment of β-arrestin to the membrane of cells expressing GPR109A, have greatly reduced flushing effect compared to niacin, yet maintain clinically significant desirable lipid-modifying effects.

Many of the compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Exemplary pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Certain compounds of the invention and their salts may exist in more than one crystal form and the present invention includes each crystal form and mixtures thereof.

Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of the invention and mixtures thereof.

Certain compounds of the invention may exist in different tautomeric forms or as different geometric isomers, and the present invention includes each tautomer and/or geometric isomer of compounds of the invention and mixtures thereof.

Certain compounds of the invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the invention and mixtures thereof.

Certain compounds of the invention may exist in zwitterionic form and the present invention includes each zwitterionic form of compounds of the invention and mixtures thereof.

The present invention also includes prodrugs. As used herein the term "prodrug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a prodrug would be a compound of the present invention wherein it is administered as an ester (the "prodrug") to facilitate transmittal across a cell membrane where water solubility is not beneficial, but then it is metabolically hydrolyzed to the carboxylic acid once inside the cell where water solubility is beneficial. Pro-drugs have many useful properties. For example, a prodrug may be more water soluble than the ultimate drug, thereby facilitating intravenous administration of the drug. A prodrug may also have a higher level of oral bioavailability than the ultimate drug. After administration, the prodrug is enzymatically or chemically cleaved to deliver the ultimate drug in the blood or tissue.

Exemplary prodrugs upon cleavage release the corresponding free acid, and such hydrolyzable ester-forming residues of the compounds of this invention include but are not limited to carboxylic acid substituents (e.g., —C(O)$_2$H or a moiety that contains a carboxylic acid) wherein the free hydrogen is replaced by ($C_1$-$C_4$)alkyl, ($C_2$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$)alkyl.

Other exemplary prodrugs release an alcohol or amine of a compound of the invention wherein the free hydrogen of a hydroxyl or amine substituent is replaced by ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyl-oxymethyl, N—($C_1$-$C_6$)alkoxycarbonylamino-methyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O($C_1$-$C_6$)alkyl)$_2$ or glycosyl (the radical resulting from detachment of the hydroxyl of the hemiacetal of a carbohydrate).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2$^{nd}$* ed.; Wiley: New York, 1991). Protected forms of the inventive compounds are included within the scope of this invention.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (C(=O)) is converted to a diether (C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRC(=O)R) or a urethane (—NRC(=O)OR), for example, as: a methyl amide (—NHC(=O)CH$_3$); a benzyloxy amide (—NHC(=O)OCH$_2$C$_6$H$_5$NHCbz); as a t-butoxy amide (—NHC=(=O)OC(CH$_3$)$_3$, —NHBoc); a 2-biphenyl-2-propoxy amide (—NHC(=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; or an acetamidomethyl ether (—SCH$_2$NHC(=O)CH$_3$).

Pharmaceutical Compositions

The invention provides pharmaceutical compositions comprising one or more of the above-referenced compounds. In one aspect, the present invention provides pharmaceutically acceptable compositions which comprise a therapeutically effective amount of one or more of the compounds described above, formulated together with one or more pharmaceutically acceptable carriers (additives) and/or diluents.

Alternatively or in addition, the invention provides pharmaceutical compositions characterized by having at least one desired therapeutic effect of niacin and a reduction or absence of at least one undesirable side effect of niacin.

In one aspect, the invention provides a pharmaceutical composition, comprising a niacin analog or a pharmaceutically acceptable salt thereof, and at least one pharmaceutically acceptable excipient; wherein said composition is formulated for oral administration; the niacin analog when administered orally to a human reduces a serum or plasma level of at least one lipid selected from the group consisting of total cholesterol, low-density lipoprotein (LDL) cholesterol, triglycerides, and lipoprotein (a); and oral administration of the composition is characterized by reduced flushing and reduced hepatocellular damage, as compared to administration of an equimolar oral dose of niacin.

A "niacin analog" as used herein is a structural analog of niacin, other than niacin (nicotinic acid), that, when administered orally to a subject, has at least one lipid-modulating effect that is characteristic of orally administered niacin. A niacin analog has a structure similar to that of niacin, but differing from niacin in respect of at least one atom, functional group, substituent, or substructure, which are replaced with other atoms, groups, substituents, or substructures. Niacin analogs of the invention specifically exclude timed-, sustained-, and extended-release formulations of niacin, including niacin formulated together with a polymer, such as polyethylene glycol or hydroxypropyl methylcellulose (hypromellose).

In one embodiment, the niacin analog is a pyridine-containing compound.

In one embodiment, the niacin analog is not

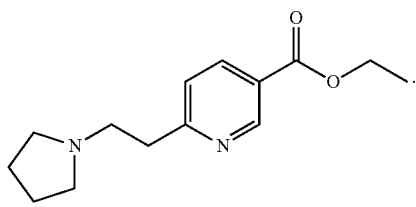 [SMILES: CCOC(=O)c1ccc(CCN2CCCC2)nc1 ; "."]

In one embodiment, the niacin analog specifically excludes 6-[2-(pyrrolidin-1-yl)ethyl]pyridine and 4-pyridin-3-yl-but-3-enoic acid disclosed in US Patent Application Publication No. US 2009/0312355 A1.

In one embodiment, the niacin analog specifically excludes any one or more of

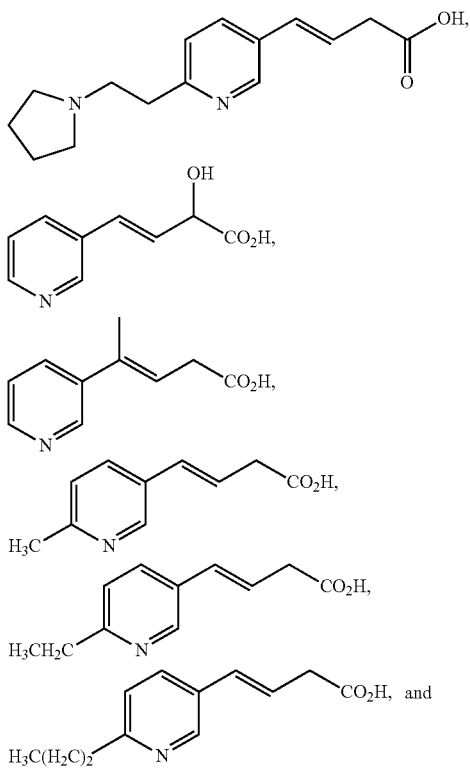

In one embodiment, the niacin analog specifically excludes a compound represented by structure A, or a pharmaceutically acceptable salt thereof:

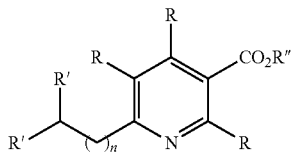

wherein

R represents independently for each occurrence H, alkyl, alkenyl, alkynyl, aryl, heteroaryl, aralkyl, heteroaralkyl, fluoride, chloride, bromide, iodide, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amino, alkylamino, arylamino, heteroarylamino, aralkylamino, heteroaralkylamino, alkenylamino, alkynylamino, formylamino, acylamino, carboxylate, alkyloxycarbonyl, aryloxycarbonyl, heteroaryloxycarbonyl, aralkyloxycarbonyl, heteroaralkyloxycarbonyl, carboxamido, alkylaminocarbonyl, arylaminocarbonyl, heteroarylaminocarbonyl, aralkylaminocarbonyl, or heteroaralkylaminocarbonyl;

R' represents independently for each occurrence H, alkyl, alkenyl, alkynyl, aryl, heteroaryl, aralkyl, heteroaralkyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, formyl, acyl, amino, alkylamino, arylamino, heteroarylamino, aralkylamino, heteroaralkylamino, alkenylamino, alkynylamino, formylamino, acylamino, alkyloxycarbonyl, aryloxycarbonyl, heteroaryloxycarbonyl, aralkyloxycarbonyl, heteroaralkyloxycarbonyl, alkylaminocarbonyl, arylaminocarbonyl, heteroarylaminocarbonyl, aralkylaminocarbonyl, or heteroaralkylaminocarbonyl; or the two instances of R' taken together represent —$(CH_2)_2$—, —$(CH_2)_3$—, —$(CH_2)_4$—, —$(CH_2)_5$—, or —$(CH_2)_6$—;

R" represents independently for each occurrence H, alkyl, alkenyl, alkynyl, aryl, heteroaryl, aralkyl, or heteroaralkyl; and n is 1, 2, 3, or 4.

The niacin analog, when administered orally to a human, reduces a serum or plasma level of at least one lipid selected from the group consisting of total cholesterol, low-density lipoprotein (LDL) cholesterol, triglycerides, and lipoprotein (a). The niacin analog is said to reduce a serum or plasma level of at least one lipid when such serum or plasma level is reduced by a measurable amount as compared to a pre-treatment, baseline, or control level. In one embodiment, the niacin analog is said to reduce a serum or plasma level of at least one lipid when such serum or plasma level is reduced by at least 5 percent of the pre-treatment, baseline, or control level; that is, the serum or plasma level is reduced to no more than 95 percent of the pre-treatment, baseline, or control level. In one embodiment, the niacin analog is said to reduce a serum or plasma level of at least one lipid when such serum or plasma level is reduced by at least 10 percent of the pre-treatment, baseline or control level. In one embodiment, the niacin analog is said to reduce a serum or plasma level of at least one lipid when such serum or plasma level is reduced by at least 15 percent of the pretreatment, baseline or control level. In one embodiment, the niacin analog is said to reduce a serum or plasma level of at least one lipid when such serum or plasma level is reduced by at least 20 percent of the pre-treatment, baseline or control level.

As used herein, "flushing" refers to objective cutaneous vasodilation, frequently accompanied by redness and/or a subjective experience of a warm feeling in the skin, the latter with or without itching. Flushing can be measured objectively using objective measurements such as Doppler capillary blood flow measurements. Alternatively or in addition, flushing can be measured using a so-called visual analog scale (VAS), which can be either observer-based or subject-based. The VAS typically involves scoring a sign or symptom on a scale ranging from zero (0) to ten (10), where zero corresponds to complete absence of the sign or symptom being scored, and ten corresponds to an unbearable or maximum amount or degree of the sign or symptom being scored.

As used herein, "hepatocellular damage" refers to toxic injury to liver parenchymal cells. Hepatocellular damage can be assessed using any suitable method. In one embodiment, hepatocellular damage is assessed by measuring one or more serum liver enzymes. In one embodiment, one such liver enzyme is aspartate aminotransferase (AST, also referred to as SGOT). In one embodiment, one such liver enzyme is alanine aminotransferase (ALT, also referred to as SGPT). Serum levels of AST and ALT are commonly measured in clinical practice, and it is not necessary to describe methods for their measurement here. Normal serum levels both of AST and ALT are generally 0-35 U/L. In contrast to ALT, which is found primarily in the liver, AST is also found in other tissues, including heart, skeletal muscle, kidney, and brain, and is thus somewhat less specific as an indicator of liver dysfunction. Although elevated serum levels of AST or ALT may be observed in a variety of nonhepatic conditions, including myocardial infarction, these conditions are usually readily distinguished clinically from liver disease. In liver disease, elevations of serum AST and ALT reflect hepatic necrosis, a severe form of hepatocellular damage.

Oral administration of the composition is characterized by reduced flushing and reduced hepatocellular damage, as compared to administration of an equimolar oral dose of niacin. In this context, flushing is said to be reduced when it is reduced by a measurable amount or degree as compared to a corresponding degree of flushing associated with administration of an equimolar oral dose of niacin. In one embodiment, flushing is said to be reduced when the maximum degree or amount of flushing is reduced by a measurable degree or amount as compared to the maximum degree or amount of flushing associated with administration of an equimolar oral dose of niacin.

In one embodiment, flushing is said to be reduced when Doppler capillary blood flow in relevant tissue is reduced by at least 2 percent as compared to Doppler capillary blood flow in corresponding relevant tissue associated with administration of an equimolar oral dose of niacin; i.e., the flow is reduced to no more than 98 percent of the Doppler capillary blood flow in corresponding relevant tissue associated with administration of an equimolar oral dose of niacin. In one embodiment, flushing is said to be reduced when Doppler capillary blood flow in relevant tissue is reduced by at least 5 percent as compared to Doppler capillary blood flow in corresponding relevant tissue associated with administration of an equimolar oral dose of niacin. In one embodiment, flushing is said to be reduced when Doppler capillary blood flow in relevant tissue is reduced by at least 10 percent as compared to Doppler capillary blood flow in corresponding relevant tissue associated with administration of an equimolar oral dose of niacin.

In one embodiment, flushing is said to be reduced when VAS score for relevant tissue is reduced by at least one (1) (on a scale from 0 to 10) as compared to VAS score for corresponding relevant tissue associated with administration of an equimolar oral dose of niacin; i.e., the VAS score reduced to no more than one less than the VAS score for corresponding relevant tissue associated with administration of an equimolar oral dose of niacin. For example, in one such an embodiment, flushing is said to be reduced when the maximum VAS score is 5 whereas the maximum VAS score for corresponding relevant tissue associated with administration of an equimolar oral dose of niacin is 6-10.

Of course, any of the foregoing comparisons can, advantageously, be made on a population basis. For example, mean or median values of AST, ALT, or VAS score can be compared. Likewise, mean or median values of maximum AST, maximum ALT, or maximum VAS score can be compared.

Comparison is made to an equimolar oral dose of niacin. An equimolar oral dose of niacin refers to an equimolar oral dose of niacin in any form, including, for example immediate-, timed-, sustained-, and extended-release formulations of niacin. In one embodiment, an equimolar oral dose is formulated in an analogous fashion, e.g., in tablet form wherein each individual tablet is comprised of the same or essentially the same molar amount of active agent. Thus, for example, comparison can be made, in one embodiment, between oral doses given as single tablets, each tablet containing 8.2 mmol of active agent (e.g., 1 g of niacin). As an alternative example, comparison can be made, in another embodiment, between oral doses given as two single tablets, each tablet containing 4.1 mmol of active agent (e.g., 0.5 g of niacin).

Except as may be indicated otherwise herein, all pharmacokinetic comparisons to "niacin" are comparisons to so-called immediate-release formulation of niacin.

In certain embodiments, the invention relates to any one of the aforementioned compositions, wherein peak serum or plasma concentration ($C_{max}$) for the niacin analog is 40 percent or less of $C_{max}$ for the equimolar oral dose of niacin. In one embodiment, peak serum or plasma concentration ($C_{max}$) for the niacin analog is 35 percent or less of $C_{max}$ for the equimolar oral dose of niacin. In one embodiment, peak serum or plasma concentration ($C_{max}$) for the niacin analog is 30 percent or less of $C_{max}$ for the equimolar oral dose of niacin. In one embodiment, peak serum or plasma concentration ($C_{max}$) for the niacin analog is 25 percent or less of $C_{max}$ for the equimolar oral dose of niacin. In one embodiment, peak serum or plasma concentration ($C_{max}$) for the niacin analog is 20 percent or less of $C_{max}$ for the equimolar oral dose of niacin. In one embodiment, peak serum or plasma concentration ($C_{max}$) for the niacin analog is 15 percent or less of $C_{max}$ for the equimolar oral dose of niacin. In one embodiment, peak serum or plasma concentration ($C_{max}$) for the niacin analog is 10 percent or less of $C_{max}$ for the equimolar oral dose of niacin. In one embodiment, peak serum or plasma concentration ($C_{max}$) for the niacin analog is 5 percent or less of $C_{max}$ for the equimolar oral dose of niacin. In one embodiment, peak serum or plasma concentration ($C_{max}$) for the niacin analog is 1 percent or less of $C_{max}$ for the equimolar oral dose of niacin. For each of the foregoing embodiments, it is to be understood that comparison is made with an immediate release formulation of niacin. Methods useful for measuring the concentration are disclosed in detail hereinbelow.

In certain embodiments, the invention relates to any one of the aforementioned compositions, wherein peak serum or plasma concentration ($C_{max}$) for the compound is 1 to 40 percent of $C_{max}$ for the equimolar oral dose of niacin. In one embodiment, peak serum or plasma concentration ($C_{max}$) for the compound is 1 to 35 percent of $C_{max}$ for the equimolar oral dose of niacin. In one embodiment, peak serum or plasma concentration ($C_{max}$) for the compound is 1 to 30 percent of $C_{max}$ for the equimolar oral dose of niacin. In one embodiment, peak serum or plasma concentration ($C_{max}$) for the compound is 1 to 25 percent of $C_{max}$ for the equimolar oral dose of niacin. In one embodiment, peak serum or plasma concentration ($C_{max}$) for the compound is 1 to 20 percent of $C_{max}$ for the equimolar oral dose of niacin. In one embodiment, peak serum or plasma concentration ($C_{max}$) for the compound is 1 to 15 percent of $C_{max}$ for the equimolar oral dose of niacin. In one embodiment, peak serum or plasma concentration ($C_{max}$) for the compound is 1 to 10 percent of $C_{max}$ for the equimolar oral dose of niacin. For each of the foregoing embodiments, it is to be understood that comparison is made with an immediate release formulation of niacin. Methods useful for measuring the concentration are disclosed in detail hereinbelow.

In certain embodiments, the invention relates to any one of the aforementioned compositions, wherein the ratio of peak serum or plasma concentration ($C_{max}$) to area under the curve at 24 hours ($AUC_{0-24}$) (i.e., the ratio $C_{max}/AUC_{0-24}$) for the niacin analog is 0.35 $h^{-1}$ or less. In one embodiment, the ratio of peak concentration to area under the curve at 24 hours ($C_{max}/AUC_{0-24}$) for the niacin analog is 0.30 $h^{-1}$ or less. In one embodiment, the ratio of peak concentration to area under the curve at 24 hours ($C_{max}/AUC_{0-24}$) for the niacin analog is 0.25 $h^{-1}$ or less. In one embodiment, the ratio of peak concentration to area under the curve at 24 hours ($C_{max}/AUC_{0-24}$) for the niacin analog is 0.20 $h^{-1}$ or less. In one embodiment, the ratio of peak concentration to area under the curve at 24 hours ($C_{max}/AUC_{0-24}$) for the niacin analog is 0.15 $h^{-1}$ or less. In one embodiment, the ratio of peak concentration to area under the curve at 24 hours ($C_{max}/AUC_{0-24}$) for the niacin analog is 0.10 $h^{-1}$ or less. In one embodiment, the ratio of peak concentration to area under the curve at 24 hours ($C_{max}/AUC_{0-24}$) for the niacin analog is 0.05 $h^{-1}$ or less. In one embodiment, the ratio of peak concentration to area under the curve at 24 hours ($C_{max}/AUC_{0-24}$) for the niacin analog is 0.01 $h^{-1}$ or less.

In certain embodiments, the invention relates to any one of the aforementioned compositions, wherein the ratio of peak serum or plasma concentration ($C_{max}$) to area under the curve at 24 hours ($AUC_{0-24}$) (i.e., the ratio $C_{max}/AUC_{0-24}$) for the compound is 0.10 $h^{-1}$ to 0.35 $h^{-1}$. In one embodiment, the ratio of peak concentration to area under the curve at 24 hours ($C_{max}/AUC_{0-24}$) for the compound is 0.10 $h^{-1}$ to 0.30 $h^{-1}$. In one embodiment, the ratio of peak concentration to area under the curve at 24 hours ($C_{max}/AUC_{0-24}$) for the compound is 0.10 $h^{-1}$ to 0.25 $h^{-1}$. In one embodiment, the ratio of peak concentration to area under the curve at 24 hours ($C_{max}/AUC_{0-24}$) for the compound is 0.10 $h^{-1}$ to 0.20 $h^{-1}$.

In certain embodiments, the invention relates to any one of the aforementioned compositions, wherein the time to peak serum or plasma concentration ($t_{max}$) for the niacin analog is in the range of 30 minutes to 5 hours. In one embodiment, the time to peak concentration ($t_{max}$) for the niacin analog is in the range of 1 to 5 hours. In one embodiment, the time to peak concentration ($t_{max}$) for the niacin analog is in the range of 1 to 4 hours. In one embodiment, the time to peak concentration ($t_{max}$) for the niacin analog is in the range of 1 to 3 hours. In one embodiment, the time to peak concentration ($t_{max}$) for the niacin analog is in the range of 1 to 2 hours.

In certain embodiments, the invention relates to any one of the aforementioned compositions, wherein the niacin analog has an $EC_{50}$ for β-arrestin-mediated GPR109A function which is at least 10 times greater than the $EC_{50}$ of niacin for β-arrestin-mediated GPR109A function. $EC_{50}$ refers to the concentration at which a particular effect achieves 50 percent of its maximum. β-arrestin-mediated GPR109A function is described elsewhere herein. In one embodiment, the niacin analog has an $EC_{50}$ for β-arrestin-mediated GPR109A function which is at least 20 times greater than the $EC_{50}$ of niacin for β-arrestin-mediated GPR109A function. In one embodiment, the niacin analog has an $EC_{50}$ for β-arrestin-mediated GPR109A function which is at least 30 times greater than the $EC_{50}$ of niacin for β-arrestin-mediated GPR109A function. In one embodiment, the niacin analog has an $EC_{50}$ for β-arrestin-mediated GPR109A function which is at least 40 times greater than the $EC_{50}$ of niacin for β-arrestin-mediated GPR109A function. In one embodiment, the niacin analog has an $EC_{50}$ for β-arrestin-mediated GPR109A function which is at least 50 times greater than the $EC_{50}$ of niacin for β-arrestin-mediated GPR109A function. In one embodiment, the niacin analog has an $EC_{50}$ for β-arrestin-mediated GPR109A function which is at least 100 times greater than the $EC_{50}$ of niacin for β-arrestin-mediated GPR109A function.

In certain embodiments, the invention relates to any one of the aforementioned compositions, wherein the niacin analog, when administered orally to a human, also increases a serum or plasma level of high-density lipoprotein (HDL) cholesterol. The serum or plasma level of HDL cholesterol increases by at least a measurable amount compared to a pre-treatment, baseline, or control level. For example, in one embodiment, serum or plasma level of HDL cholesterol increases by at least 5 percent compared to a pre-treatment, baseline, or control level. In one embodiment, serum or plasma level of HDL cholesterol increases by at least 10 percent compared to a pre-treatment, baseline, or control level. In one embodiment, serum or plasma level of HDL cholesterol increases by at least 15 percent compared to a pre-treatment, baseline, or control level. In one embodiment, serum or plasma level of HDL cholesterol increases by at least 20 percent compared to a pre-treatment, baseline, or control level. In one embodiment, serum or plasma level of HDL cholesterol increases by at least 25 percent compared to a pre-treatment, baseline, or control level.

In certain embodiments, the invention relates to any one of the aforementioned compositions, wherein the niacin analog, when administered orally to a human, induces substantially no increase in serum levels of aspartate aminotransferase (AST), alanine aminotransferase (ALT), or both. In one embodiment, "substantially no increase" in this context means less than a 20 percent increase over a pre-treatment, baseline, or control level. In one embodiment, "substantially no increase" means less than a 10 percent increase over a pre-treatment, baseline, or control level.

In certain embodiments, the invention relates to any one of the aforementioned compositions, wherein the niacin analog, when administered orally to a human, induces substantially no increase in serum levels of uric acid, glucose, or both. Normal serum levels of uric acid are 1.5-8.0 mg/dL. In one embodiment, "substantially no increase in serum level of uric acid" means less than a 10 percent increase over a pre-treatment, baseline, or control level. Normal fasting plasma levels of glucose are ca. 75-115 mg/dL. Normal random (2 h postprandial) plasma levels of glucose are ca. <140 mg/dL. In one embodiment, "substantially no increase in serum level of glucose" means less than a 20 percent increase over a pre-treatment, baseline, or control level. In one embodiment, "substantially no increase in serum level of glucose" means less than a 15 percent increase over a pre-treatment, baseline, or control level. In one embodiment, "substantially no increase in serum level of glucose" means less than a 10 percent increase over a pre-treatment, baseline, or control level.

In certain embodiments, the invention relates to any one of the aforementioned compositions, wherein the niacin analog is represented by structure I:

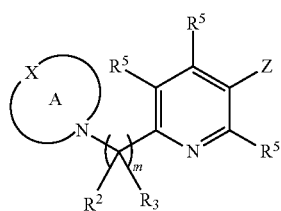

I wherein
A is a heterocyclyl or heteroaryl, optionally deuterated, containing from 5 to 12 ring atoms, including X and N, which is optionally substituted with 1-3 substituents, independently selected from the group consisting of alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;
X is O, S, N or $N(R^6)$;
Z is

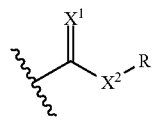

or an isostere of a carboxyl group;
$X^1$ is O or S;
$X^2$ is O or S;
R is hydrogen, alkyl, haloalkyl, alkenyl, alkynyl, carbocyclyl, heterocyclyl, heterocyclylalkyl, aryl, aralkyl, heteroaryl, heteroaralkyl, fused bicyclyl, carboxyalkyl, or arylalkenylaryl;

$R^2$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;

$R^3$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;

$R^5$ is selected independently for each occurrence from the group consisting of hydrogen, alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;

$R^6$ is hydrogen or lower alkyl; and
m is 1, 2, 3, or 4.

In certain embodiments, the invention relates to any one of the aforementioned compositions, wherein A represents heterocyclyl.

In certain embodiments, the invention relates to any one of the aforementioned compositions, wherein A represents heteroaryl.

In certain embodiments, the invention relates to any one of the aforementioned compositions, wherein A is a radical of a monocyclic ring having 5, 6 or 7 ring atoms.

In certain embodiments, the invention relates to any one of the aforementioned compositions, wherein A is a radical of a bicyclic ring having 9, 10, 11 or 12 ring atoms.

In certain embodiments, the invention relates to any one of the aforementioned compositions, wherein X is O.

In certain embodiments, the invention relates to any one of the aforementioned compositions, wherein X is S.

In certain embodiments, the invention relates to any one of the aforementioned compositions, wherein X is N.

In certain embodiments, the invention relates to any one of the aforementioned compositions, wherein X is $N(R^6)$.

In certain embodiments, the invention relates to any one of the aforementioned compositions, wherein X is N(H).

In certain embodiments, the invention relates to any one of the aforementioned compositions, wherein A is pyrrolidinyl, imidazolidinyl, thiazolidinyl, isothiazolidinyl, oxazolidinyl, oxadiazolidinyl, piperidinyl, piperazinyl, thiomorpholinyl or morpholinyl.

In certain embodiments, the invention relates to any one of the aforementioned compositions, wherein A is imidazolyl, pyrazolyl, isoxoazolyl, oxazolyl, isothiazolyl, thiazolyl, oxinyl, furazanyl, oxadiazolyl, thiadiazolyl, triazolyl, dithiazolyl, diazinyl, oxazinyl, thiazinyl, triazinyl, tetrazinyl, diazepinyl or thiazepinyl.

In certain embodiments, the invention relates to any one of the aforementioned compositions, wherein A is substituted with 1-3 substituents independently selected from the group consisting of lower alkyl, halogen, nitro, cyano, sulfonic acid, hydroxyl, alkoxyl, thiol, alkylthio, formyl, acyl, formyloxy, acyloxy, formylthio, acylthio, amine, alkylamine, formylamine, acylamine and carboxyl.

In certain embodiments, the invention relates to any one of the aforementioned compositions, wherein A is substituted with 1 substituent independently selected from the group consisting of lower alkyl, halogen, nitro, cyano, sulfonic acid, hydroxyl, alkoxyl, thiol, alkylthio, formyl, acyl, formyloxy, acyloxy, formylthio, acylthio, amine, alkylamine, formylamine, acylamine and carboxyl.

In certain embodiments, the invention relates to any one of the aforementioned compositions, wherein A is not substituted.

In certain embodiments, the invention relates to any one of the aforementioned compositions, wherein $R^2$ is hydrogen or lower alkyl.

In certain embodiments, the invention relates to any one of the aforementioned compositions, wherein $R^2$ is hydrogen.

In certain embodiments, the invention relates to any one of the aforementioned compositions, wherein $R^3$ is hydrogen or lower alkyl.

In certain embodiments, the invention relates to any one of the aforementioned compositions, wherein $R^3$ is hydrogen.

In certain embodiments, the invention relates to any one of the aforementioned compositions, wherein $R^2$ is hydrogen; and $R^3$ is lower alkyl.

In certain embodiments, the invention relates to any one of the aforementioned compositions, wherein $R^2$ is lower alkyl; and $R^3$ is hydrogen.

In certain embodiments, the invention relates to any one of the aforementioned compositions, wherein $R^2$ is hydrogen; and $R^3$ is hydrogen.

In certain embodiments, the invention relates to any one of the aforementioned compositions, wherein m is 1.

In certain embodiments, the invention relates to any one of the aforementioned compositions, wherein m is 2.

In certain embodiments, the invention relates to any one of the aforementioned compositions, wherein m is 3.

In certain embodiments, the invention relates to any one of the aforementioned compositions, wherein m is 4.

In certain embodiments, the invention relates to any one of the aforementioned compositions, wherein $R^5$ is selected independently for each occurrence from the group consisting of hydrogen, lower alkyl, halogen, nitro, cyano, sulfonic acid, hydroxyl, alkoxyl, thiol, alkylthio, formyl, acyl, formyloxy, acyloxy, formylthio, acylthio, amine, alkylamine, formylamine, acylamine and carboxyl.

In certain embodiments, the invention relates to any one of the aforementioned compositions, wherein $R^5$ is hydrogen.

In certain embodiments, the invention relates to any one of the aforementioned compositions, wherein Z is carboxyl.

In certain embodiments, the invention relates to any one of the aforementioned compositions, wherein Z is a carboxyl isostere.

In certain embodiments, the invention relates to any one of the aforementioned compositions, wherein Z is tetrazolyl, oxazolidinonyl, sulfonic acid, sulfinic acid, acylsulphonamide, phosphonic acid, phosphinic acid, hydantoin, pyrrolidione, 3-isoxazolyl, or boronic acid.

In certain embodiments, the invention relates to any one of the aforementioned compositions, wherein Z is

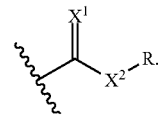

In certain embodiments, the invention relates to any one of the aforementioned compositions, wherein $X^1$ is O.

In certain embodiments, the invention relates to any one of the aforementioned compositions, wherein $X^1$ is S.

In certain embodiments, the invention relates to any one of the aforementioned compositions, wherein $X^2$ is O.

In certain embodiments, the invention relates to any one of the aforementioned compositions, wherein $X^2$ is S.

In certain embodiments, the invention relates to any one of the aforementioned compositions, wherein $X^1$ is O; and $X^2$ is O.

In certain embodiments, the invention relates to any one of the aforementioned compositions, wherein R is lower alkyl.

In certain embodiments, the invention relates to any one of the aforementioned compositions, wherein R is hydrogen.

In certain embodiments, the invention relates to any one of the aforementioned compositions, wherein R is

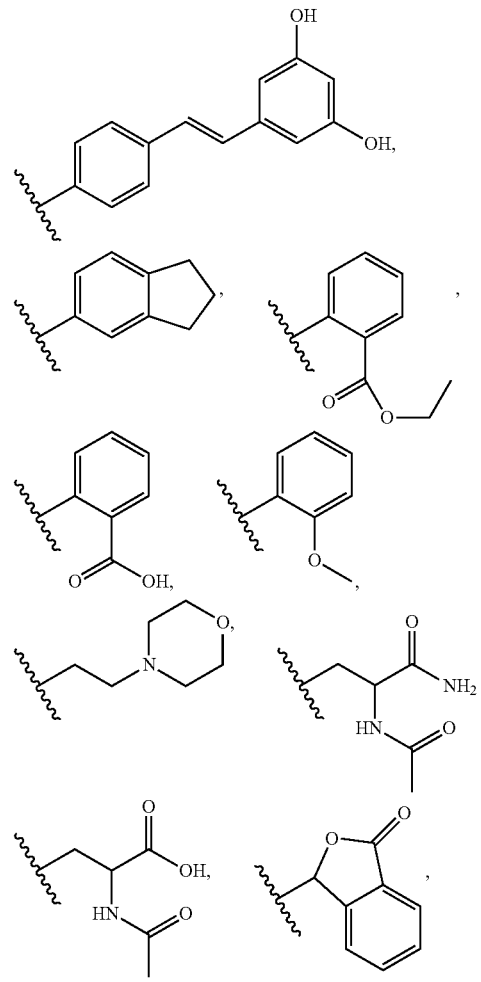

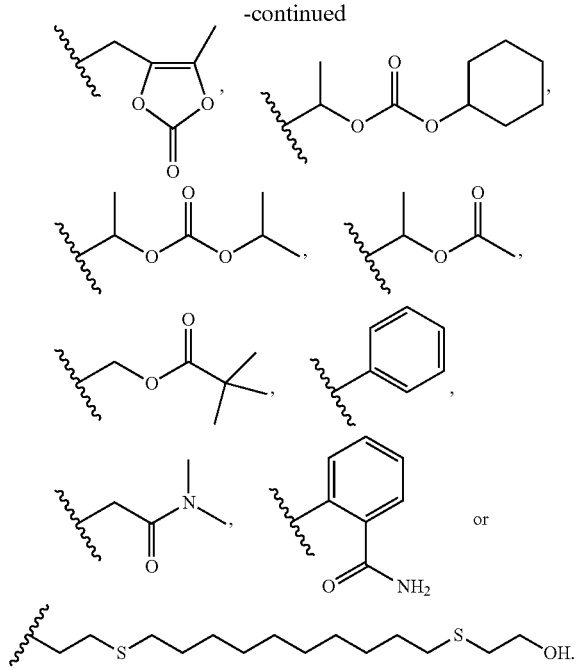

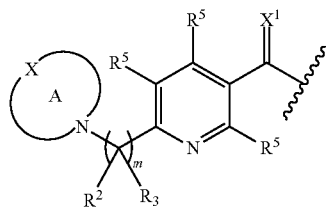

In certain embodiments, the invention relates to any one of the aforementioned compositions, wherein R represents an aliphatic group which is hydrolyzed to carboxyl under physiological conditions.

In certain embodiments, the invention relates to any one of the aforementioned compositions, wherein the niacin analog is a compound represented by structure II, or a pharmaceutically acceptable salt thereof, $$W\text{---}(R^1)_p \qquad \qquad II$$

wherein, independently for each occurrence,
W is a polyol or polythiol;
p is 2-500 inclusive;
$R^1$ is

and is either appended to the polyol through an oxygen atom of the polyol or is appended to the polythiol through a sulfur atom of the polythiol;

A is a heterocyclyl or heteroaryl, optionally deuterated, containing from 5 to 12 ring atoms, including X and N, which is optionally substituted with 1-3 substituents, independently selected from the group consisting of alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;

X is O, S, N or $N(R^6)$;
$X^1$ is O or S;
$R^2$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;
$R^3$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;
$R^5$ is selected independently for each occurrence from the group consisting of hydrogen, alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;
$R^6$ is hydrogen or lower alkyl; and
m is 1, 2, 3, or 4.

In certain embodiments, the invention relates to any one of the aforementioned compositions, wherein W is a polythiol.

In certain embodiments, the invention relates to any one of the aforementioned compositions, wherein W is a polyol.

In certain embodiments, the invention relates to any one of the aforementioned compositions, wherein said polyol is a carbohydrate.

In certain embodiments, the invention relates to any one of the aforementioned compositions, wherein said polyol is maltitol, sorbitol, xylitol or isomalt.

In certain embodiments, the invention relates to any one of the aforementioned compositions, wherein said polyol is sorbitol.

In certain embodiments, the invention relates to any one of the aforementioned compositions, wherein said polyol is inositol.

In certain embodiments, the invention relates to any one of the aforementioned compositions, wherein p is 2, 3, 4, 5, or 6.

In certain embodiments, the invention relates to any one of the aforementioned compositions, wherein p is 2-100 inclusive. In certain embodiments, the invention relates to any one of the aforementioned compositions, wherein p is 2-50 inclusive. In certain embodiments, the invention relates to any one of the aforementioned compositions, wherein p is 2-10 inclusive.

In certain embodiments, the invention relates to any one of the aforementioned compositions, wherein p is 2. In certain embodiments, the invention relates to any one of the aforementioned compositions, wherein p is 3. In certain embodiments, the invention relates to any one of the aforementioned compositions, wherein p is 4. In certain embodiments, the invention relates to any one of the aforementioned compositions, wherein p is 5. In certain embodiments, the invention relates to any one of the aforementioned compositions, wherein p is 6.

In another aspect, the agents of the invention can be administered as such, or administered in mixtures with pharmaceutically acceptable carriers and can also be administered in conjunction with other agents. Conjunctive therapy thus includes sequential, simultaneous and separate, or co-administration of one or more compound of the invention, wherein the therapeutic effects of the first administered has not entirely disappeared when the subsequent compound is administered. In other words, the terms "co-administration" and "co-administering," as used herein, refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, capsules, boluses, powders, granules, pastes for application to the tongue; (2) parenteral administration, for example, by intravenous, intramuscular, intraperitoneal, subcutaneous, or epidural injection or infusion as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "therapeutically effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. See, for example, Berge et al. (1977) "Pharmaceutical Salts", *J. Pharm. Sci.* 66:1-19.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled-release agents, such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In some cases, in order to prolong the effect of a drug, it is desirable to slow the absorption of the drug from subcutaneous or intramuscular injection. This result may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers, such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, administration by injection, infusion or inhalation; topical by lotion or ointment; and rectal by suppositories.

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated effects, will range from about 0.0001 to about 100 mg per kilogram of body weight per day.

Oral administration in humans is specifically contemplated by the invention. Oral dosing in adult humans is typically on the order of 0.05 grams (50 mg) to 10 grams per day, given as a single dose or in divided doses. In one embodiment, oral dosing to adult humans is 0.5 grams (500 mg) to 10 grams per day, given as a single dose or in divided doses. In one embodiment, oral dosing to adult humans is 0.5 to 8 grams per day, given as a single dose or in divided doses. In one embodiment, oral dosing to adult humans is 0.5 to 6 grams per day, given as a single dose or in divided doses. In one embodiment, oral dosing to adult humans is 0.5 to 4 grams per day, given as a single dose or in divided doses. In one embodiment, oral dosing to adult humans is 0.5 to 2 grams per day, given as a single dose or in divided doses. In one embodiment, oral dosing to adult humans is 0.5 to 1 gram per day, given as a single dose or in divided doses.

If desired, the effective daily dose of the active compound may be administered as two, three, four, five, six or more sub-doses administered separately at appropriate intervals throughout the day, optionally, in unit dosage forms. Exemplary dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The patient receiving this treatment is any animal in need, including primates, in particular humans, and other mammals, such as equines, cattle, swine and sheep; and poultry and pets in general.

The compound of the invention can be administered as such or in admixtures with pharmaceutically acceptable carriers and can also be administered in conjunction with at least one other active compound. Conjunctive therapy thus includes sequential, simultaneous and separate administration of the active compound in a way that the therapeutical effects of the first administered one is not entirely disappeared when the subsequent is administered.

Micelles.

Microemulsification technology improves bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, exemplary carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Polymers.

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Exemplary polymers are those having a molecular weight of from about 100 or 120 Daltons up to about 5,000 or 10,000 Daltons, and more preferably from about 300 Daltons to about 5,000 Daltons. In one embodiment, the polymer is polyethyleneglycol having a molecular weight of from about 100 to about 5,000 Daltons, and more preferably having a molecular weight of from about 300 to about 5,000 Daltons. In one embodiment, the polymer is polyethyleneglycol of 750 Daltons (PEG(750)). Polymers may also be defined by the number of monomers therein; an embodiment of the present invention utilizes polymers of at least about three monomers, such PEG polymers consisting of three monomers (approximately 150 Daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins.

Cyclodextrins are cyclic oligosaccharides, consisting of 6, 7 or 8 glucose units, designated by the Greek letters alpha, beta and gamma, respectively. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17-beta-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259; incorporated by reference) and Gramera, et al. (U.S. Pat. No. 3,459,731; incorporated by reference) describe electroneutral cyclodextrins. Other derivatives include cyclodextrins with cationic properties (Parmeter (II), U.S. Pat. No. 3,453,257; incorporated by reference), insoluble crosslinked cyclodextrins (Solms, U.S. Pat. No. 3,420,788; incorporated by reference), and cyclodextrins with anionic properties (Parmeter (III), U.S. Pat. No. 3,426,011; incorporated by reference). Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin (see, Parmeter (III), supra). Furthermore, sulfoalkyl ether cyclodextrin derivatives have been described by Stella, et al. (U.S. Pat. No. 5,134,127; incorporated by reference).

Liposomes.

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 μm in diameter; large unilamellar vesicles (LUVS) are typically larger than 0.05 μm. Oligolamellar large vesicles and multilamellar vesicles have multiple, usually concentric, membrane layers and are typically larger than 0.1 μm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the critical micelle concentration (CMC) of the surfactant and aids in micelle formation. Examples are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes useful in the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic DD, Liposomes from physics to applications, Elsevier Science Publishers BV, Amsterdam, 1993.

For example, liposomes useful in the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In one aspect of the present invention, the liposomes have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323.

Release Modifiers.

The release characteristics of a formulation of the present invention depend on the encapsulating material, the concentration of encapsulated drug, and the presence of release modifiers. For example, release can be manipulated to be pH dependent using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts, such as ammonium sulfate and ammonium chloride, organic acids, such as citric acid, benzoic acid, and ascorbic acid, inorganic bases, such as sodium carbonate, potassium carbonate, calcium carbonate, zinc carbonate, and zinc hydroxide, and organic bases, such as protamine sulfate, spermine, choline, ethanolamine, diethanolamine, and triethanolamine and surfactants, such as Tween® and Pluronic®. Pore forming agents which add microstructure to the matrices (i.e., water soluble compounds, such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

One aspect of the invention relates to a pharmaceutical composition, comprising a compound of the present invention or a pharmaceutically acceptable salt thereof; and a pharmaceutically acceptable excipient.

In certain embodiments, the present invention relates to any one of the aforementioned pharmaceutical compositions, wherein the pharmaceutical preparation has an $EC_{50}$ for reducing serum cholesterol, LDL and/or triglycerides which, in the average human patient population, is no more than 20 percent of the half maximal concentration of pharmaceutical preparation which would cause cutaneous vasodilation (flushing) in the average patient population.

In certain embodiments, the present invention relates to any one of the aforementioned pharmaceutical compositions, wherein the $EC_{50}$ for reducing serum cholesterol, LDL and/or triglycerides is no more than 1 percent of the half maximal concentration of pharmaceutical preparation which would cause cutaneous vasodilation (flushing) in the average patient population.

In certain embodiments, the present invention relates to any one of the aforementioned pharmaceutical compositions, wherein the pharmaceutical preparation has an $EC_{50}$ for reducing serum cholesterol, LDL and/or triglycerides which, in the average human patient population, is no more than 20 percent of the concentration of pharmaceutical preparation which would cause increases in serum levels of aspartate aminotransferase (AST) and alanine aminotransferase (ALT) requiring discontinuation of administration of the pharmaceutical preparation.

In certain embodiments, the present invention relates to any one of the aforementioned pharmaceutical compositions, wherein said composition is effective in reducing a serum lipid without causing treatment-limiting (i) hepatotoxicity and (ii) elevations in uric acid levels or glucose levels or both, following administration to said patient that would require such treatment to be discontinued when said composition is ingested by said patient once per day.

In certain embodiments, the present invention relates to any one of the aforementioned pharmaceutical compositions formulated in combination with a statin.

In certain embodiments, the present invention relates to any one of the aforementioned pharmaceutical compositions, wherein the statin is selected from the group consisting of atorvastatin, cerivastatin, fluvastatin, lovastatin, mevastatin, pitavastatin, pravastatin, rosuvastatin and simvastatin.

In certain embodiments, the present invention relates to any one of the aforementioned pharmaceutical compositions formulated in combination with at least one additional therapeutic agent selected from the group consisting of 11β HSD-1 inhibitors, 5HT transporter inhibitors, 5HT2c agonists, 5-LO or FLAP inhibitors, α-glucosidase inhibitors, ABCA1 enhancers, ACC inhibitors, AcylCoA:cholesterol O-acyltransferase inhibitors, acyl-estrogens, antidiabetic agents, anti-dyslipidemic agents, anti-hypertensive agents, anti-oxidants, Apo A1 mimetics, Apo A1 modulators, Apo E mimetics, apolipoprotein-B secretion/microsomal triglyceride transfer protein (apo-B/MTP) inhibitors, appetite suppressants, aspirin, β3 agonists, bile acid reabsorption inhibitors, bile acid sequestrants, bombesin agonists, BRS3 agonists, $CB_1$ antagonists/inverse agonists, CCK-A agonists, cholesterol absorption inhibitor, cholesterol transport inhibitors, cholesteryl ester transfer protein (CETP) inhibitors, CNTF, CNTF agonists/modulators, a combination of ezetimibe and simvastatin and/or atorvastatin, CSL-111, dehydroepiandrosterone, delipidated HDL, DGAT antisense oligos, DGAT1 inhibitors, DGAT2 inhibitors, dicarboxylate transporter inhibitors, dopamine agonists, DP receptor antagonists, ezetimibe, FAS inhibitors, fatty acid binding protein (FABP) inhibitors, fatty acid transporter inhibitors, fatty acid transporter protein (FATP) inhibitors, flush inhibitors, FXR receptor modulators, galanin receptor antagonists, gemcabene, ghrelin antagonists, ghrelin antibodies, GLP-1 agonists, glucagon-like peptide-1 receptor agonists, glucocorticoid agonists/antagonists, glucose transporter inhibitors, HDL mimetics, HMG CoA reductase inhibitor compounds, HMG-CoA synthetase inhibitors, hormone sensitive lipase antagonists, human agouti-related proteins (AGRP), $H_3$ antagonists/inverse agonists, inorganic cholesterol sequestrants, L-4f, lapaquistat, leptin agonists/modulators, leptins, lipase inhibitors, lipoprotein synthesis inhibitors, lorapoprant, low density lipoprotein receptor inducers or activators, Lp(a) reducers, LXR receptor agonists, lyn kinase inhibitor, Mc3r agonists, Mc4r agonists, MCH1R antagonists, MCH2R agonists/antagonists, melanin concentrating hormone antagonists, mGluR5 antagonists, microsomal triglyceride transport inhibitors, monoamine reuptake inhibitors, natural water soluble fibers, NE transporter inhibitors, neuromedin U receptor agonists, neuropeptide-Y antagonists, niacin or niacin receptor agonists, nicotinic acid, noradrenergic anorectic agents, NPY1 antagonists, NPY2 agonists, NPY4 agonists, NPY5 antagonists, non-steroidal anti-inflammatory drug (NSAID) agents, omega-3 fatty acids, opioid antagonists, orexin receptor antagonists, PDE inhibitors, phentermine, phosphate transporter inhibitors, phytopharm compound 57, plant stanols and/or fatty acid esters of plant stanols, platelet aggregation inhibitors, PPAR-α agonists, PPAR-δ agonists, PPAR-δ partial agonists, PPAR-γ agonists, probucol, renin angiotensin inhibitors, reversed-4F, SCD-1 inhibitors, serotonin reuptake inhibitors, SGLT2 inhibitors, squalene epoxidase inhibitors, squalene synthesis inhibitors, sterol biosynthesis inhibitors, sympathomimetic agonists, thyroid hormone β agonists, thyromimetic agents, topiramate, triglyceride synthesis inhibitors, UCP-1 activators, UCP-2 activators, UCP-3 activators, and urocortin binding protein antagonists.

In certain embodiments, the present invention relates to a pharmaceutical composition, comprising a compound of the present invention or a pharmaceutically acceptable salt thereof; niacin; and a pharmaceutically acceptable excipient.

In certain embodiments, the present invention relates to a pharmaceutical composition, comprising a compound of the present invention or a pharmaceutically acceptable salt thereof; niacin; a statin selected from the group consisting of atorvastatin, cerivastatin, fluvastatin, lovastatin, mevastatin, pitavastatin, pravastatin, rosuvastatin and simvastatin; and a pharmaceutically acceptable excipient.

In certain embodiments, the present invention relates to a pharmaceutical composition, comprising a compound of the present invention or a pharmaceutically acceptable salt thereof; a glitazone selected from the group consisting of troglitazone, rosiglitazone, and pioglitazone; and a pharmaceutically acceptable excipient.

In certain embodiments, the present invention relates to a pharmaceutical composition, comprising a compound of the present invention or a pharmaceutically acceptable salt thereof; niacin; a glitazone selected from the group consisting of troglitazone, rosiglitazone, and pioglitazone; and a pharmaceutically acceptable excipient.

In certain embodiments, the present invention relates to a pharmaceutical composition, comprising a compound of the present invention or a pharmaceutically acceptable salt thereof; a fibrate selected from the group consisting of fenofibrate and bezafibrate; and a pharmaceutically acceptable excipient.

In certain embodiments, the present invention relates to a pharmaceutical composition, comprising a compound of the present invention or a pharmaceutically acceptable salt thereof; niacin; a fibrate selected from the group consisting of fenofibrate and bezafibrate; and a pharmaceutically acceptable excipient.

Methods

An aspect of the invention relates to a method of treating a disease, disorder, or condition selected from the group consisting of hyperlipidemia, hypercholesterolemia, lipodystrophy, dyslipidemia, atherosclerosis and coronary artery disease, comprising the step of administering to a mammal in need thereof a therapeutically effective amount of a compound of the present invention or a pharmaceutically acceptable salt thereof. In one embodiment, the mammal is a human.

An aspect of the invention relates to a method of treating a disease, disorder, or condition selected from the group consisting of hyperlipidemia, hypercholesterolemia, lipodystrophy, dyslipidemia, atherosclerosis and coronary artery disease, comprising the step of administering to a mammal in need thereof a therapeutically effective amount of a pharmaceutical composition of the present invention. In one embodiment, the mammal is a human.

An aspect of the invention relates to a method of treating a disease, disorder, or condition selected from the group consisting of metabolic syndrome, obesity, fatty liver disease, and diabetes, comprising the step of administering to a mammal in need thereof a therapeutically effective amount of a compound of the present invention or a pharmaceutically acceptable salt thereof. In one embodiment, the mammal is a human.

An aspect of the invention relates to a method of treating a disease, disorder, or condition selected from the group consisting of metabolic syndrome, obesity, fatty liver disease, and diabetes, comprising the step of administering to a mammal in need thereof a therapeutically effective amount of a pharmaceutical composition of the present invention. In one embodiment, the mammal is a human.

An aspect of the invention relates to a method of raising serum high-density lipoprotein (HDL) levels, comprising the step of: administering to a mammal in need thereof a therapeutically effective amount of a compound of the present invention or a pharmaceutically acceptable salt thereof. In one embodiment, the mammal is a human.

An aspect of the invention relates to a method of raising serum high-density lipoprotein (HDL) levels, comprising the step of: administering to a mammal in need thereof a therapeutically effective amount of a pharmaceutical composition of the present invention. In one embodiment, the mammal is a human.

An aspect of the invention relates to a method of lowering serum low-density lipoprotein (LDL) levels or lowering serum lipoprotein (a) levels, comprising the step of administering to a mammal in need thereof a therapeutically effective amount of a compound of the present invention or a pharmaceutically acceptable salt thereof. In one embodiment, the mammal is a human.

An aspect of the invention relates to a method of lowering serum low-density lipoprotein (LDL) levels or lowering serum lipoprotein (a) levels, comprising the step of administering to a mammal in need thereof a therapeutically effective amount of a pharmaceutical composition of the present invention. In one embodiment, the mammal is a human.

An aspect of the invention relates to a method of treating a disease, disorder, or condition selected from the group consisting of congestive heart failure, cardiovascular disease, hypertension, coronary heart disease, angina, pellagra, Hartnup's syndrome, carcinoid syndrome, arterial occlusive disease, hypothyroidism, vasoconstriction, osteoarthritis, rheumatoid arthritis, Alzheimer's disease, disorders of the peripheral and central nervous system, hematological diseases, cancer, inflammation, respiratory diseases, and gastroenterological diseases, comprising the step of administering to a mammal in need thereof a compound of the present invention or a pharmaceutically acceptable salt thereof. In one embodiment, the mammal is a human.

An aspect of the invention relates to a method of treating a disease, disorder, or condition selected from the group consisting of congestive heart failure, cardiovascular disease, hypertension, coronary heart disease, angina, pellagra, Hartnup's syndrome, carcinoid syndrome, arterial occlusive disease, hypothyroidism, vasoconstriction, osteoarthritis, rheumatoid arthritis, Alzheimer's disease, disorders of the peripheral and central nervous system, hematological diseases, cancer, inflammation, respiratory diseases, and gastroenterological diseases, comprising the step of administering to a mammal in need thereof a pharmaceutical composition of the present invention. In one embodiment, the mammal is a human.

In certain embodiments, the present invention relates to any one of the aforementioned methods, further comprising co-administering a therapeutically effective amount of a statin. In one such embodiment, the co-administering is co-administering orally.

In certain embodiments, the present invention relates to any one of the aforementioned methods, further comprising co-administering a therapeutically effective amount of a statin; wherein the statin is selected from the group consisting of atorvastatin, cerivastatin, fluvastatin, lovastatin, mevastatin, pitavastatin, pravastatin, rosuvastatin and simvastatin. In one such embodiment, the co-administering is co-administering orally.

In certain embodiments, the present invention relates to any one of the aforementioned methods, further comprising co-administering a therapeutically effective amount of at least one additional therapeutic agent selected from the group consisting of 11β HSD-1 inhibitors, 5HT transporter inhibitors, 5HT2c agonists, 5-LO or FLAP inhibitors, α-glucosidase inhibitors, ABCA1 enhancers, ACC inhibitors, Acyl-CoA:cholesterol O-acyltransferase inhibitors, acyl-estrogens, antidiabetic agents, anti-dyslipidemic agents, anti-hypertensive agents, anti-oxidants, Apo A1 mimetics, Apo A1 modulators, Apo E mimetics, apolipoprotein-B secretion/microsomal triglyceride transfer protein (apo-B/MTP) inhibitors, appetite suppressants, aspirin, β3 agonists, bile acid reabsorption inhibitors, bile acid sequestrants, bombesin agonists, BRS3 agonists, $CB_1$ antagonists/inverse agonists, CCK-A agonists, cholesterol absorption inhibitor, cholesterol transport inhibitors, cholesteryl ester transfer protein (CETP) inhibitors, CNTF, CNTF agonists/modulators, a combination of ezetimibe and simvastatin and/or atorvastatin, CSL-111, dehydroepiandrosterone, delipidated HDL, DGAT antisense oligos, DGAT1 inhibitors, DGAT2 inhibitors, dicarboxylate transporter inhibitors, dopamine agonists, DP receptor antagonists, ezetimibe, FAS inhibitors, fatty acid binding protein (FABP) inhibitors, fatty acid transporter inhibitors, fatty acid transporter protein (FATP) inhibitors, flush inhibitors, FXR receptor modulators, galanin receptor antagonists, gemcabene, ghrelin antagonists, ghrelin antibodies, GLP-1 agonists, glucagon-like peptide-1 receptor agonists, glucocorticoid agonists/antagonists, glucose transporter inhibitors, HDL mimetics, HMG CoA reductase inhibitor compounds, HMG-CoA synthetase inhibitors, hormone sensitive lipase antagonists, human agouti-related proteins (AGRP), $H_3$ antagonists/inverse agonists, inorganic cholesterol sequestrants, L-4f, lapaquistat, leptin agonists/modulators, leptins, lipase inhibitors, lipoprotein synthesis inhibitors, lorapoprant, low density lipoprotein receptor inducers or activators, Lp(a) reducers, LXR receptor agonists, lyn kinase inhibitor, Mc3r agonists, Mc4r agonists, MCH1R antagonists, MCH2R agonists/antagonists, melanin concentrating hormone antagonists, mGluR5 antagonists, microsomal triglyceride transport inhibitors, monoamine reuptake inhibitors, natural water soluble fibers, NE transporter inhibitors, neuromedin U receptor agonists, neuropeptide-Y antagonists, niacin or niacin receptor agonists, nicotinic acid, noradrenergic anorectic agents, NPY1 antagonists, NPY2 agonists, NPY4 agonists, NPY5 antagonists, non-steroidal anti-inflammatory drug (NSAID) agents, omega-3 fatty acids, opioid antagonists, orexin receptor antagonists, PDE inhibitors, phentermine, phosphate transporter inhibitors, phytopharm compound 57, plant stanols and/or fatty acid esters of plant stanols, platelet aggregation inhibitors, PPAR-α agonists, PPAR-δ agonists, PPAR-δ partial agonists, PPAR-γ agonists, probucol, renin angiotensin inhibitors, reversed-4F, SCD-1 inhibitors, serotonin reuptake inhibitors, SGLT2 inhibitors, squalene epoxidase inhibitors, squalene synthesis inhibitors, sterol biosynthesis inhibitors, sympathomimetic agonists, thyroid hormone β agonists, thyromimetic agents, topiramate, triglyceride synthesis inhibitors, UCP-1 activators, UCP-2 activators, UCP-3 activators, and urocortin binding protein antagonists. In one such embodiment, the co-administering is co-administering orally.

In certain embodiments, the present invention relates to any one of the aforementioned methods, further comprising co-administering a therapeutically effective amount of at least one additional therapeutic agent selected from the group consisting of HMG CoA reductase inhibitors, aspirin, cholesteryl ester transfer protein inhibitors, NSAIDs, fibrates, a proprotein convertase subtilisin/kexin type (PCSK9), inorganic cholesterol sequestrants, AcylCoA:cholesterol O-acyltransferase inhibitors, CETP inhibitors, PPAR α agonists, PPAR γ agonists, bile acid reabsorption inhibitors, triglyceride synthesis inhibitors, lipoprotein receptor activators, DGAT1 inhibitors, SCD-1 inhibitors, lipase inhibitors, DP receptor antagonists, apo A1 modulators, cholesterol transport inhibitors, metformin, niacin receptor modulators, and DPP-IV inhibitors. In one such embodiment, the co-administering is co-administering orally.

In certain embodiments, the present invention relates to any one of the aforementioned methods, further comprising co-administering a therapeutically effective amount of at least one additional therapeutic agent selected from the group consisting of HMG CoA reductase inhibitors, cholesteryl ester transfer protein inhibitors, aspirin, NSAIDs, fibrates, DP receptor antagonists, ezetimibe or a combination of ezetimibe and simvastatin. In one such embodiment, the co-administering is co-administering orally.

In certain embodiments, the present invention relates to any one of the aforementioned methods, further comprising co-administering a therapeutically effective amount of at least one HMG CoA reductase inhibitor selected from lovastatin, simvastatin, pravastatin, atorvastatin, fluvastatin, cerivastatin, rivastatin, rosuvastatin calcium and pitavastatin. In one such embodiment, the co-administering is co-administering orally.

In certain embodiments, the present invention relates to any one of the aforementioned methods, further comprising co-administering simvastatin. In one such embodiment, the co-administering is co-administering orally.

In certain embodiments, the present invention relates to any one of the aforementioned methods, further comprising co-administering a cholesteryl ester transfer protein inhibitor. In one such embodiment, the co-administering is co-administering orally.

In certain embodiments, the present invention relates to any one of the aforementioned methods, further comprising co-administering ezetimibe, aspirin, ibuprofen, acetaminophen, or a combination of ezetimibe and simvastatin. In one such embodiment, the co-administering is co-administering orally.

An aspect of the invention relates to a method of treating hyperlipidemia, comprising the step of co-administering to a mammal in need thereof a therapeutically effective amount of a compound of the present invention; and a therapeutically effective amount of niacin. In one embodiment, the co-administering is co-administering orally. In one embodiment, the mammal is a human.

An aspect of the invention relates to a method of treating hyperlipidemia, comprising the step of co-administering to a mammal in need thereof a therapeutically effective amount of a pharmaceutical composition of the present invention; and a therapeutically effective amount of niacin. In one embodiment, the co-administering is co-administering orally. In one embodiment, the mammal is a human.

An aspect of the invention relates to a method of raising serum high-density lipoprotein (HDL) levels in a mammal, comprising the step of co-administering to a mammal in need thereof a therapeutically effective amount of a compound of the present invention; and a therapeutically effective amount of niacin. In one embodiment, the co-administering is co-administering orally. In one embodiment, the mammal is a human.

An aspect of the invention relates to a method of raising serum high-density lipoprotein (HDL) levels in a mammal, comprising the step of co-administering to a mammal in need thereof a therapeutically effective amount of a pharmaceutical composition of the present invention; and a therapeutically effective amount of niacin. In one embodiment, the co-administering is co-administering orally. In one embodiment, the mammal is a human.

An aspect of the invention relates to a method of lowering serum low-density lipoprotein (LDL) levels in a mammal, comprising the step of co-administering to a mammal in need thereof a therapeutically effective amount of a compound of the present invention; and a therapeutically effective amount of niacin. In one embodiment, the co-administering is co-administering orally. In one embodiment, the mammal is a human.

An aspect of the invention relates to a method of lowering serum low-density lipoprotein (LDL) levels in a mammal, comprising the step of co-administering to a mammal in need thereof a therapeutically effective amount of a pharmaceutical composition of the present invention; and a therapeutically effective amount of niacin. In one embodiment, the co-administering is co-administering orally. In one embodiment, the mammal is a human.

An aspect of the invention relates to a method of lowering serum lipoprotein (a) (Lp(a)) levels in a mammal, comprising the step of co-administering to a mammal in need thereof a therapeutically effective amount of a compound of the present invention; and a therapeutically effective amount of niacin. In one embodiment, the co-administering is co-administering orally. In one embodiment, the mammal is a human.

An aspect of the invention relates to a method of lowering serum lipoprotein (a) (Lp(a)) levels in a mammal, comprising the step of co-administering to a mammal in need thereof a therapeutically effective amount of a pharmaceutical composition of the present invention; and a therapeutically effective amount of niacin. In one embodiment, the co-administering is co-administering orally. In one embodiment, the mammal is a human.

An aspect of the invention relates to a method of treating hyperlipidemia, hypercholesterolemia, atherosclerosis, coronary artery disease, congestive heart failure, cardiovascular disease, hypertension, coronary heart disease, angina, pellagra, Hartnup's syndrome, carcinoid syndrome, arterial occlusive disease, obesity, hypothyroidism, vasoconstriction, osteoarthritis, rheumatoid arthritis, diabetes, Alzheimer's disease, lipodystrophy, or dyslipidemia, comprising the step of co-administering to a mammal in need thereof a therapeutically effective amount of a compound of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin and simvastatin. In one embodiment, the co-administering is co-administering orally. In one embodiment, the mammal is a human.

An aspect of the invention relates to a method of treating hyperlipidemia, hypercholesterolemia, atherosclerosis, coronary artery disease, congestive heart failure, cardiovascular disease, hypertension, coronary heart disease, angina, pellagra, Hartnup's syndrome, carcinoid syndrome, arterial occlusive disease, obesity, hypothyroidism, vasoconstriction, osteoarthritis, rheumatoid arthritis, diabetes, Alzheimer's disease, lipodystrophy, or dyslipidemia, comprising the step of co-administering to a mammal in need thereof a therapeutically effective amount of a pharmaceutical composition of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin and simvastatin. In one embodiment, the co-administering is co-administering orally. In one embodiment, the mammal is a human.

An aspect of the invention relates to a method of treating hyperlipidemia, comprising the step of co-administering to a mammal in need thereof a therapeutically effective amount of a compound of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin and simvastatin. In one embodiment, the co-administering is co-administering orally. In one embodiment, the mammal is a human.

An aspect of the invention relates to a method of treating hyperlipidemia, comprising the step of co-administering to a mammal in need thereof a therapeutically effective amount of a pharmaceutical composition of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin and simvastatin. In one embodiment, the co-administering is co-administering orally. In one embodiment, the mammal is a human.

An aspect of the invention relates to a method of raising serum high-density lipoprotein (HDL) levels in a mammal, comprising the step of co-administering to a mammal in need thereof a therapeutically effective amount of a compound of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin and simvastatin. In one embodiment, the co-administering is co-administering orally. In one embodiment, the mammal is a human.

An aspect of the invention relates to a method of raising serum high-density lipoprotein (HDL) levels in a mammal, comprising the step of co-administering to a mammal in need thereof a therapeutically effective amount of a pharmaceutical composition of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin and simvastatin. In one embodiment, the co-administering is co-administering orally. In one embodiment, the mammal is a human.

An aspect of the invention relates to a method of lowering serum low-density lipoprotein (LDL) levels in a mammal, comprising the step of co-administering to a mammal in need thereof a therapeutically effective amount of a compound of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin and simvastatin. In one embodiment, the co-administering is co-administering orally. In one embodiment, the mammal is a human.

An aspect of the invention relates to a method of lowering serum low-density lipoprotein (LDL) levels in a mammal, comprising the step of co-administering to a mammal in need thereof a therapeutically effective amount of a pharmaceutical composition of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin and simvastatin. In one embodiment, the co-administering is co-administering orally. In one embodiment, the mammal is a human.

An aspect of the invention relates to a method of lowering serum lipoprotein (a) (Lp(a)) levels in a mammal, comprising the step of co-administering to a mammal in need thereof a therapeutically effective amount of a compound of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin and simvastatin. In one embodiment, the co-administering is co-administering orally. In one embodiment, the mammal is a human.

An aspect of the invention relates to a method of lowering serum lipoprotein (a) (Lp(a)) levels in a mammal, comprising the step of co-administering to a mammal in need thereof a therapeutically effective amount of a pharmaceutical composition of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin and simvastatin. In one embodiment, the co-administering is co-administering orally. In one embodiment, the mammal is a human.

In certain embodiments, the present invention relates to any one of the aforementioned methods and the attendant limitations, wherein said statin is lovastatin or atorvastatin.

An aspect of the invention relates to a method of treating diabetes in a mammal, comprising the step of co-administering to a mammal in need thereof a therapeutically effective amount of a compound of the present invention or a pharmaceutically acceptable salt thereof; and a glitazone selected from the group consisting of troglitazone, rosiglitazone, and pioglitazone. In one embodiment, the co-administering is co-administering orally. In one embodiment, the mammal is a human.

An aspect of the invention relates to a method of treating diabetes in a mammal, comprising the step of co-administering to a mammal in need thereof a therapeutically effective amount of a pharmaceutical composition of the present invention; and a glitazone selected from the group consisting of troglitazone, rosiglitazone, and pioglitazone. In one embodiment, the co-administering is co-administering orally. In one embodiment, the mammal is a human.

An aspect of the invention relates to a method of treating diabetes in a mammal, comprising the step of co-administering to a mammal in need thereof a therapeutically effective amount of a compound of the present invention or a pharmaceutically acceptable salt thereof; niacin; and a glitazone selected from the group consisting of troglitazone, rosiglitazone, and pioglitazone. In one embodiment, the co-administering is co-administering orally. In one embodiment, the mammal is a human.

An aspect of the invention relates to a method of treating diabetes in a mammal, comprising the step of co-administering to a mammal in need thereof a therapeutically effective amount of a pharmaceutical composition of the present invention; niacin; and a glitazone selected from the group consisting of troglitazone, rosiglitazone, and pioglitazone. In one embodiment, the co-administering is co-administering orally. In one embodiment, the mammal is a human.

An aspect of the invention relates to a method of treating diabetes in a mammal, comprising the step of co-administering to a mammal in need thereof a therapeutically effective amount of a compound of the present invention or a pharmaceutically acceptable salt thereof; and a fibrate selected from the group consisting of fenofibrate and bezafibrate. In one embodiment, the co-administering is co-administering orally. In one embodiment, the mammal is a human.

An aspect of the invention relates to a method of treating diabetes in a mammal, comprising the step of co-administering to a mammal in need thereof a therapeutically effective amount of a pharmaceutical composition of the present invention; and a fibrate selected from the group consisting of fenofibrate and bezafibrate. In one embodiment, the co-administering is co-administering orally. In one embodiment, the mammal is a human.

An aspect of the invention relates to a method of treating diabetes in a mammal, comprising the step of co-administering to a mammal in need thereof a therapeutically effective amount of a compound of the present invention or a pharmaceutically acceptable salt thereof; niacin; and a fibrate selected from the group consisting of fenofibrate and bezafibrate. In one embodiment, the co-administering is co-administering orally. In one embodiment, the mammal is a human.

An aspect of the invention relates to a method of treating diabetes in a mammal, comprising the step of co-administering to a mammal in need thereof a therapeutically effective amount of a pharmaceutical composition of the present invention; niacin; and a fibrate selected from the group consisting of fenofibrate and bezafibrate. In one embodiment, the co-administering is co-administering orally. In one embodiment, the mammal is a human.

In certain embodiments, the present invention relates to any one of the aforementioned methods and the attendant limitations, wherein said mammal is a primate, bovine, ovine, rodent, equine, canine, or feline.

In certain embodiments, the present invention relates to any one of the aforementioned methods and the attendant limitations, wherein said mammal is a human.

In certain embodiments, the present invention relates to any one of the aforementioned methods and the attendant limitations, wherein said compound, compounds, or pharmaceutical composition are administered orally.

In certain embodiments, the present invention relates to any one of the aforementioned methods and the attendant limitations, wherein said compound, compounds, or pharmaceutical composition are administered intravenously.

In certain embodiments, the present invention relates to any one of the aforementioned methods and the attendant limitations, wherein said compound, compounds, or pharmaceutical composition are administered sublingually.

In certain embodiments, the present invention relates to any one of the aforementioned methods and the attendant limitations, wherein said compound, compounds, or pharmaceutical composition are administered by inhalation.

In certain embodiments, the present invention relates to any one of the aforementioned methods and the attendant limitations, wherein said compound, compounds, or pharmaceutical composition are administered ocularly.

In certain embodiments, the present invention relates to any one of the aforementioned methods and the attendant limitations, wherein said compound, compounds, or pharmaceutical composition are administered transdermally.

In certain embodiments, the present invention relates to any one of the aforementioned methods and the attendant limitations, wherein said compound, compounds, or pharmaceutical composition are administered rectally.

In certain embodiments, the present invention relates to any one of the aforementioned methods and the attendant limitations, wherein said compound, compounds, or pharmaceutical composition are administered vaginally.

In certain embodiments, the present invention relates to any one of the aforementioned methods and the attendant limitations, wherein said compound, compounds, or pharmaceutical composition are administered topically.

In certain embodiments, the present invention relates to any one of the aforementioned methods and the attendant limitations, wherein said compound, compounds, or pharmaceutical composition are administered intramuscularly.

In certain embodiments, the present invention relates to any one of the aforementioned methods and the attendant limitations, wherein said compound, compounds, or pharmaceutical composition are administered subcutaneously.

In certain embodiments, the present invention relates to any one of the aforementioned methods and the attendant limitations, wherein said compound, compounds, or pharmaceutical composition are administered buccally.

In certain embodiments, the present invention relates to any one of the aforementioned methods and the attendant limitations, wherein said compound, compounds, or pharmaceutical composition are administered nasally.

EXEMPLIFICATION

The invention now being generally described, it will be more readily understood by reference to the following, which is included merely for purposes of illustration of certain aspects and embodiments of the present invention, and is not intended to limit the invention.

Example 1

Synthetic Schemes

A. Compound ARI-001

Reaction conditions: i. HCHO, Morpholine.HCl, n-PrOH, 100° C.; ii. NaOH, then HCl.

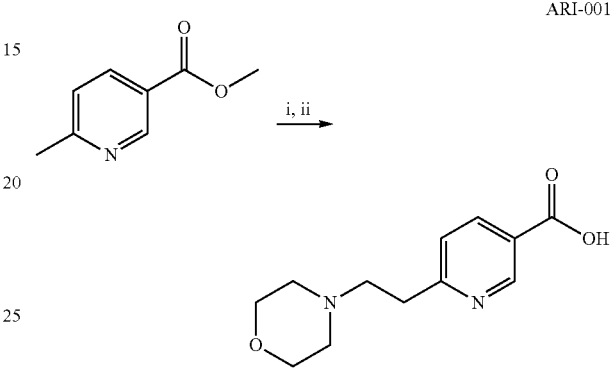

6-methyl-nicotinic acid methyl ester (4.5 g, 30 mmol), morpholine hydrochloride (1.85 g, 15 mmol), n-PrOH (18 mL) and formaldehyde solution (in water, 37%) (1.2 g, 15 mmol) were added to a 50 mL flask equipped with a condenser. The reaction mixture was refluxing with a pre-heated 100° C. oil bath for 2.5 hr under argon. Then the mixture was allowed to stand at room temperature overnight and a yellow needle crystal was precipitated out (If there was no precipitation formed at room temperature, cold room (4° C.) or even −10° C. fridge would be recommended). Isolated the crystal by filtration and washed with a little ethyl ether to afford the crude product of step 1 as a HCl salt (1.5 g, 35% yield; purity was about 95%, the double Mannich addition by-product was about 3%). This crude product was further purified by one time re-crystallized from n-PrOH and MeOH to give the purer product of step 1 as an off-white or pale yellow powder (1.2 g, 28% yield; purity was 99.1%, the double Mannich addition by-product was 0.9%).

The product of step 1 (1.5 g, 5 mmol) was dissolved in MeOH (20 mL) and water (10 mL), 1 N LiOH (15 mL) was added under ice-water cooling. The resulting mixture was stirred at room temperature overnight, and then adjusted pH to 2-3 with 2N HCl. After condensed under vacuum the residue was then further purified with preparative HPLC eluting with solvent acetonitrile and water (5 mM HCl added) to afford 1.2 g of the target compound ARI-001 as a white powder (HCl salt, total yield was about 30% for two steps when used the crude product of step 1).

B. Compound ARI-002

Reaction conditions: i. HCHO, Morpholine.HCl

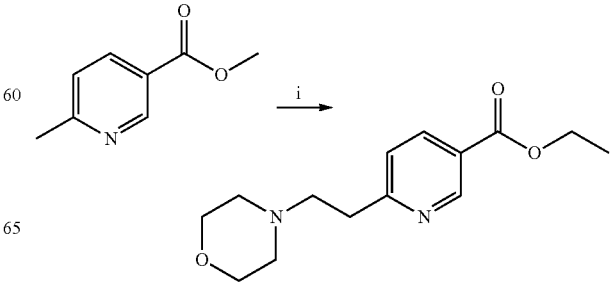

C. Compound ARI-001D
Reaction conditions: i. HCHO, Morpholine-d8.HCl; ii. NaOH, then HCl.
D. Compound ARI-005
Reaction conditions: i. 5-Indanol, EDAC, DMAP.
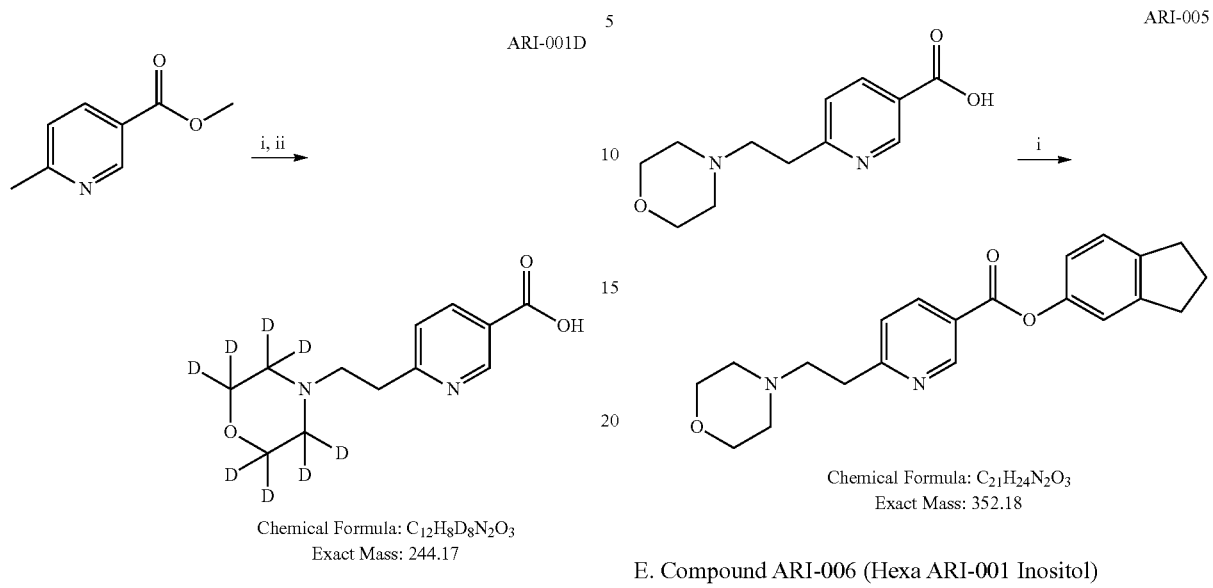
E. Compound ARI-006 (Hexa ARI-001 Inositol)
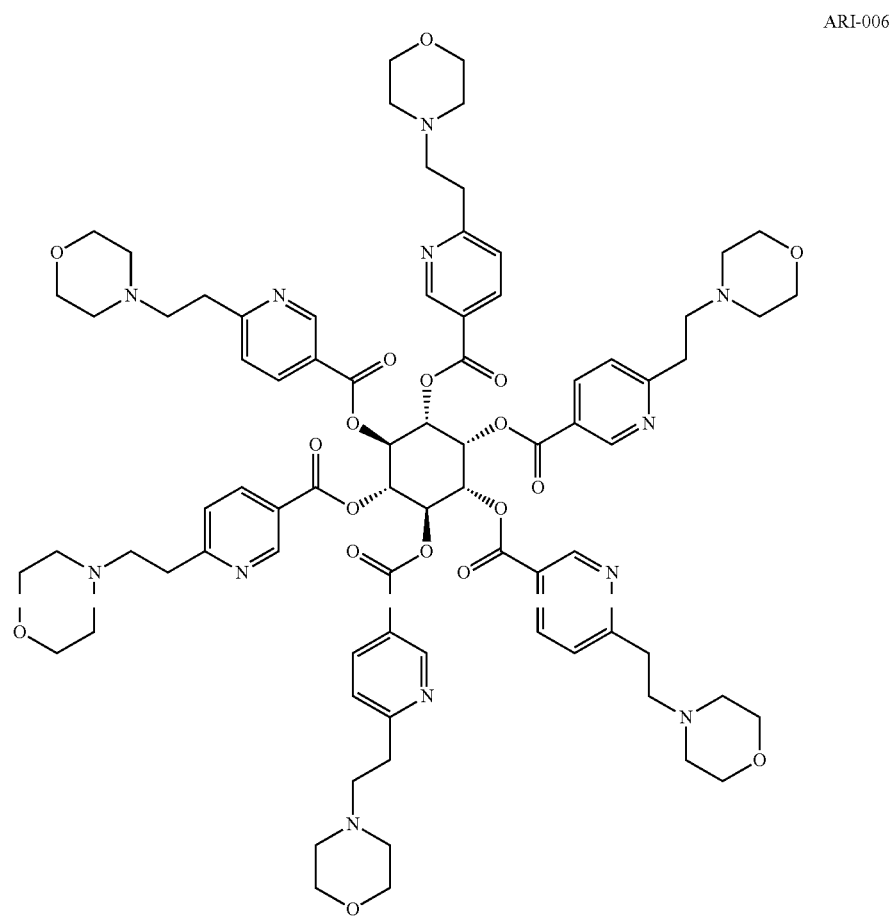

65
Reaction conditions: i. imyo-Inositol, EDCI, DMAP.
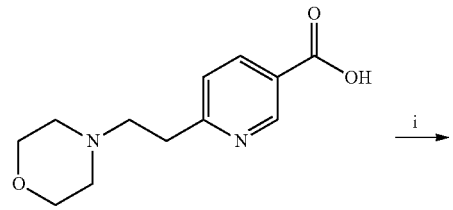
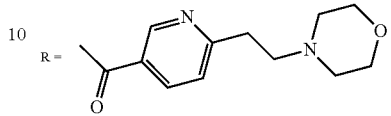
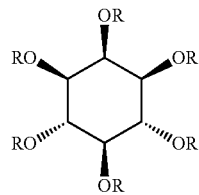
F. Compound ARI-008
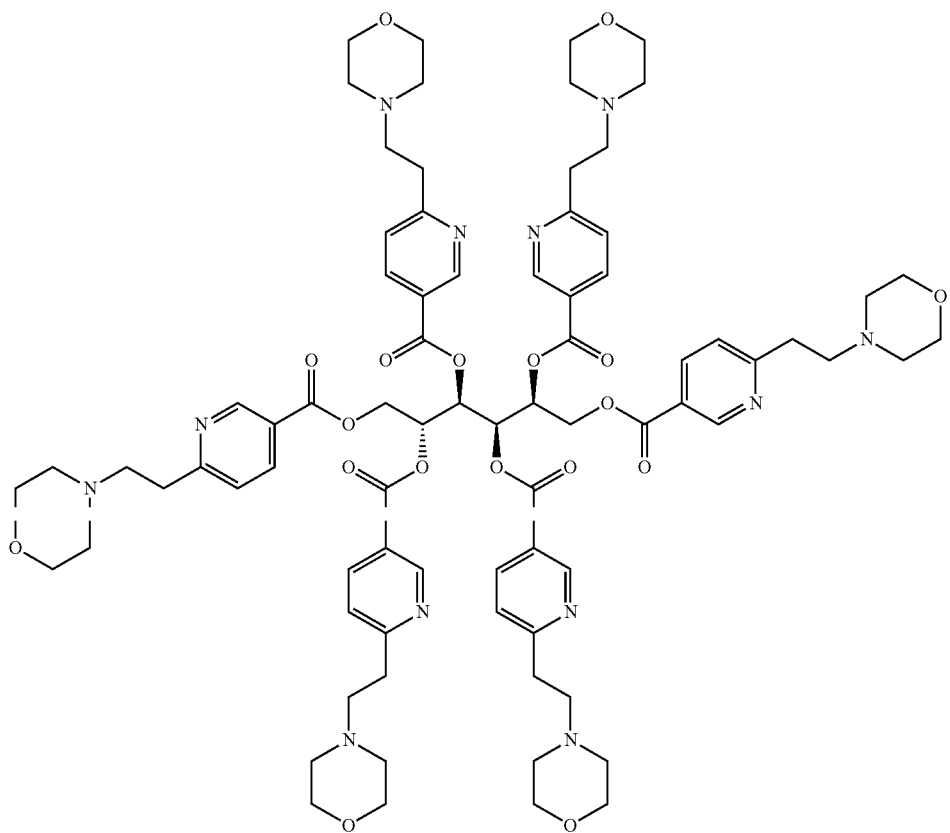
ARI-008

67
Reaction conditions: i. D-Sorbitol, EDAC, DMAP.
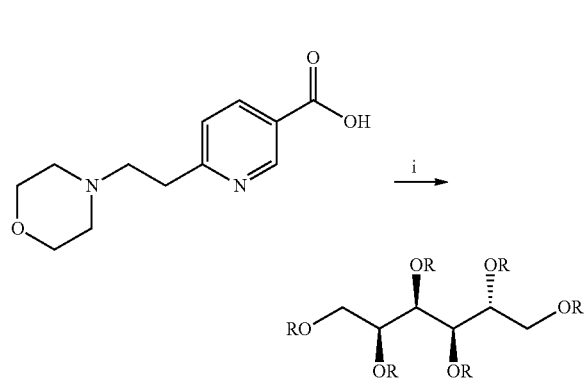
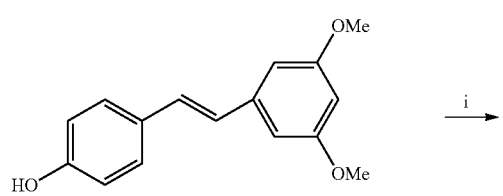
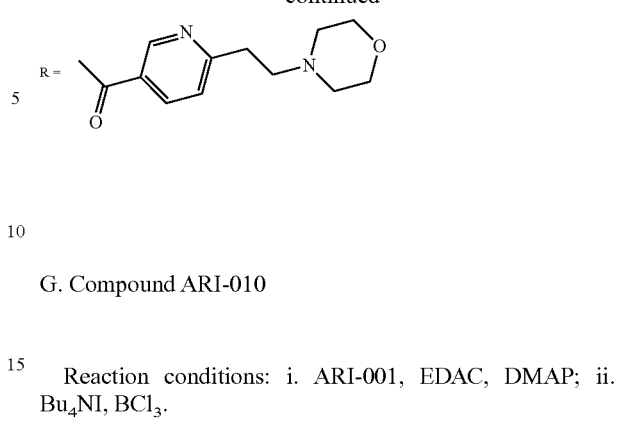
G. Compound ARI-010
Reaction conditions: i. ARI-001, EDAC, DMAP; ii. Bu₄NI, BCl₃.
ARI-010
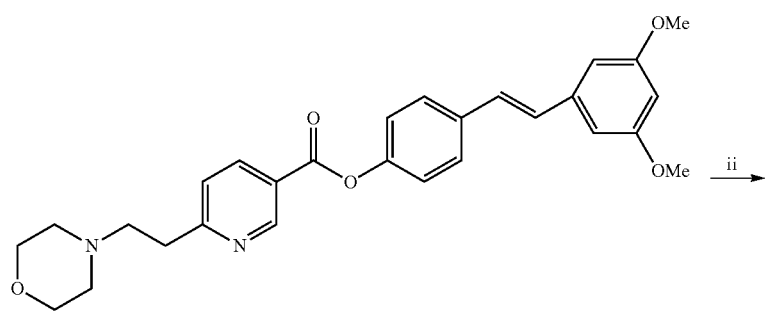
Chemical Formula: $C_{28}H_{30}N_2O_5$
Exact Mass: 474.22
Molecular Weight: 474.55
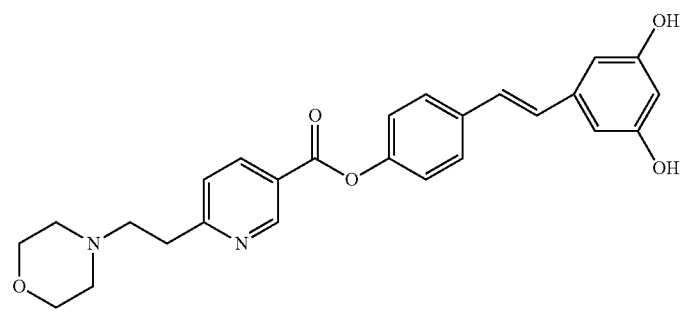
Chemical Formula: $C_{26}H_{26}N_2O_5$
Exact Mass: 446.18
Molecular Weight: 446.50

Example 2

In Vitro Studies

ARI-001 was synthesized as described above. Purity was determined independently before use in experiments by examination via liquid chromatography-mass spectroscopy (LC-MS). A sample of material was dissolved in water/acetonitrile and injected onto a Discovery C-18 reverse phase column. The mobile phase began as 2%:98% acetonitrile:water, which was held for three minutes, after which a linear gradient was started that ran over 6 minutes, increasing the percent of acetonitrile until a final ratio of 98%:2% acetonitrile:water was reached. This final ratio was held for 3 minutes. UV detection was collected at 215 nm, as shown in FIG. 1. The major peak was identified as ARI-001.

The purity was determined by the ratio of the area of the major peak (3.59 minutes) to the sum of areas of all peaks. Purity was determined to be 98.9%. The minor peaks were not identified.

Figure 2:
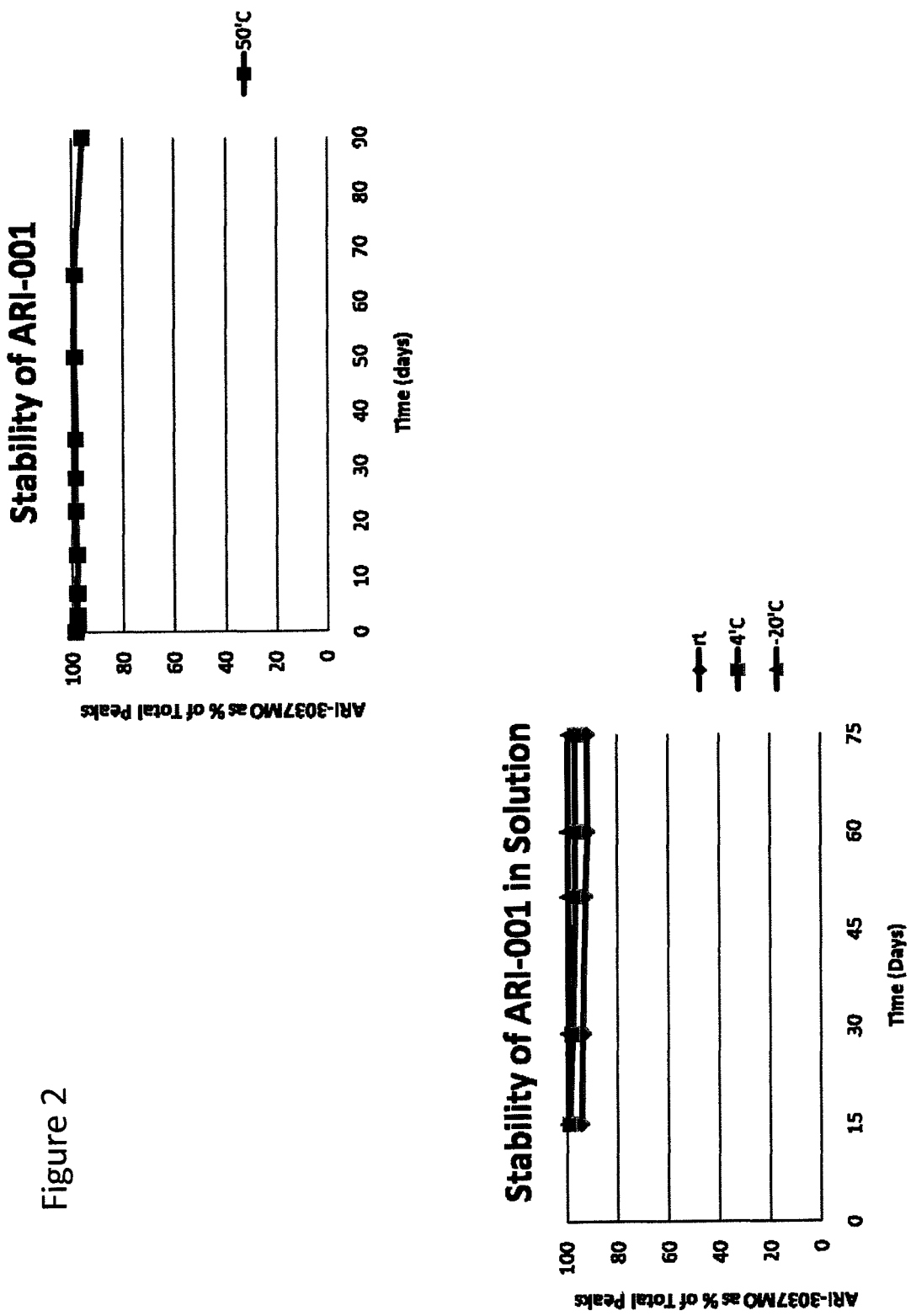
FIG. 2. Relative stability of ARI-001 under storage conditions as defined in the text. Total area representing the peak for ARI-001 was calculated and then normalized to the total area of peaks identified on the LC-MS trace. This is expressed as % of total peaks. Upper graph, powder formulation; (■) standard conditions: 50° C., no specified humidity. Lower graph, liquid formulation; (◇) room temperature (rt); (■) 4° C.; (▲) 20° C.

Stability was determined by storing ARI-001 under 50° C. with no specified humidity requirement. At various time points over the course of 3 months (90 days), a small sample (<5 mg) of ARI-001 was collected for analysis using LC-MS under the same conditions as used for purity determination (vide supra). FIG. 2 shows the time course of stability of ARI-001 under such conditions.

Under standard conditions (50° C., unregulated humidity), ARI-001 remained 98.9% pure for a period of 65 days. Only by 90 days at 50° C. did ARI-001 begin to show any degradation. After 90 days, the compound was found to be 95.9% pure.

Example 3

In Vivo Studies

To investigate the effects of ARI-001 on lipid modulation, a hamster model was developed and utilized in the setting of chronic administration of compound. This model, its development, and the effects of ARI-001 are described herein.

Effects of Diet Modification on the Lipid Profile of Hamsters.

Like other rodents, the lipid profile in Golden Syrian hamsters predominantly consists of HDL, with little LDL or VLDL cholesterol. However, on a high-fat diet, hamsters experience an increase in the cholesterol pool, including triglycerides and free fatty acids. Adding a sugar to the drinking water source such as 10% fructose expands the triglyceride pool significantly, including the VLDL. On this diet, the hamster becomes a useful model for investigating the role of modulators on triglycerides and VLDL, and LDL cholesterol. Indeed, literature sources have utilized this model to investigate triglyceride and free fatty acid modulating compounds such as fenofibrate.

We examined the effects of diet modulation on the lipid profile of male Syrian Golden hamsters. Hamsters were ordered from Charles River Labs (Wilmington, Mass.), and requested to be 111-120 g in weight (correspondingly 56-61 days old). Hamsters were kept in cages of 4-5 per cage, and maintained on a standard light cycle of 12 hours on/12 hours off. All diets were obtained from Dyets, Inc. (Bethlehem, Pa.). "Normal Diet" was a standard rodent chow, catalog #5001, produced into pellets. Water and this standard chow diet were available to this group of hamsters ad libitum. Food was added to cages as needed, but no less frequently than twice per week. "High Fat Diet" was the same standard rodent chow supplemented with the following: 11.5% corn oil, 11.5% coconut oil, 0.5% cholesterol, and 0.25% deoxycholate. This is also available directly from Dyets, Inc., as catalog #611201. Both diets were ordered in 10 kg batches and stored at 4° C. for durations of the experiments (4-8 weeks), and at −20° C. for longer storage (up to six months). Water and this high fat diet were available to this group of hamsters ad libitum. The "High Fat+Fructose" group was fed the same fat-supplemented chow as the "high fat diet" group (#611201), but water was supplemented with fructose to a final concentration of 10%. Fructose was supplied from Now Foods (catalog #6931) and distributed by Lucky Vitamin (catalog #WB48432). Fructose water was prepared by adding 400 g of fructose to 4 L of water and stirring at room temperature until dissolved. Fructose water was stored at 4° C. until use. When provided to hamsters, fructose water was kept in a water bottle in the hamster cages at room temperature, exactly as standard water was. Fructose water and high fat chow were provided to this group of hamsters ad libitum. All animals remained on their respective diets for 21 days.

To begin this experiment, hamsters were randomly assigned to groups defined by the diet modifications above. After a fixed time, blood was collected from hamsters (N=3-4) to determine the lipid contents of the plasma. Because of limitations in the ability to adequately collect blood from hamsters, all blood samples were obtained via a terminal cardiac puncture preceded by asphyxiation with carbon dioxide. Blood (approximately 2 mL volume) was collected with a 22 G needle into a 5 mL syringe and transferred to a $K_2$EDTA tube. The samples were kept on ice until centrifugation (14,000 rpm for 10 minutes at 4° C.) to separate plasma. Plasma was then aliquoted to tubes for storage at −80° C. until analysis.

Lipid parameters were determined using commercially available kits from Wako USA (Richmond, Va.) according to manufacturer's directions.

TABLE 1

Lipid values from hamsters on one of three different diets for 21 days. Hamsters were sacrificed and their plasma was analyzed as described. Values represent the average of measurements of each parameter (N = 3), with standard deviation. TC: total cholesterol; HDL: high-density lipoprotein cholesterol; LDL: low-density lipoprotein cholesterol; TG: triglycerides; FFA: free fatty acids.

| Day 21 | TC (±SD) (mg/dL) | HDL (±SD) (mg/dL) | LDL (±SD) (mg/dL) | TG (±SD) (mg/dL) | FFA (±SD) (mEq/L) |
|---|---|---|---|---|---|
| Normal Diet | 115 ± 8 | 63 ± 6 | 17 ± 3 | 325 ± 89 | 0.76 ± 0.02 |
| High Fat Diet | 680 ± 82*** | 130 ± 16 | 384 ± 20*** | 1129 ± 123** | 1.65 ± 0.42* |

TABLE 1-continued

Lipid values from hamsters on one of three different diets for 21 days. Hamsters were sacrificed and their plasma was analyzed as described. Values represent the average of measurements of each parameter (N = 3), with standard deviation. TC: total cholesterol; HDL: high-density lipoprotein cholesterol; LDL: low-density lipoprotein cholesterol; TG: triglycerides; FFA: free fatty acids.

| Day 21 | TC (±SD) (mg/dL) | HDL (±SD) (mg/dL) | LDL (±SD) (mg/dL) | TG (±SD) (mg/dL) | FFA (±SD) (mEq/L) |
|---|---|---|---|---|---|
| High Fat + Fructose | 654 ± 135** | 97 ± 41 | 282 ± 85** | 1658 ± 673* | 2.17 ± 0.43** |

*$p < 0.05$ compared to Normal Diet within the same parameter
**$p < 0.01$ compared to Normal Diet within the same parameter
***$p < 0.001$ compared to Normal Diet within the same parameter Lipid values from control animals (zero days on any of the three diets described above) were essentially indistinguishable (see Table 1). By day 21, both diet modifications had significant effects on the lipid profiles of these hamsters when compared to animals on normal chow diet. All parameters were significantly increased from control ($p<0.05$ in all groups), with the exception of HDL. As predicted, the addition of fructose to the high fat diet further increased the triglyceride and free fatty acid concentrations to a greater extent than the high fat diet alone. HDL was unchanged from the normal diet group, regardless of the diet modification.

Fast protein liquid chromatography (FPLC) was used to separate the different cholesterol subpopulations from samples of hamster plasma. Briefly, plasma from each animal within a given cohort was pooled together and applied to an AKTA liquid handling system with a Superose 6 10/300 GL column (product #14-5172-01, GE Life Sciences). 250 μL of sample was applied to the injection system, diluted with 5 mL of buffer (100 mM $Na_2HPO_4$, 100 mM NaCl, pH 7.5), loaded onto the column, and eluted with 23.5 mL of buffer at a flow rate of 1.0 mL/min, into fractions of size 0.24 mL. Each fraction was individually measured for cholesterol concentration using the total cholesterol kit from Wako as described above with the following modification: sample volume was increased to 30 μL and the reagent volume was decreased to 60 μL.

FPLC traces produce continuous curves with three distinct peaks, representing each of the cholesterol subpopultions: VLDL, LDL, and HDL. Because the column used in this experiment is a size-exclusion column, the largest particles appear first, while the smallest appear last. Hence, VLDL is the first peak on the trace, followed by LDL, with HDL appearing last. If each of these peaks is assumed to take a Gaussian distribution, one can deconvolute the FPLC trace into each of these three components to determine the contribution that each component makes to the whole curve.

Figure 3:
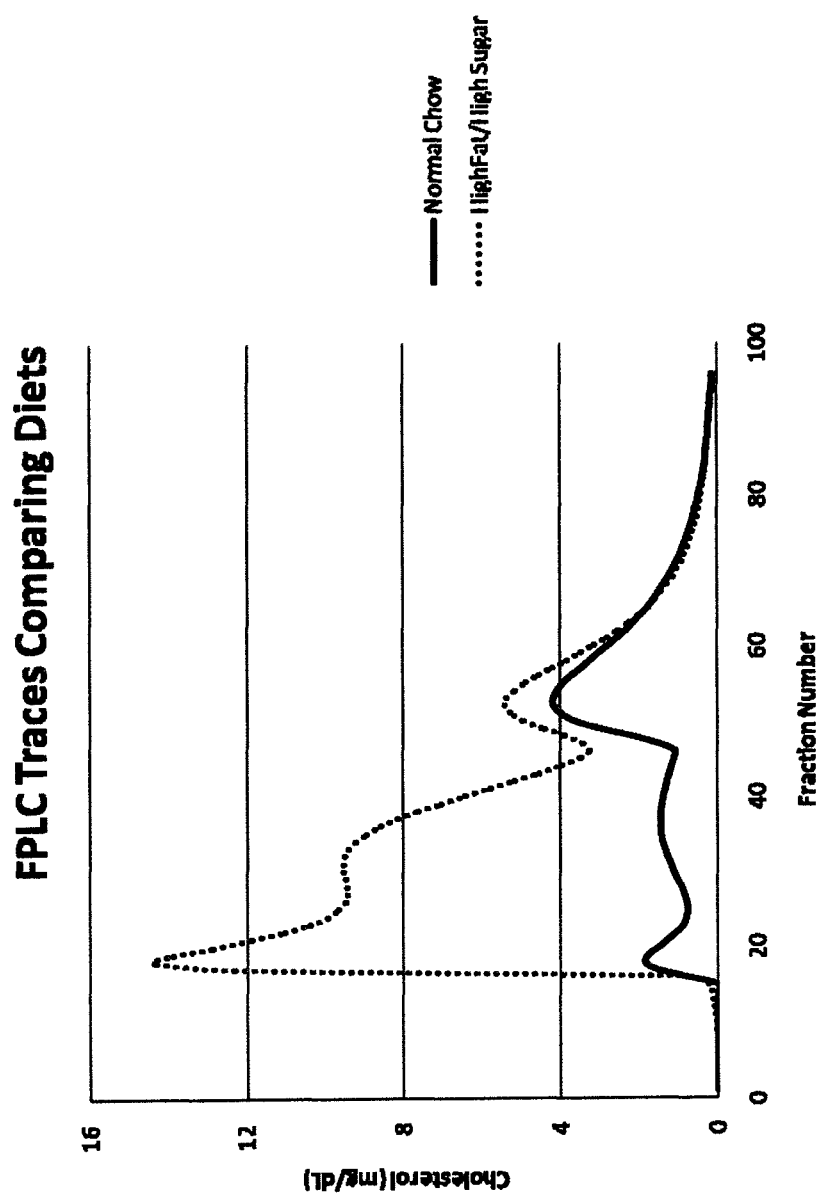
FIG. 3. Overlaid FPLC traces of pooled plasma from hamsters on either a normal chow diet (solid line) or a high fat+high sugar (HF/HS) diet (dotted line).

FIG. 3 illustrates the FPLC traces of plasma pooled from hamsters on two different diets for three weeks. The VLDL curve is vastly expanded on the high fat+fructose diet. The LDL peak is also much higher. Interestingly, there is very little difference in the HDL peak, indicating that the diet modification has a much more powerful effect on the non-HDL cholesterol population. This model then lends itself to being a useful means by which to measure the effects of ARI-001 on VLDL and LDL cholesterol.

ARI-001 Lowers LDL Cholesterol, Triglycerides, and Free Fatty Acid Levels in HF/HS Hamsters.

Male Golden Syrian hamsters were purchased from Charles River Labs (111-120 g, 56-61 days) and acclimated to a high fat+fructose (herein, referred to as "HF/HS") diet as described above for two weeks. Hamsters were assigned into cohorts by body weight after two weeks' acclimation to the diet. Twelve hamsters were assigned to the vehicle group, 9 were assigned to receive niacin at a dose of 1200 mg/kg, 10 were assigned to receive ARI-001 at a dose of 1120 mg/kg, and 10 were assigned to receive ARI-001 at a dose of 2240 mg/kg. At the end of this diet acclimation period, hamsters were orally gavaged with 1 mL of a solution of vehicle (water), niacin, or ARI-001 at one of the two doses. Hamsters were dosed once per day for a total of 18 days. All animals remained on the above-described HF/HS diet throughout the dosing period. Dosing solutions for each cohort were prepared for 7 days at a time, although enough was prepared to last for 8 days. Each solution was stored at room temperature between administrations. Cohorts were defined according to Table 2 below. Because of the molecular weight difference between niacin and ARI-001, doses are given in both mg/kg and mmol/kg. Note that 1200 mg/kg of niacin is equivalent to 2240 mg/kg of ARI-001 on a molar basis.

TABLE 2

Assignments to cohorts for 18 day dosing study in HF/HS hamsters.

| Compound | Dose (mg/kg) | Dose (mmol/kg) | Animals | Days |
|---|---|---|---|---|
| Vehicle | 0 | 0 | 12 | 18 |
| Niacin | 1200 | 9.75 | 10 | 18 |
| ARI-001 | 1120 | 4.88 | 10 | 18 |
| ARI-001 | 2240 | 9.75 | 10 | 18 |

As shown in Table 3, ARI-001 given via oral gavage for 18 days at 2240 mg/kg lowered the LDL-cholesterol and total cholesterol levels in a HF/HS hamster model. ARI-001 also lowered triglycerides and free fatty acid levels, with very little variation between animals as illustrated by the small standard deviation. At the molar equivalent dose of 1200 mg/kg, niacin was unable to confer these effects in this animal model, suggesting that ARI-001 is at least 1.67-times more efficacious than niacin with respect to the LDL cholesterol parameter, and at least 1.54-times more efficacious than niacin with respect to the total cholesterol parameter. Of note are the triglyceride and free fatty acid values, which demonstrated responders among all animals in the 2240 mg/kg ARI-001 group. That there is a very small standard deviation among these data points reflects the impressive response rate among these animals. The HDL/TC ratio was calculated by dividing each individual hamster's HDL cholesterol level by his total cholesterol level. The fraction that resulted is the HDL/TC ratio. This parameter was higher than the vehicle cohort's, with impressive statistical significance ($p<0.001$). This does not likely represent a powerful increase in HDL, as the absolute HDL value measured was increased by only 33% in the 2240 mg/kg ARI-001 group compared to vehicle. Rather, the very powerful change in the HDL/TC ratio likely represents a system-wide reduction in cholesterol populations, with the exception of HDL, which was not only spared from such reductions, but was possibly increased.

Figure 5:
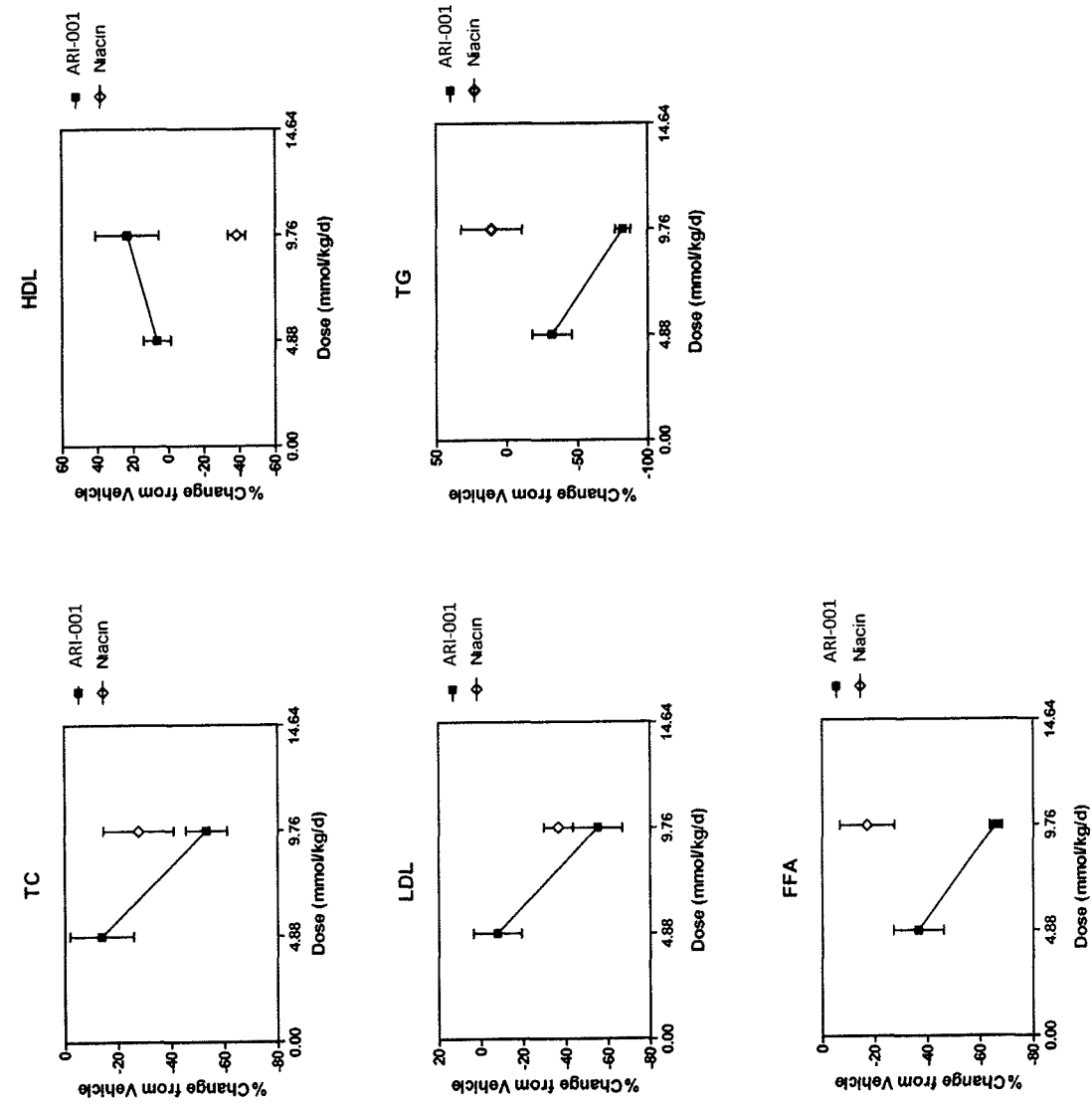
FIG. 5. Lipid parameter changes as a function of dose of ARI-001 (represented in mmol/kg/d). ARI-001 (■ and connecting line) demonstrates a dose-dependent effect on lipid values in HF/HS hamsters. Niacin (▲) showed significance with respect to changes in total cholesterol (TC), high-density lipoporotein (HDL), and low-density lipoprotein (LDL) only.

FIG. 5. Moreover, at the molar equivalent dose, ARI-001 effects a more powerful response than niacin in all lipid parameters measured.

ARI-001 Lowers LDL Cholesterol, Triglycerides, and Free Fatty Acids in a Time-Dependent Manner.

Thirty-two male Golden Syrian hamsters were acclimated over two weeks to a HF/HS diet as described above. After a

TABLE 3

Lipid parameters from HF/HS hamsters dosed orally with vehicle, niacin, or ARI-001 for 18 days. TC, total cholesterol. Values given are mean ± standard deviation. P-values are reported from 2-tailed unpaired t-tests comparing to vehicle treated within the same parameter.

| Cohort | TC (mg/dL) ± SD | HDL (mg/dL) ± SD | LDL (mg/dL) ± SD | TG (mg/dL) ± SD | FFA (mEq/L) ± SD | HDL/TC ± SD |
|---|---|---|---|---|---|---|
| Vehicle | 857 ± 422 | 139 ± 32 | 253 ± 82 | 1065 ± 465 | 1.95 ± 0.53 | 0.21 ± 0.11 |
| Niacin: 1200 mg/kg | 552* ± 183 | 79 ± 26*** | 170 ± 52* | 1555 ± 808 | 1.82 ± 0.69 | 0.17 ± 0.11 |
| ARI-001: 1120 mg/kg | 653 ± 194 | 142 ± 34 | 253 ± 91 | 957 ± 550 | 1.39 ± 0.65* | 0.24 ± 0.14 |
| ARI-001: 2240 mg/kg | 343 ± 104** | 186 ± 74* | 114 ± 33*** | 138 ± 80*** | 0.75 ± 0.15*** | 0.48 ± 0.07*** |

Figure 4:
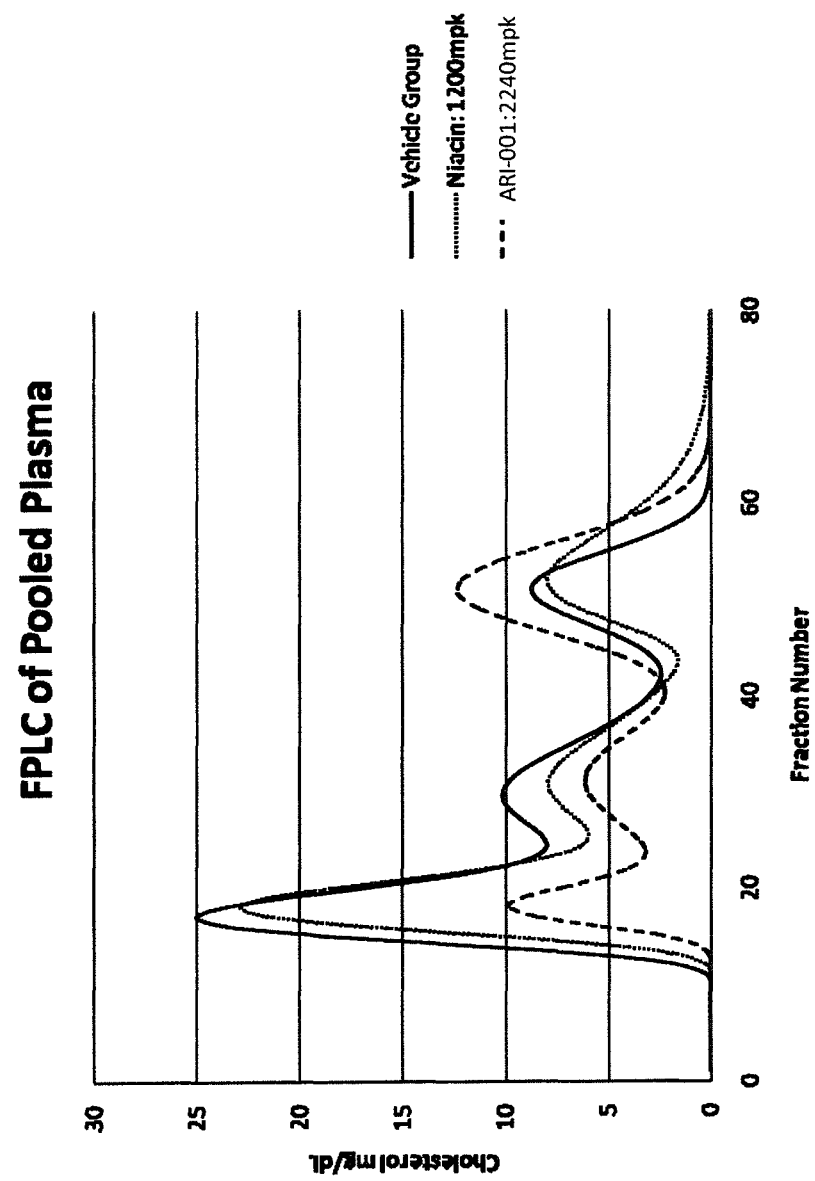
FIG. 4. FPLC traces of pooled plasma from hamsters receiving vehicle (solid line), 1200 mg/kg (mpk) niacin (dotted line), or 2240 mg/kg ARI-001 (dashed line).

*$p < 0.05$ compared to Vehicle within the same parameter
**$p < 0.01$ compared to Vehicle within the same parameter
***$p < 0.001$ compared to Vehicle within the same parameter The measured HDL values were borderline significant ($p=0.06$) between the 2240 mg/kg ARI-001 group and vehicle. There was a considerable increase in significance when considering the calculated HDL/TC values. The FPLC traces also demonstrated a significant difference in lipid profile between these two groups. FPLC was performed as described above. Curves were deconvoluted as described above. Not only were the VLDL and the LDL peaks considerably decreased compared to vehicle, but the HDL curve was notably larger in the ARI-001 trace. See FIG. 4.

Male Golden Syrian hamsters from the previously described experiment demonstrated a dose dependence on ARI-001 with respect to lipid alteration. 2240 mg/kg is an effective dose for 18 days of daily treatment for nearly all parameters: total cholesterol, LDL cholesterol, triglycerides, and free fatty acids. However, 1120 mg/kg shows only modest effects on these parameters, with only the free fatty acids parameter demonstrating a statistically significant effect compared to vehicle. Nonetheless, the trend is clear between the doses for all lipid parameters investigated, as shown in two week induction period, animals were assigned to cohorts for 18 days of study on either vehicle or ARI-001 (1120 mg/kg), or to cohorts for 28 days of study on either vehicle or ARI-001 (1120 mg/kg). Each of the four groups had 8 hamsters. Solutions were prepared and stored as described above Animals were dosed a volume of 1 mL per day for either 18 or 28 consecutive days, as previously described. At the end of the study, hamsters were sacrificed, their blood collected into $K_2$EDTA tubes, plasma separated by centrifugation and frozen until analysis. All lipids were analyzed using commercially available kits (Wako USA) as described above. In Table 4 below, both 18-day and 28-day vehicle animals are combined into a single vehicle group (N=16).

TABLE 4

Lipid parameters from HF/HS hamsters dosed orally with vehicle or ARI-001 for 18 days or 28 days. Values given are mean ± standard deviation. P-values are reported from 2-tailed unpaired t-tests comparing to vehicle treated within the same parameter.

| Cohort | TC (mg/dL) ± SD | HDL (mg/dL) ± SD | LDL (mg/dL) ± SD | TG (mg/dL) ± SD | FFA (mEq/L) ± SD | HDL/TC ± SD |
|---|---|---|---|---|---|---|
| Vehicle | 796 ± 253 | 135 ± 40 | 363 ± 85 | 1023 ± 630 | 1.30 ± 0.45 | 0.19 ± 0.09 |
| ARI-001: 1120 mg/kg, 18 Days | 668 ± 239 | 153 ± 30 | 346 ± 121 | 833 ± 410 | 1.06 ± 0.56 | 0.27 ± 0.15 |
| ARI-001: 1120 mg/kg, 28 Days | 420 ± 85*** | 138 ± 26 | 175 ± 80*** | 388 ± 82** | 0.56 ± 0.12*** | 0.34 ± 0.09*** |

**$p < 0.01$ compared to Vehicle within the same parameter
***$p < 0.001$ compared to Vehicle within the same parameter ARI-001 showed favorable effects on lipids when a dose of 1120 mg/kg was carried out to 28 days. When hamsters were dosed for 28 days instead of 18 days, all lipid parameters measured achieved a statistically significant difference compared to vehicle, except for HDL, which showed no difference compared to vehicle. The reductions seen at 1120 mg/kg for 28 days were greater than after 18 days of dosing. However, these reductions were not nearly as impressive as those seen with 18 days at the higher dose of 2240 mg/kg.

Correlation Between Plasma Lipid Biomarkers and ARI-001 Plasma Concentrations.

Figure 6:
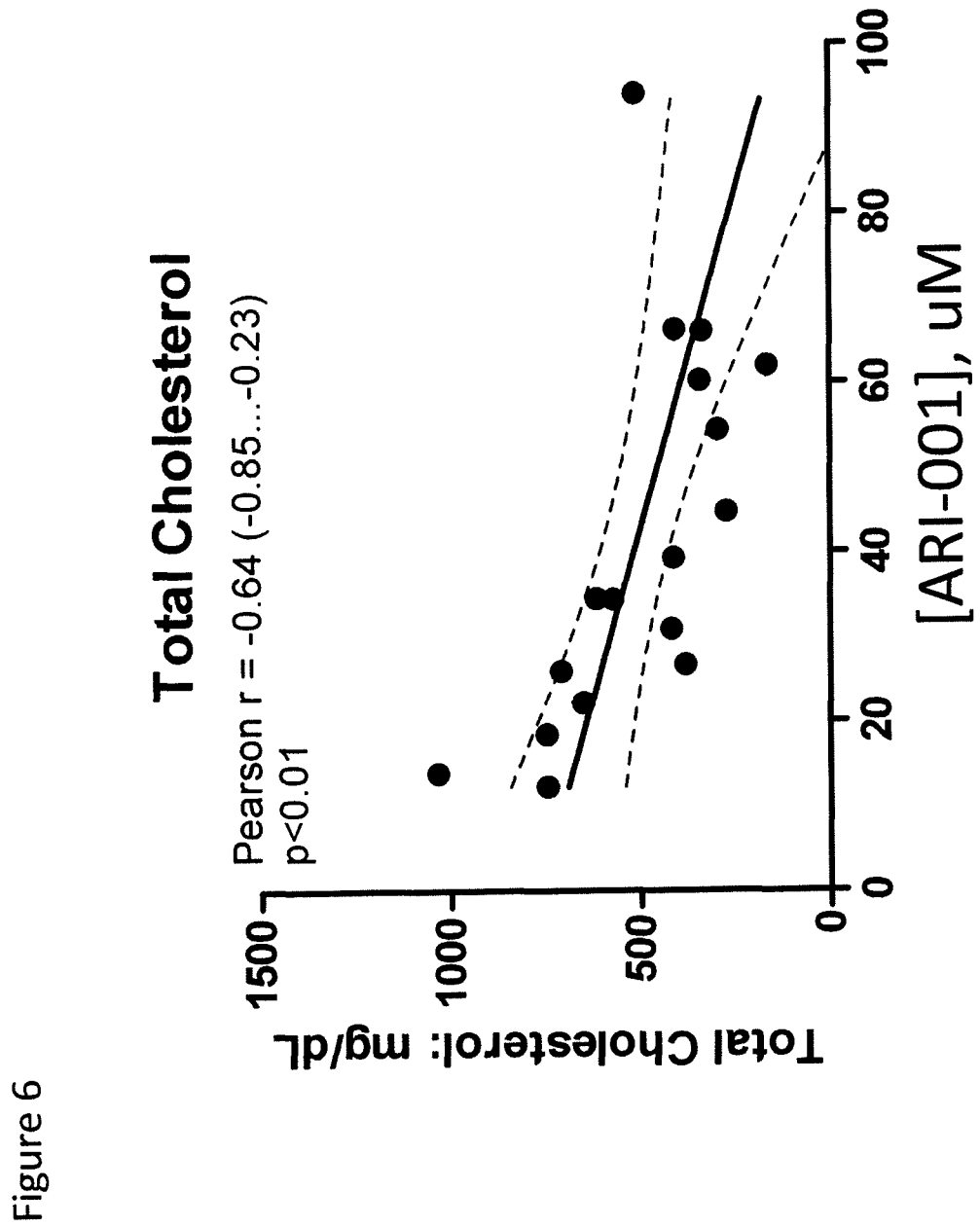
FIGS. 6 and 7. Correlation between lipid parameters and plasma concentrations of ARI-001. Each lipid parameter achieved statistically significant negative correlations with ARI-001 concentrations, except for HDL, which was statistically significant and positive. The linear correlation line is drawn (solid line), as well as the 95% confidence zone of the correlation line (dashed curves). Pearson r correlation coefficients are given for each data set, with 95% confidence interval in parentheses. P-values are the results of 2-tailed unpaired t-tests.
Figure 7:
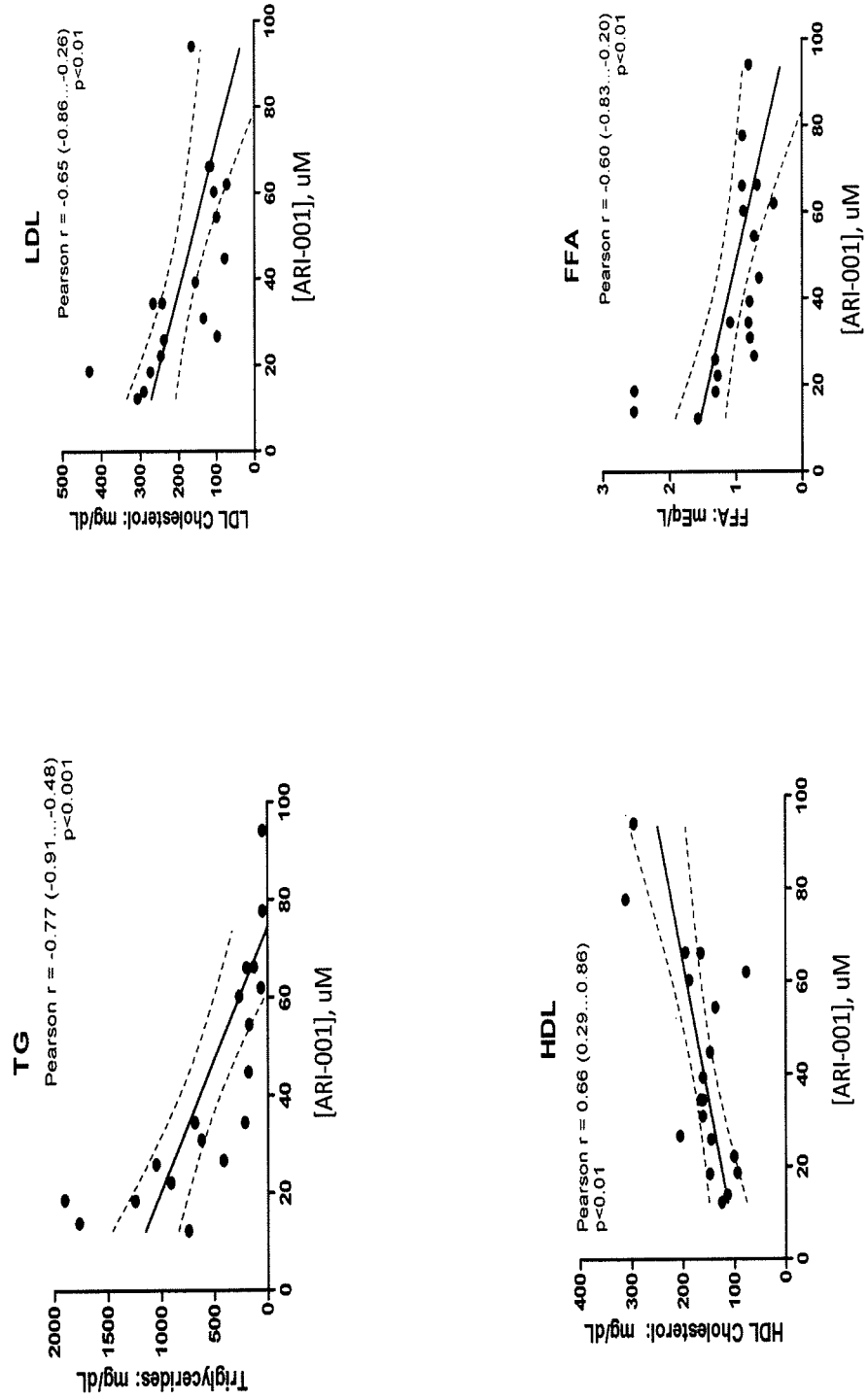

Plasma from the 19 hamsters dosed with ARI-001 in the above described 18-day study was analyzed for concentrations of ARI-001. Concentrations were determined for these samples, which were collected 24 hours after the final dose was administered. Briefly, plasma drug concentrations for the non-GLP pharmacokinetic experiments were determined by LC-MS using an Applied Biosystems 4000Qtrap spectrometer with electrospray ionization. Samples were prepared for analysis by precipitation of plasma proteins with cold methanol. HPLC of the samples was done with an Agilent Eclipse C18 column and a methanol/water gradient containing 0.1% formic acid and 5 mM ammonium acetate. ARI-001 was detected using multiple reaction monitoring (MRM) in the positive ion mode. For quantitation, a standard curve was measured by addition of known amounts of ARI-001 to plasma from untreated animals and preparing in a manner identical to the samples from treated animals. All plasma samples were spiked with 10 ng/mL of isotope-enriched ARI-001 which served as an internal standard for the LC-MS measurements. All compound concentrations are reported in µM. For correlation analysis, plasma concentrations of ARI-001 in a given animal were paired with that same animal's lipid parameter. All animals from both dosing groups (1120 mg/kg and 2240 mg/kg) were included in the analysis. These correlations are graphed in FIG. 6 and FIG. 7. Pearson r values were determined using all data points, as was the two-tailed P-value for the data set.

Lipid parameter changes correlated well with plasma levels of drug measured 24 hours after the final dose. Indeed, total cholesterol, HDL cholesterol, LDL cholesterol, triglycerides, and free fatty acid levels all achieved statistically significant levels of correlation ($p<0.01$). Correlation with triglycerides were especially notable for having a very high degree of statistical significance, $p<0.001$. These significant correlations give support to the idea that ARI-001 is directly responsible for modulation in lipid values. Moreover, these data corroborate the dose-response effects seen in FIG. 5.

ARI-001 Concentrations in Tissues Correlate with Plasma Lipid Levels.

Tissue samples were harvested from hamsters in the above-described 18-day experiment to determine the concentrations of ARI-001 in both liver and adipose tissue. Briefly, liver and adipose samples were harvested at the termination of the experiment; the samples were flash frozen in liquid nitrogen and then stored at −80° C. until used for analysis. To prepare for analysis, a sample of liver was excised from the frozen mass, weighed, and homogenized with a tissue grinder followed by sonication in buffer. The solid materials were then removed by centrifugation. To prepare for LC-MS analysis, the homogenate was then treated to the same preparation technique described for plasma preparation (vide supra). A sample of adipose was excised from the frozen mass, and transferred to a mortar and pestle cooled with liquid nitrogen. During grinding, liquid nitrogen was added to ensure the sample of adipose remained solid. The ground sample was transferred to a tared tube to weigh total sample. This ground sample was extracted with methanol, and this compound-containing methanol was separated from lipid by cooling to −20° C. After drying, the methanol sample was dissolved in water; the samples were then prepared for LC-MS analysis in the same way that liver and plasma were (vida supra).

Liver concentrations were reported as ng of ARI-001 per mL of homogenized tissue sample extracted into buffer. Concentrations in adipose were reported as ng of ARI-001 per mg of tissue recovered from the grinding process. Because of the distribution of tissue concentrations and lipid parameters, the logarithm transformation was used on all liver samples when determining correlation. Additionally, adipose concentrations were transformed as logarithm +1, since the logarithm transformation produced negative values for these tissue samples. These transformations allowed the data to be more graphed more conveniently. Finally, these transformations are valid because the nature of the Pearson r correlation coefficient is invariant to both logarithm transformation and to transposition.

Figure 8:
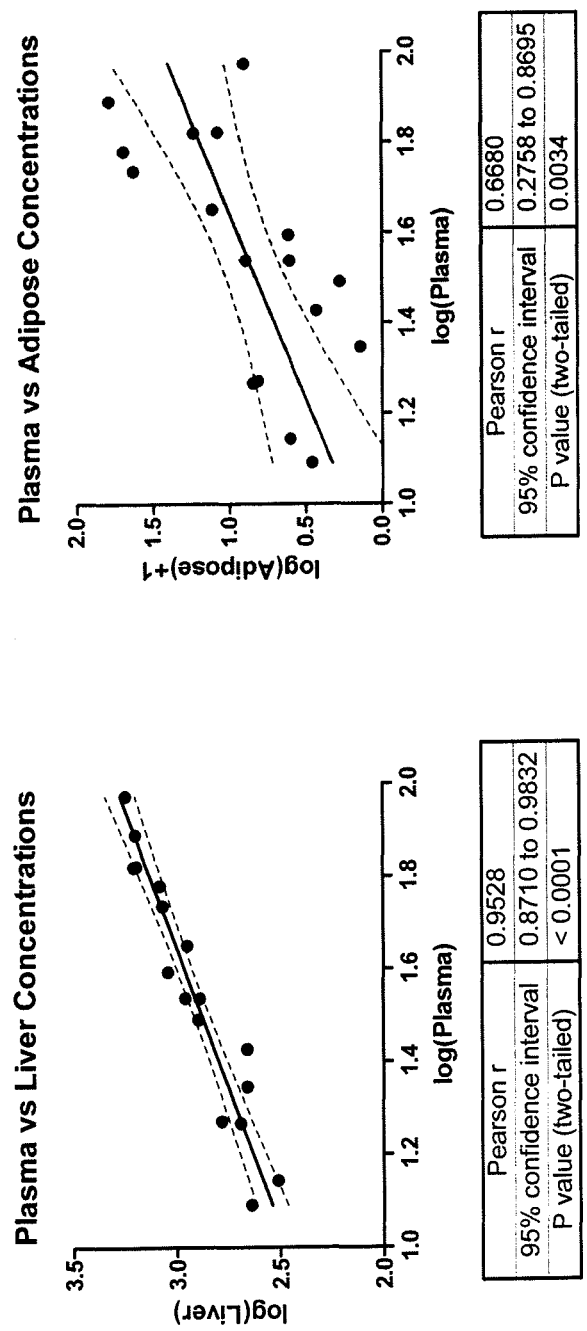
FIG. 8. (Left graph) Correlation between liver and plasma concentrations of ARI-001 in HF/HS hamsters dosed for 18 days. The values for each tissue have been transformed by logarithm, and therefore, the axes are unitless. (Right graph) Correlation between adipose and plasma concentrations in the same animals. Adipose concentrations have been transformed by the function "logarithm +1", which makes any values between −1 and 0 into positive values. This is done for clarity and does not otherwise distort the distribution of the data set.
Figure 9:
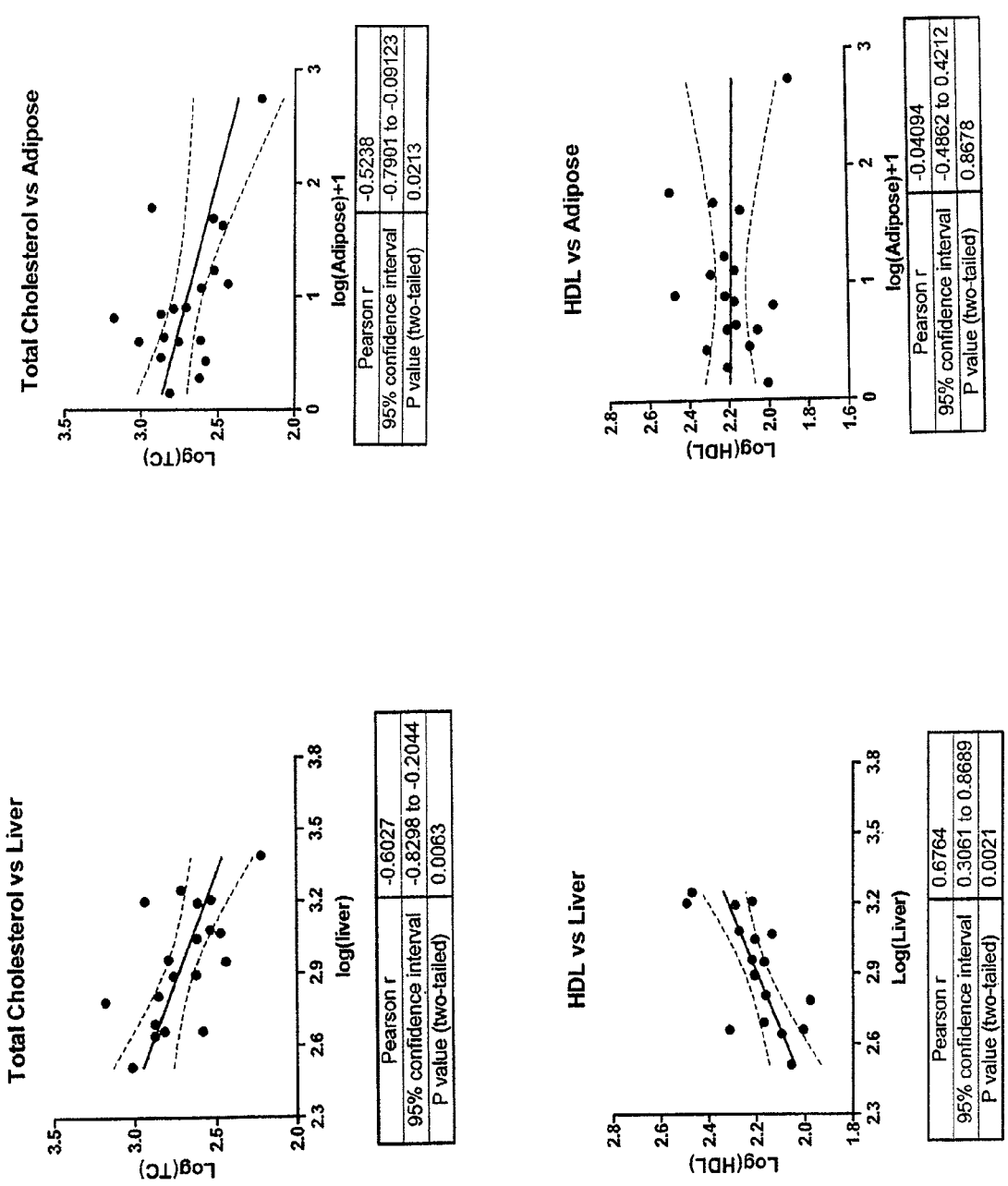
FIGS. 9-11. Correlations between liver concentrations of ARI-001 in HF/HS hamsters and values of different lipid parameters; also, correlations between adipose tissue concentrations of ARI-001 in HF/HS hamsters and values of different lipid parameters. All values are the logarithm of the lipid values versus the logarithm of the tissue concentrations. Correlations are between tissue concentration and lipid values in the same animals. Adipose concentrations have been transformed by the function "logarithm +1", which makes any values between −1 and 0 into positive values. This is done for clarity and does not otherwise distort the distribution of the data set.
Figure 10:
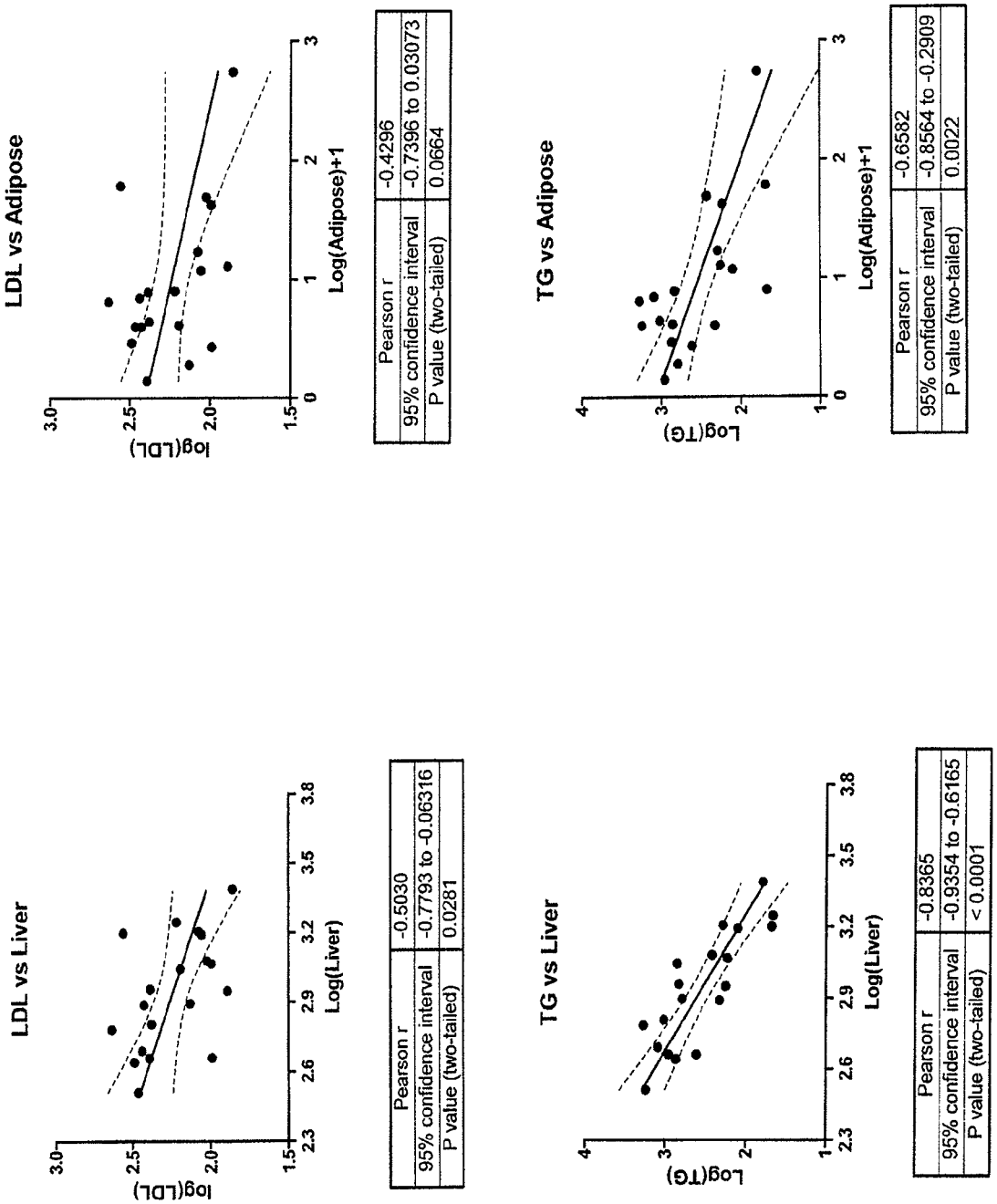
Figure 11:
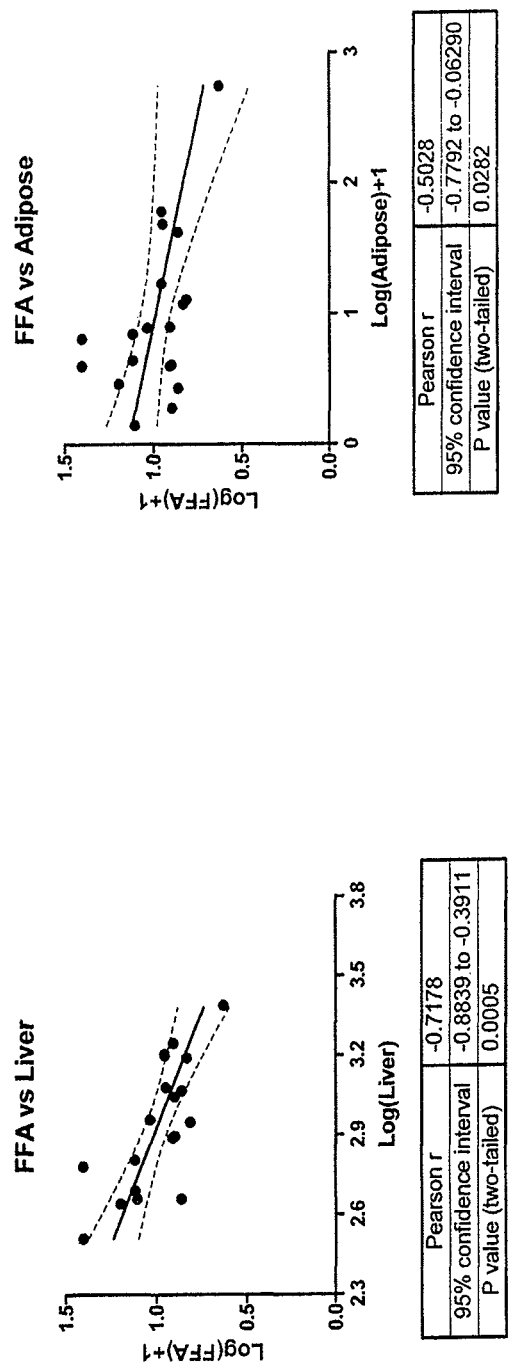

FIG. 8 graphs the correlation between concentrations of ARI-001 in plasma versus liver (left), and in plasma versus adipose (right). Both of these correlations were highly statistically significant, with $p<0.01$ for each pair of parameters. FIGS. 9-11 graph the correlations between the concentrations of ARI-001 in each tissue sample versus the lipid parameters TC, HDL, LDL, TG, and FFA. All concentration measurements and all lipid parameters were transformed via logarithm. Pearson r was determined using all data points illustrated. P-value was determined for a 2-tailed t-test using all data points illustrated.

ARI-001 Increases ABCA1, ApoAI, SR-BI, CETP, and Adiponectin mRNA in HF/HS Hamsters.

Investigation of a possible mechanism that could lead to the increase in HDL cholesterol focused on changes in the mRNA levels of several genes related to the regulation of HDL. Hamster livers and adipose were preared in manners similar to that described for ARI-001 concentration determination. Briefly, to prepare for analysis, a sample of liver was excised from the frozen mass, weighed, and homogenized with a tissue grinder followed by sonication in buffer. The solid materials were then removed by centrifugation. The resulting lysate was used in qPCR analysis to quantify the specific mRNA measured (vide infra) using primers designed for the specific sequences of interest. All mRNA quantities were normalized to vehicle-treated animal, and mRNA levels were expressed as a fold increase or decrease relative to vehicle-treated. The adipose was treated in a similar manner to the liver: a sample of adipose was excised from the frozen mass, and transferred to a mortar and pestle cooled with liquid nitrogen. During grinding, liquid nitrogen was added to ensure the sample of adipose remained solid. The ground sample was transferred to a tared tube to weigh total sample. This ground sample was treated with buffer and prepared for qPCR to quantify specific mRNA quantities.

TABLE 5

Relative concentrations of ABCA1, ApoAI, SR-BI, CETP mRNA per mg of liver tissue, and likewise adipose CETP and adiponectin mRNA per mg of adipose tissue, from high fat-fed hamsters in vehicle-, niacin-, or ARI-001-treated cohorts. Values are given as a fold-change compared to the mean of the vehicle values.

| Message | Vehicle | Niacin: 1200 mg/kg | ARI-001: 2240 mg/kg |
|---|---|---|---|
| Liver ABCA1 | 1.02 ± 0.18 | 0.80 ± 0.18 | 1.54 ± 0.48** |
| Liver ApoAI | 1.04 ± 0.28 | 1.17 ± 0.19 | 1.72 ± 0.24*** |
| Liver SR-BI | 1.00 ± 0.25 | 0.79 ± 0.18 | 1.50 ± 0.33** |

TABLE 5-continued

Relative concentrations of ABCA1, ApoAI, SR-BI, CETP mRNA per mg of liver tissue, and likewise adipose CETP and adiponectin mRNA per mg of adipose tissue, from high fat-fed hamsters in vehicle-, niacin-, or ARI-001-treated cohorts. Values are given as a fold-change compared to the mean of the vehicle values.

| Message | Vehicle | Niacin: 1200 mg/kg | ARI-001: 2240 mg/kg |
|---|---|---|---|
| Liver CETP | 1.00 ± 0.45 | 1.03 ± 0.55 | 2.05 ± 0.38*** |
| Adipose CETP | 1.00 ± 0.46 | 1.12 ± 0.33 | 1.72 ± 0.70* |
| Adipose Adiponectin | 1.00 ± 0.43 | 1.67 ± 0.32*** | 2.00 ± 0.23*** |

Both ABCA1 and ApoAI mRNA levels were higher in the ARI-001-treated arms relative to vehicle control animals. Indeed, a statistically significant correlation was seen between HDL and ApoAI mRNA levels. This suggests a possible mechanism by which ARI-001 may increase HDL in this hamster model.

TABLE 6

Correlations between ABCA1, ApoAI, SR-BI, and CETP mRNA per mg of liver tissue vs HDL levels, and likewise between CETP and adiponectin mRNA per mg of adipose tissue vs HDL levels, from high fat-fed hamsters in vehicle-, niacin-, or ARI-001-treated cohorts.

| Correlation | Vehicle | Niacin: 1200 mg/kg | ARI-001: 2240 mg/kg |
|---|---|---|---|
| [HDL] vs Liver ABCA1 | −0.007 (−0.60 … 0.60) | −0.40 (−0.84 … 0.36) | 0.49 (−0.33 … 0.89) |
| [HDL] vs Liver ApoAI | 0.32 (−0.34 … 0.77) | 0.19 (−0.54 … 0.76) | 0.80 (0.21 … 0.96)* |
| [HDL] vs Liver SR-BI | 0.46 (−0.19 … 0.83) | 0.46 (−0.29 … 0.86) | −0.10 (−0.75 … 0.65) |
| [HDL] vs Liver CETP | 0.18 (−0.47 … 0.70) | −0.13 (−0.73 … 0.58) | 0.30 (−0.52 … 0.83) |
| [HDL] vs Adipose CETP | −0.03 (−0.62 … 0.58) | 0.54 (−0.19 … 0.89) | 0.85 (0.28 … 0.98)* |
| [HDL] vs Adipose Adiponectin | 0.43 (−0.22 … 0.82) | 0.31 (−0.48 … 0.81) | −0.22 (−0.83 … 0.64) |

Example 4

Safety Pharmacology Studies (Non-GLP Preliminary Studies)

Because niacin is known to be associated with liver toxicity and glucose intolerance in a chronic dosing setting, we examined whether ARI-001, a niacin mimetic, could be associated with similar issues. In order to investigate this, we examined the common liver functional enzymes AST and ALT in the plasma of hamsters from experiment described above in Example 3. These animals were dosed for 18 consecutive days, while being on a HF/HS diet for a total of nearly 5 weeks. We also examined the glucose levels in the plasma of these animals. For pharmacokinetic studies, we utilized wild type mice for both single and repeated administration study. Finally, pharmacokinetic studies were corroborated by data from single and repeated administration to monkeys.

A. Effects on Liver Function

ARI-001 Improves Liver Function Tests from Chronically Dosed High Fat-Fed Hamsters.

Figure 12A:
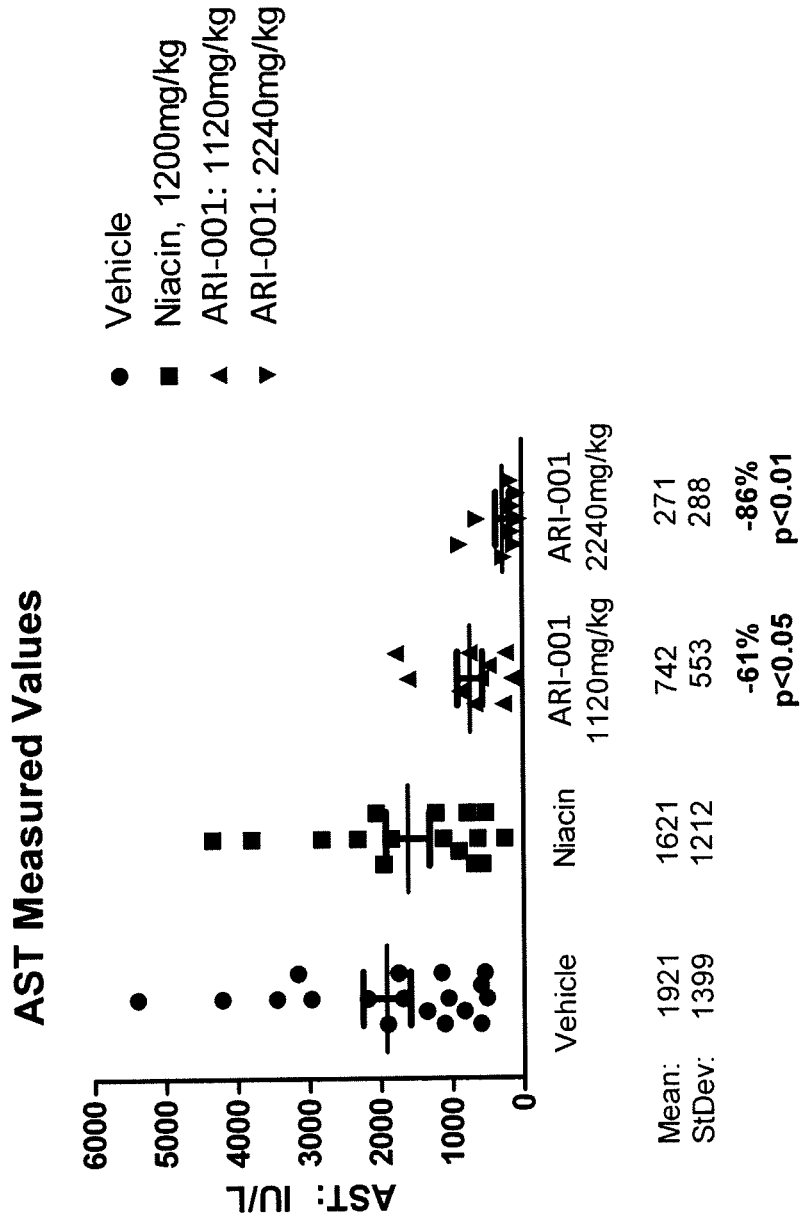
FIGS. 12A and B. Liver function test parameters from high fat-fed hamsters dosed orally with vehicle, niacin, or ARI-001 for 18 days. Percent changes are given relative to vehicle. P-values are reported from 2-tailed unpaired t-tests comparing to vehicle.
Figure 12B:
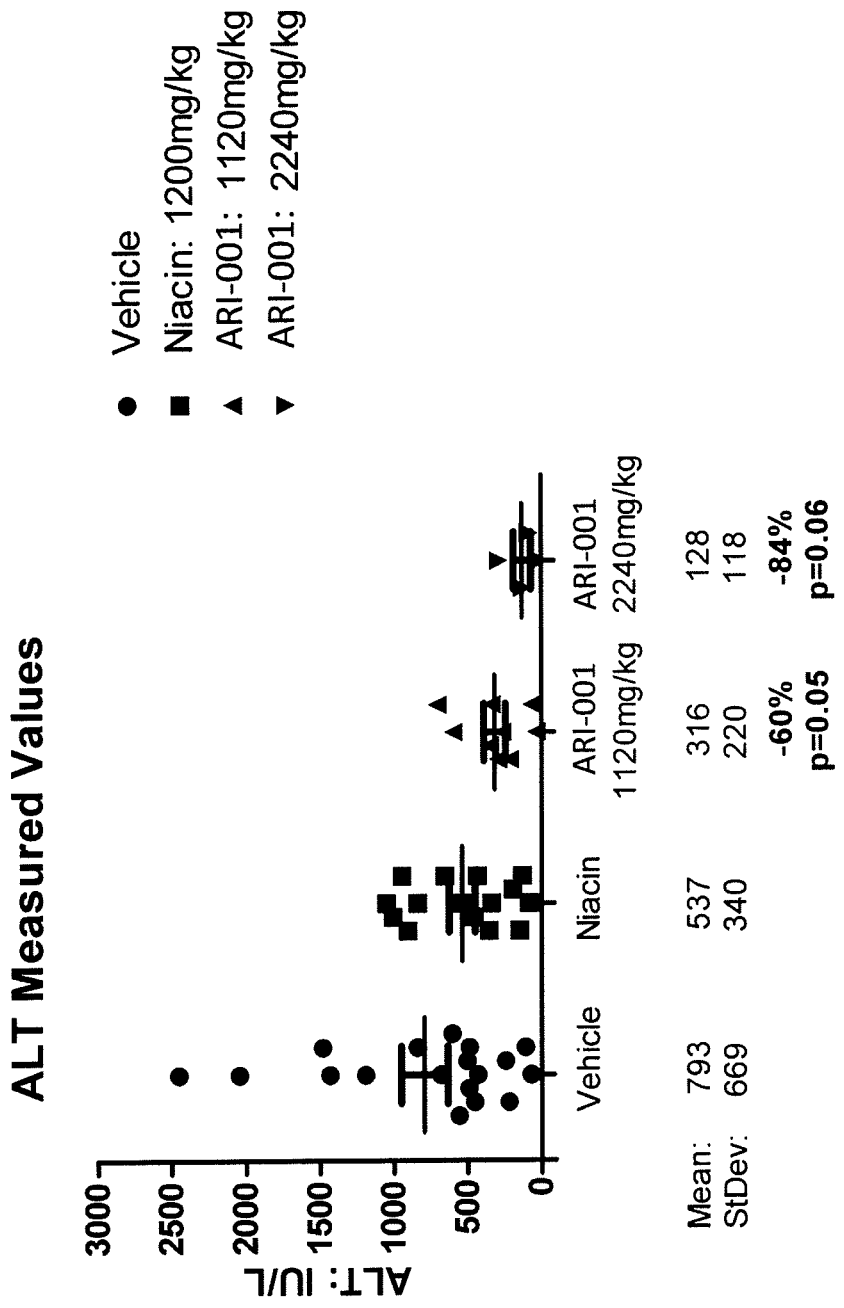
FIG. 12B, alanine aminotransferase (ALT).

Certain formulations of niacin are known to cause hepatotoxicity in humans. This led to an investigation of liver function tests (AST, ALT) from plasma of hamsters dosed for 18 days with ARI-001. AST and ALT were measured using commercially available kits (Bio-Quant Diagnostic Kits, San Diego, Calif.). As expected, AST and ALT values from untreated hamsters (vehicle group) were very high, as the high fat diet leads to hepatomegaly and fatty liver. This disease state is reflected in the elevated AST and ALT levels. In contrast, AST and ALT levels from ARI-001 treated animals were significantly lower than vehicle. Indeed, AST was drastically reduced at the 2240 mg/kg dose, and even significantly reduced at the 1120 mg/kg dose. ALT values were similarly reduced, again in a dose-dependent manner. See FIG. 12A and FIG. 12B.

B. Effects on Glucose Tolerance

ARI-001 has No Effect on Glucose Levels Among High Fat-Fed Hamsters.

Figure 13:
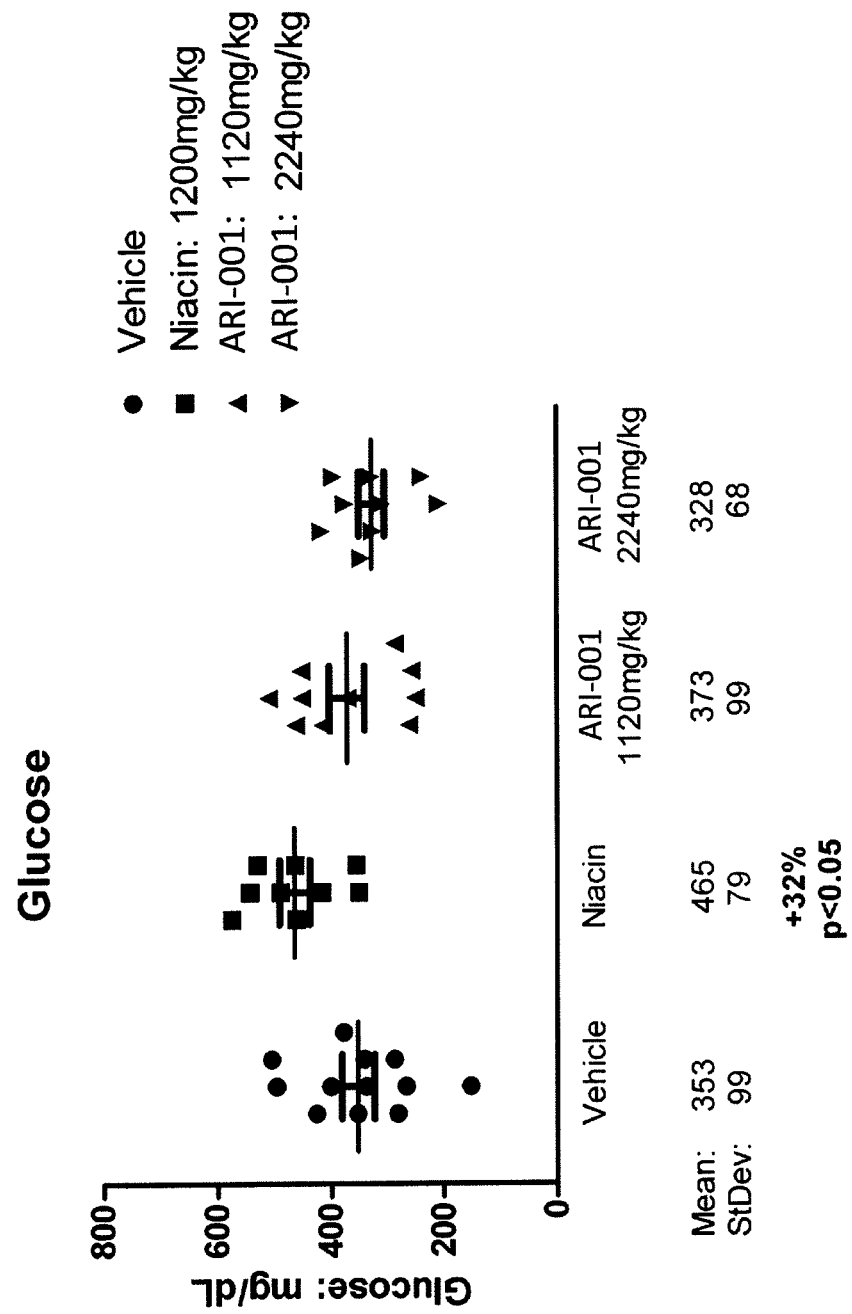
FIG. 13. Glucose values measured in plasma from an 18 day study of HF/HS hamsters dosed daily with vehicle, niacin, or ARI-001. Percent changes are reported in comparison to the vehicle group values. P-value is determined from a 2-tailed t-test.

Niacin is known to adversely affect glucose levels among diabetic patients. The hamster model used in this experiment did produce a population with elevated glucose levels, as demonstrated by the vehicle group in FIG. 13. Consistent with effects seen in humans, the glucose of niacin-treated animals was increased relative to vehicle. However, neither dose of ARI-001 produced any significant change in glucose levels in comparison to the vehicle cohort.

Example 5

Pharmacokinetic Studies

A. Mouse In Vivo Studies

Single-Dose Pharmacokinetic Study of ARI-001 in Wild Type Mice.

Figure 14:
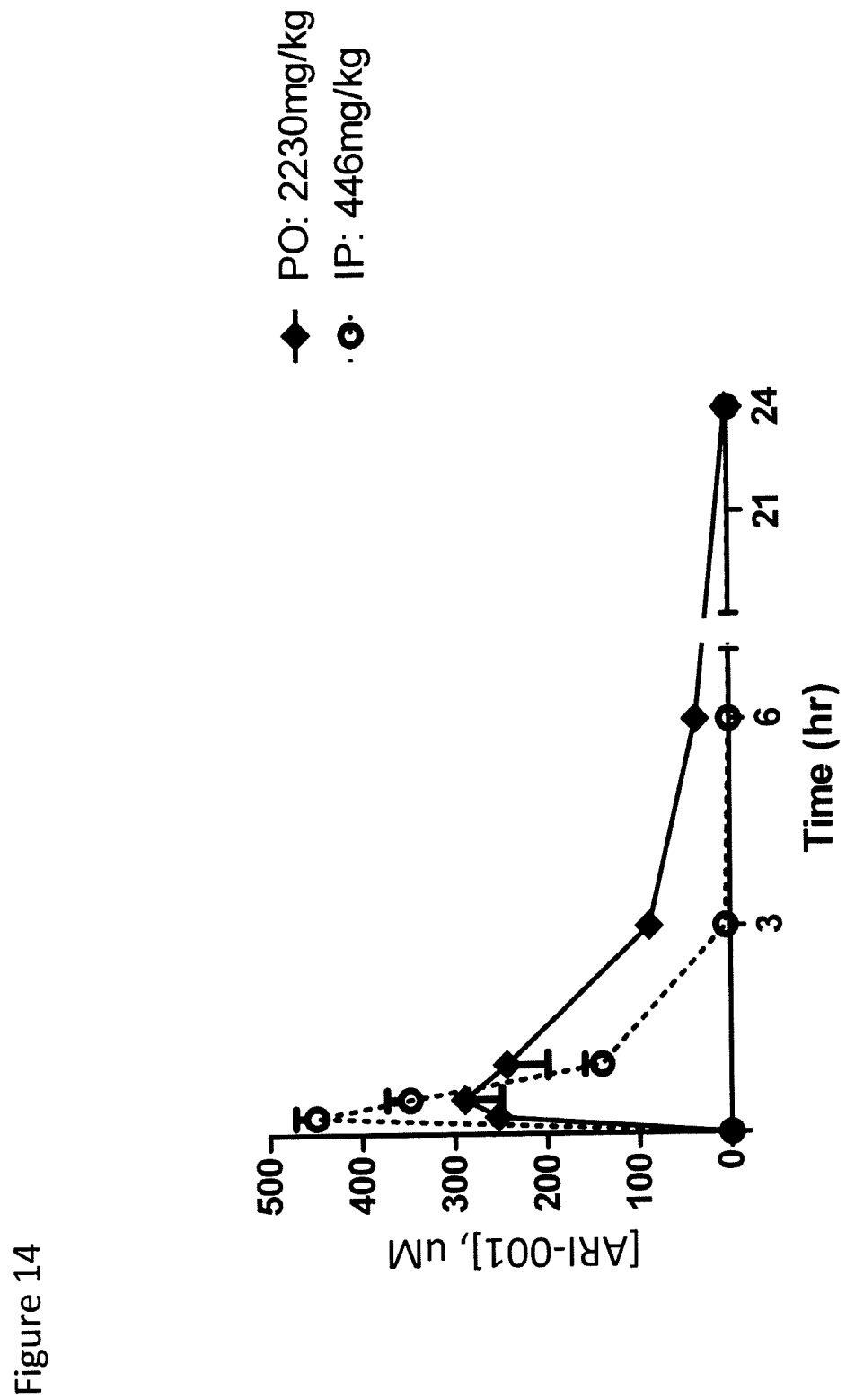
FIG. 14. Plasma concentrations of ARI-001 from mice dosed with a single administration of ARI-001 either orally (PO) or intraperitoneally (IP).
Figure 15A:
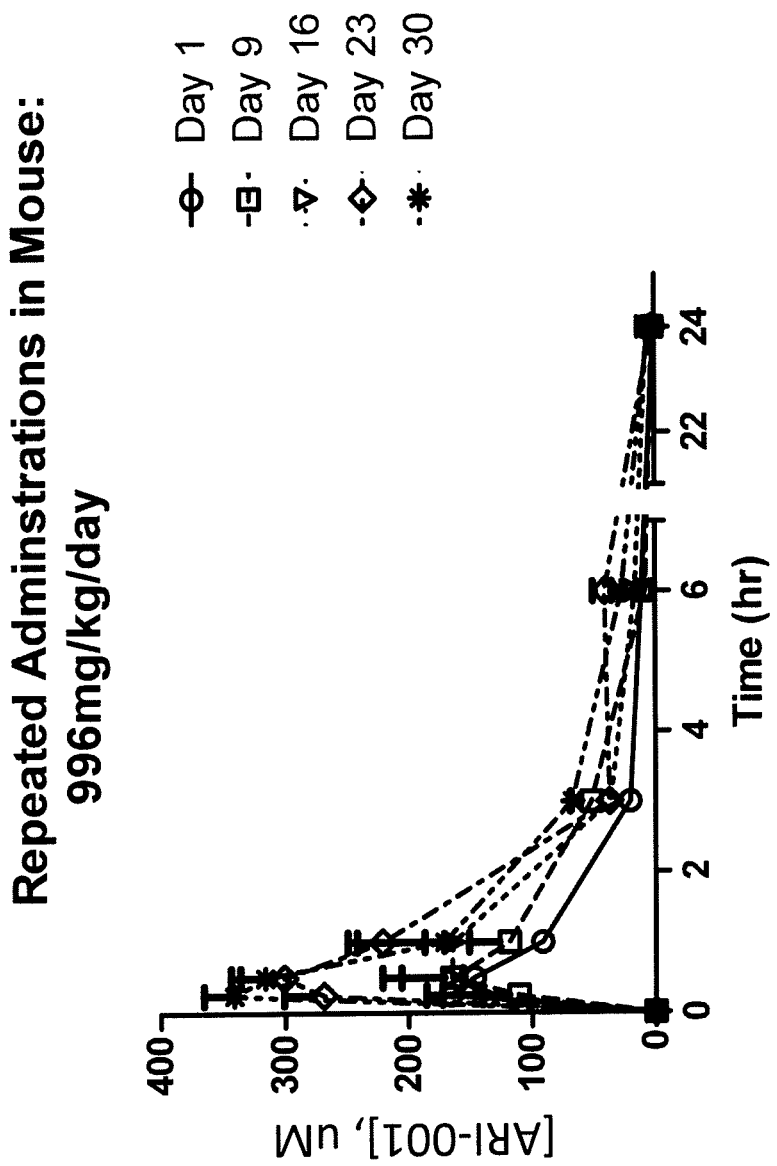
FIGS. 15A-15D. Plasma concentrations of ARI-001 from mice dosed with multiple daily oral administrations of ARI-001 for 30 consecutive days. Four different doses were used. Each mouse received the same indicated dose of ARI-001 every day for 30 days.
Figure 15B:
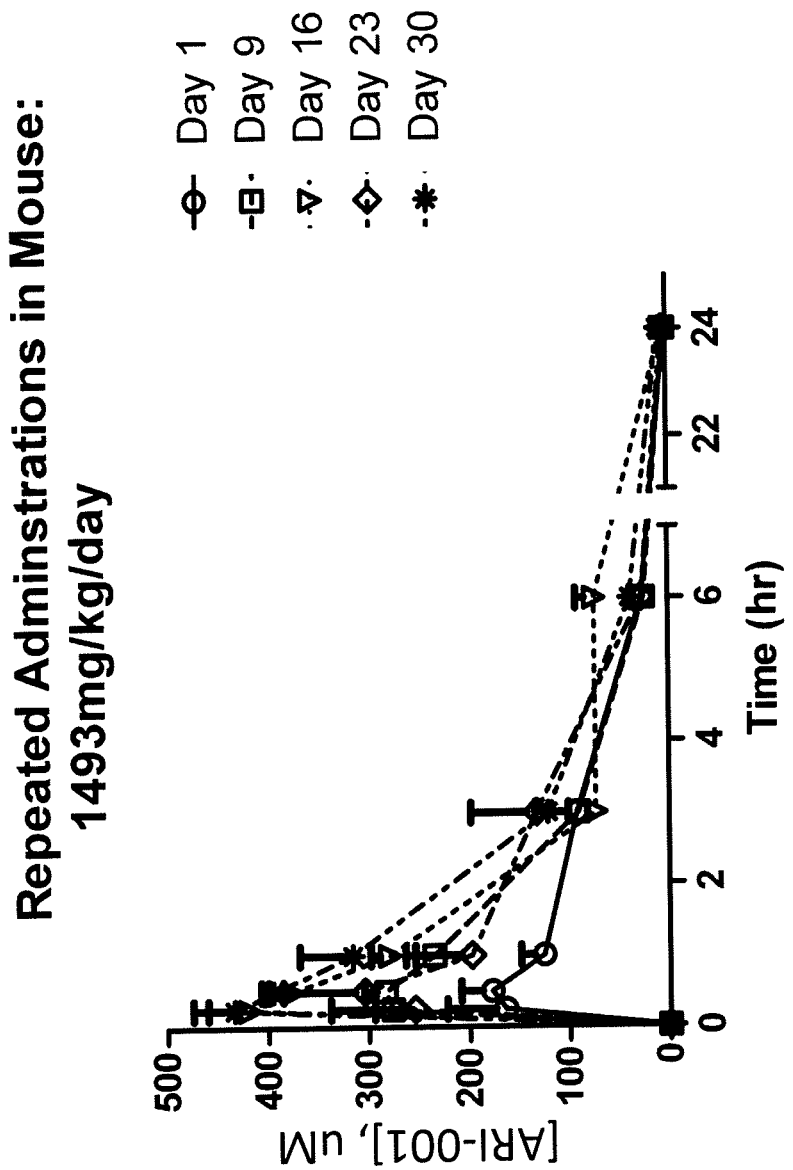
Figure 15C:
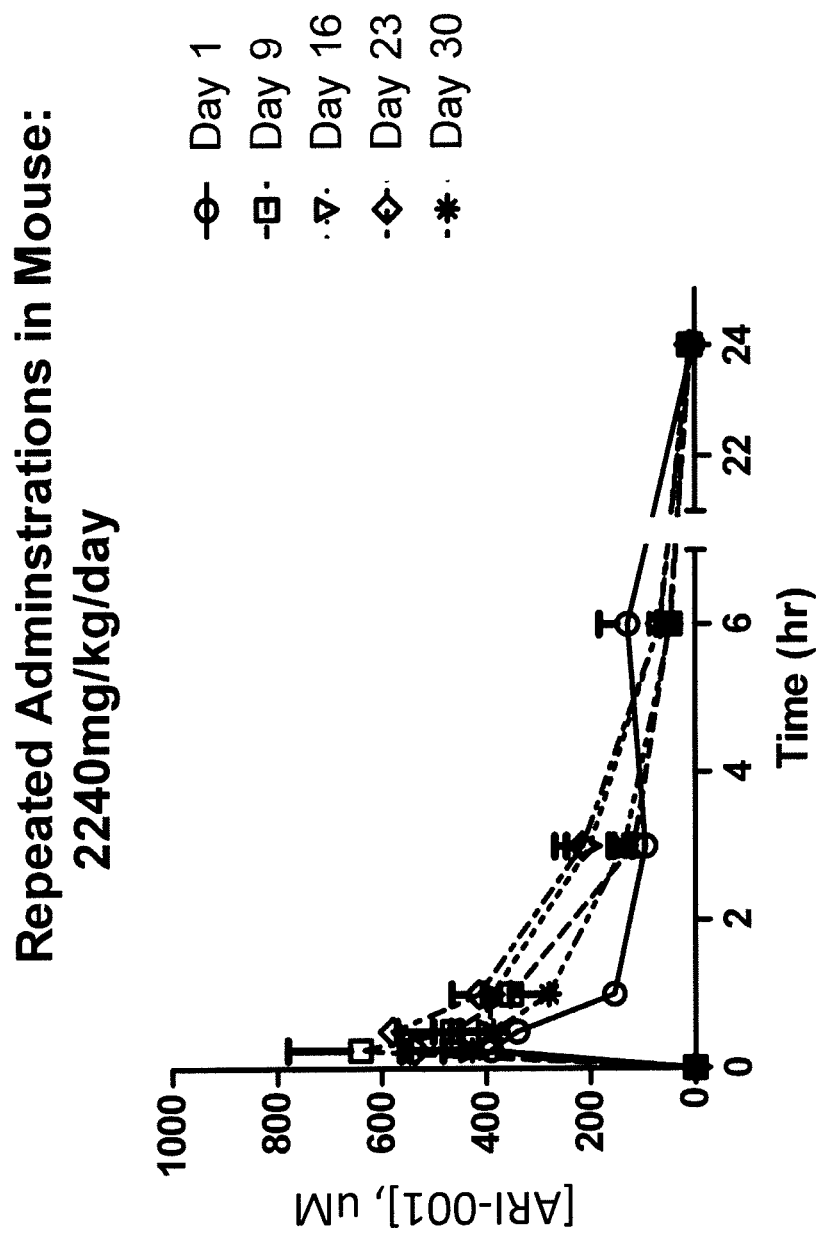
Figure 15D:
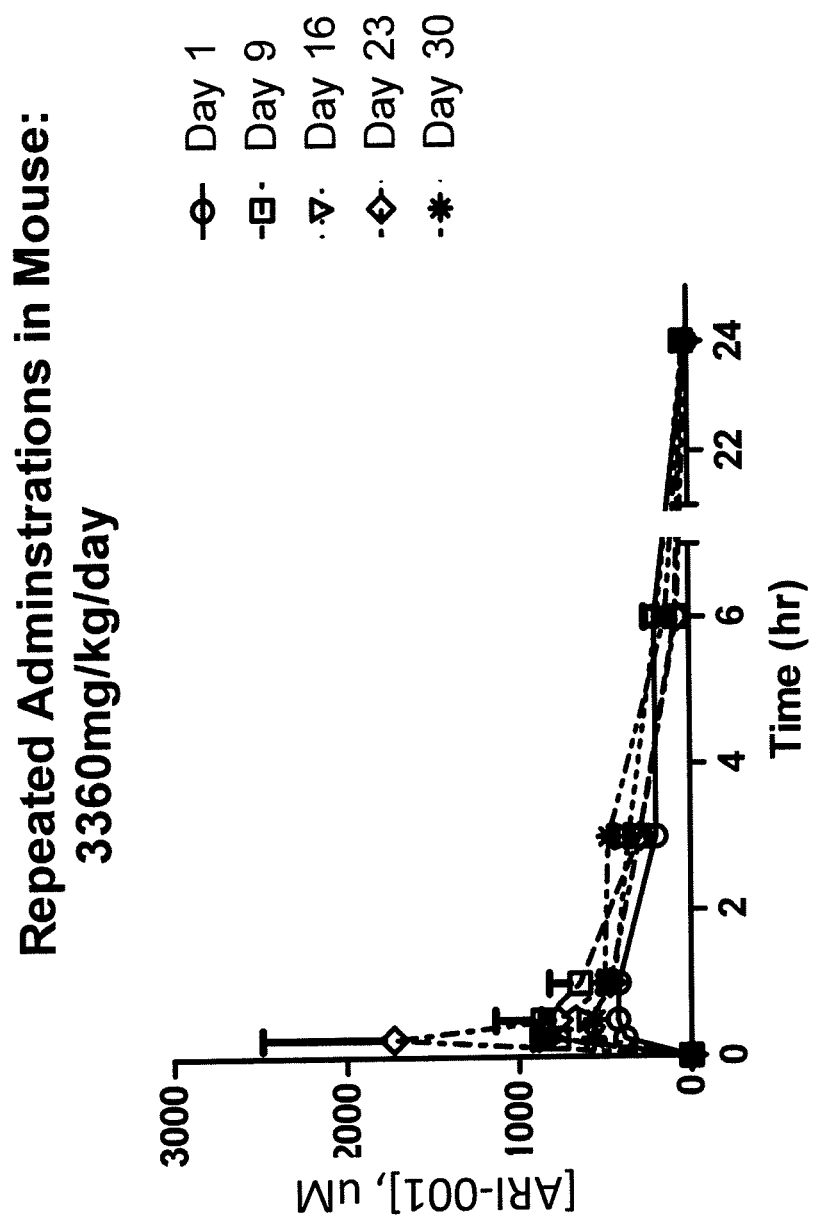
Figure 16A:
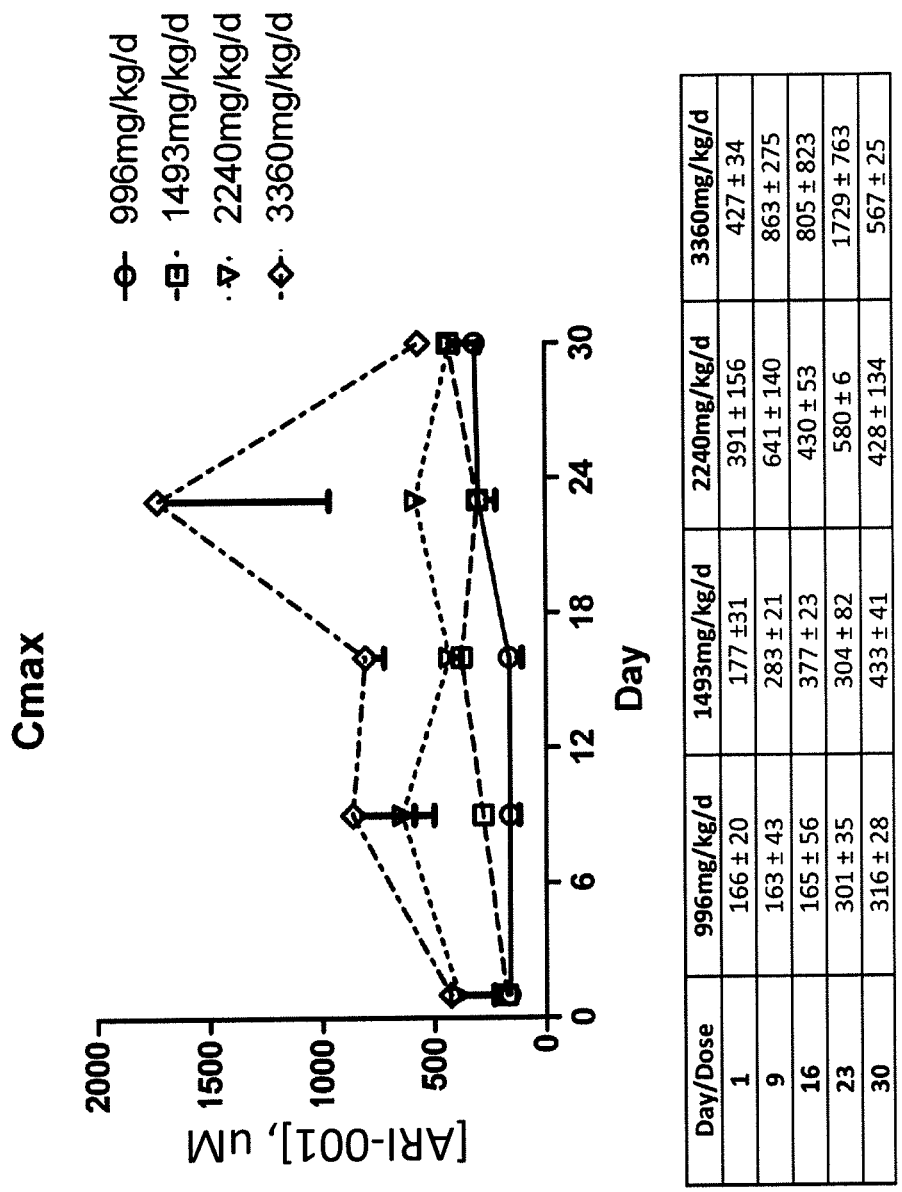
FIGS. 16A and 16B. Summary of $C_{max}$ and AUC parameters for ARI-001 from 30-day multiple administration study in wild type mice. Values are plotted as the mean with standard error. There was no significant change in either parameter as a function of time. (○) 996 mg/kg/d; (□) 1493 mg/kg/d; (▽) 2240 mg/kg/d; (◇) 3360 mg/kg/d.
Figure 16B:
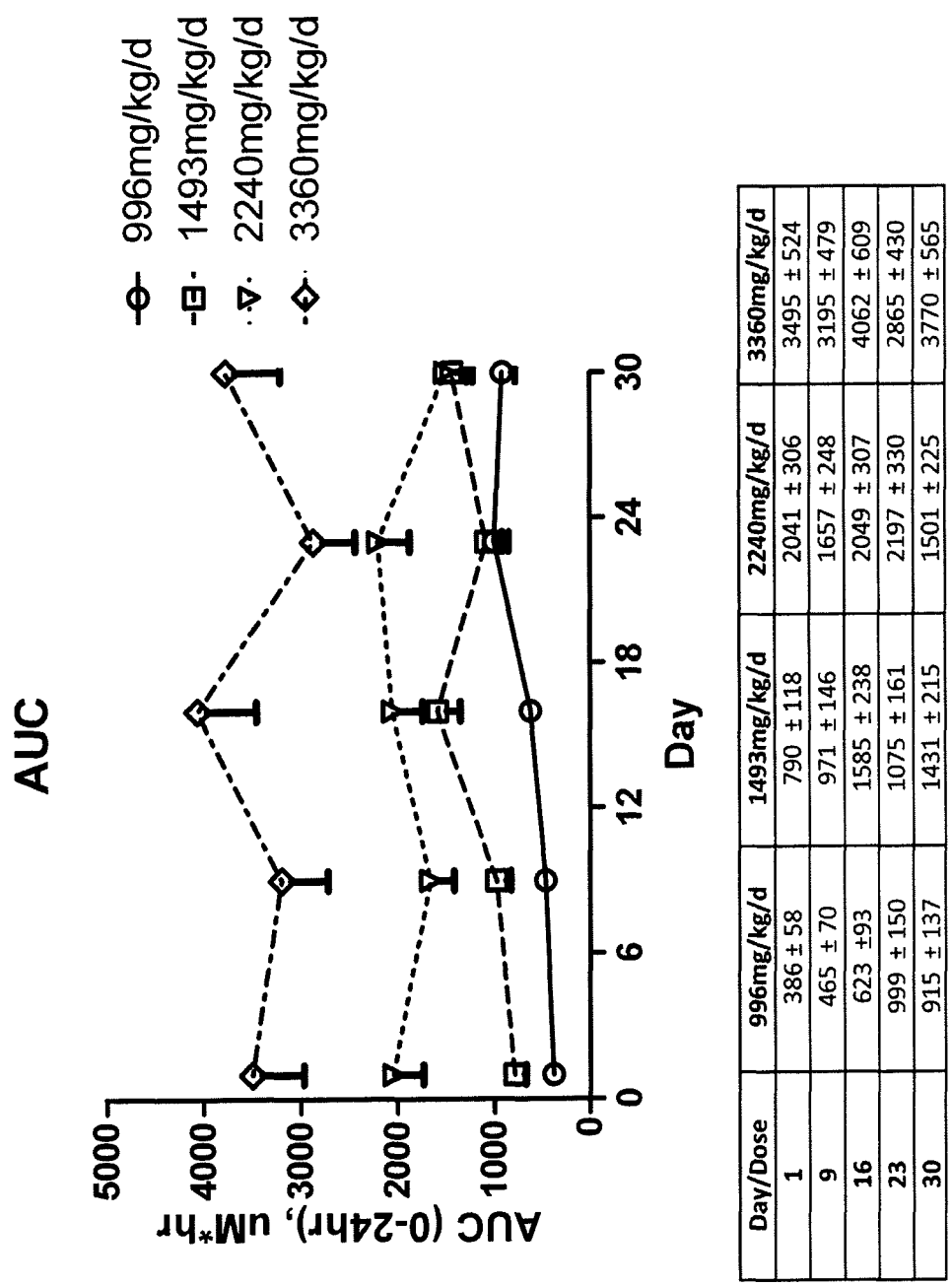

Wild type C57BL/6 mice were dosed with a single administration of ARI-001 in solution either via oral gavage (PO) or via intraperitoneal injection (IP). Blood samples were then collected at various time points over a 24-hour period; plasma was then analyzed for concentrations of ARI-001 as described earlier. ARI-001 was administered at either a dose of 2240 mg/kg as a single bolus via oral gavage, or a dose of 448 mg/kg as a single bolus via intraperitoneal injection. See FIG. 14.

Single-dose administration of ARI-001 via oral gavage and intraperitoneal injection produced pharmacokinetic curves with parameters described in Table 7. By the 24 hour timepoint, the remaining concentration of ARI-001 was undetectable.

TABLE 7

Pharmacokinetic parameters from single administration of ARI-001 in wild type mice.

| ARI-001 | $C_{max}$ (μM) | $t_{1/2}$ (h) | $t_{max}$ (h) | AUC (μM * h) |
|---|---|---|---|---|
| PO | 289 | 1.5 | 0.5 | 1096 |
| IP | 450 | 0.5 | 0.25 | 439 |

Multiple Administration Pharmacokinetic Study of ARI-001 in Wild Type Mice.

Wild type C57BL/6 mice were dosed with ARI-001 in solution via oral gavage daily for 30 consecutive days. Over the course of five 24-hour periods, blood was collected, and the resultant plasma was analyzed for concentrations of ARI-001. Four doses were used: 996 mg/kg, 1493 mg/kg, 2240 mg/kg, and 3360 mg/kg. As expected, $C_{max}$ levels and total 24-hour exposure (AUC) were dose-dependent. However, these values were time-independent, as there was no trend observed between these parameters and days of administration. See FIGS. 15A-15D and FIGS. 16A-16B.

B. Further Mouse In Vivo Studies

Single-Dose Pharmacokinetic Study in Wild Type Mice.

Wild type C57BL/6 mice were dosed with a single administration of niacin, ARI-001, or compound 2230C (disclosed in US Patent Application Pub. No. 2009/0312355 A1, incorporated herein by reference) in solution via single bolus oral gavage (PO). Compound 2230C has the structure

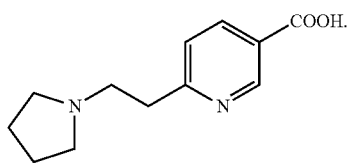 [SMILES: O=C(O)c1ccc(CCN2CCCC2)nc1]

Blood samples were then collected at various time points over a 24-hour period; plasma was then analyzed for concentrations of niacin, ARI-001, and 2230C as described earlier. Results are shown in Table 8.

TABLE 8

Comparison of pharmacokinetic parameters of niacin, ARI-001, and 2230C from single oral administration in wild type mice.

|  | Niacin | ARI-001 | 2230C |
|---|---|---|---|
| $C_{max}$ (µM) | 4,089 | 309 | 126 |
| AUC (µM h) | 11,696 | 1,097 | 686 |
| half-life ($t_{1/2}$) (h) | 1.75 | 1.43 | 3.47 |
| $t_{max}$ (h) | 0.50 | 0.38 | 0.31 |
| $C_{max}$ (% Niacin) | 100 | 7.5 | 3.0 |
| AUC (% Niacin) | 100 | 9.4 | 5.8 |
| $C_{max}/AUC_{0-24}$ (h$^{-1}$) | 0.35 | 0.28 | 0.18 |
| $C_{24h}/C_{max}$ (%) | 0.02 | n.d. | 2.1 | n.d., not done

C. Golden Syrian Hamster In Vivo Studies

Single-Dose Pharmacokinetic Study of ARI-001 in Golden Syrian Hamsters.

Figure 17:
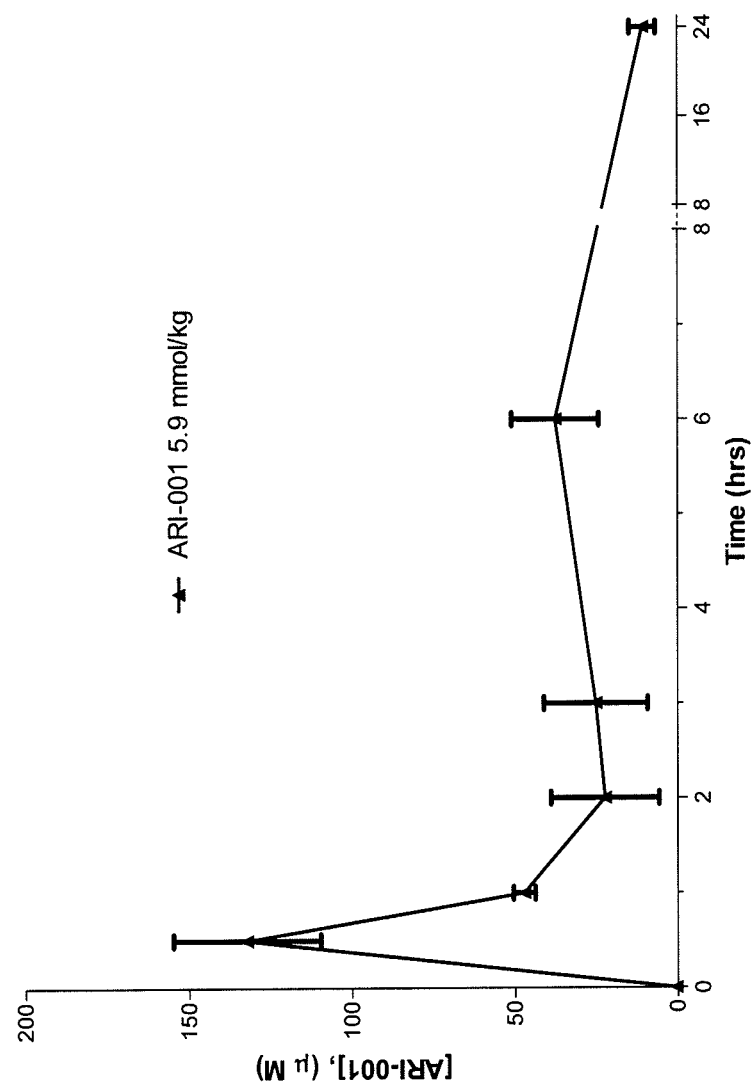
FIG. 17. Plasma concentrations of ARI-001 in Golden Syrian Hamsters on high fat/high sugar diet after single administration of ARI-001 at 5.9 mmol/kg.

The pharmacokinetic profile of ARI-001 was evaluated in HF/HS Golden Syrian hamsters given aa single oral dose of 5.9 mmol/kg of ARI-001. Plasma samples were collected via cardiac puncture from five animals at each time point to measure plasma concentrations of ARI-001 over 24 hours. Results are shown in FIG. 17.

D. Monkey In Vivo Studies

Single-Dose Pharmacokinetic Study of ARI-001 in Macaque Monkeys.

Figure 18:
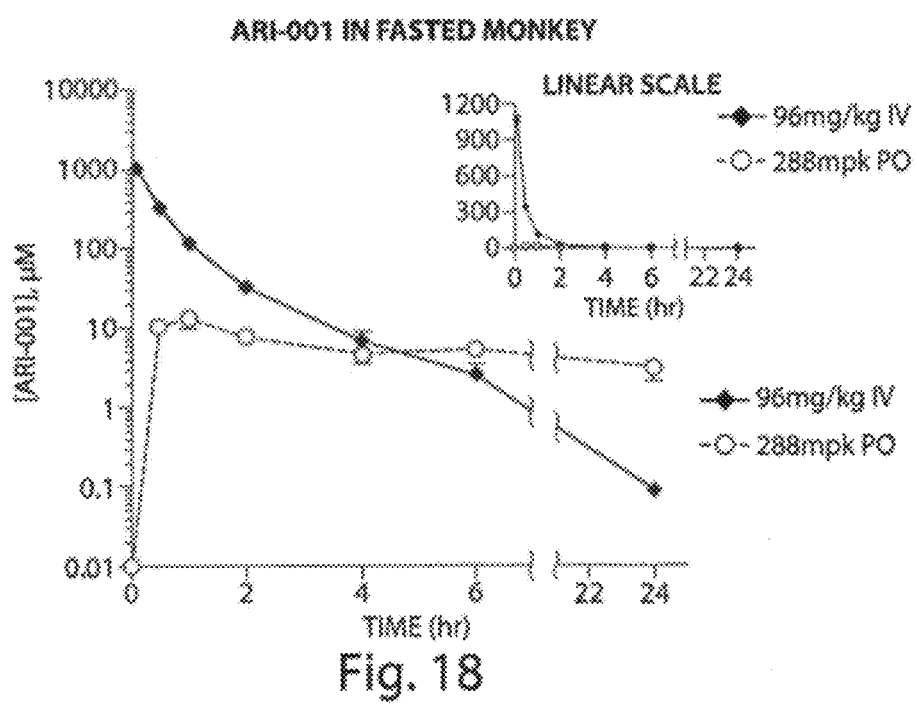
FIG. 18. Plasma concentrations of ARI-001 in fasted monkeys after single administration of ARI-001 either (♦) 96 mg/kg intravenously (IV) or (○) 288 mg/kg (mpk) orally (PO). Y-axis is logarithmic scale for clarity. (Inset): Same data, with the y-axis on a linear scale.

Fasted monkeys were given a single administration of ARI-001 in solution either via oral gavage (PO) or via intravenous injection (IV). Blood samples were collected at various time points over a 24-hour period; plasma was then analyzed for concentrations of ARI-001. ARI-001 was administered at either a dose of 288 mg/kg as a single bolus via oral gavage, or a dose of 96 mg/kg as a single bolus via IV injection. Results are shown in FIG. 18.

Single-Dose Pharmacokinetic Study of ARI-001 in Fed or Fasted Monkeys.

Figure 19:
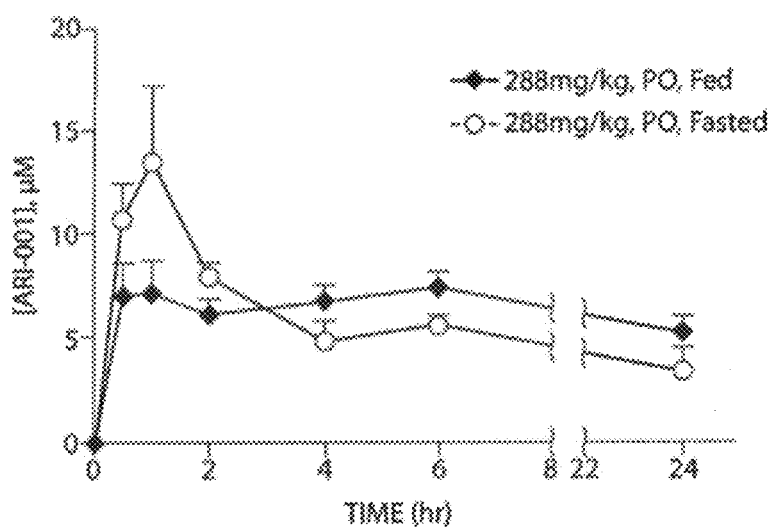
FIG. 19. Plasma concentrations of ARI-001 after single administration of 288 mg/kg orally to (♦) fed monkeys or to (○) fasted monkeys. Values are mean with standard error.

Fed monkeys were fed and allowed some time to digest before being administered ARI-001 as a solution via oral gavage as previously described. Results are shown in FIG. 19.

Pharmacokinetics of Multiple Administrations of ARI-001 to Fasted Monkeys.

Figure 20:
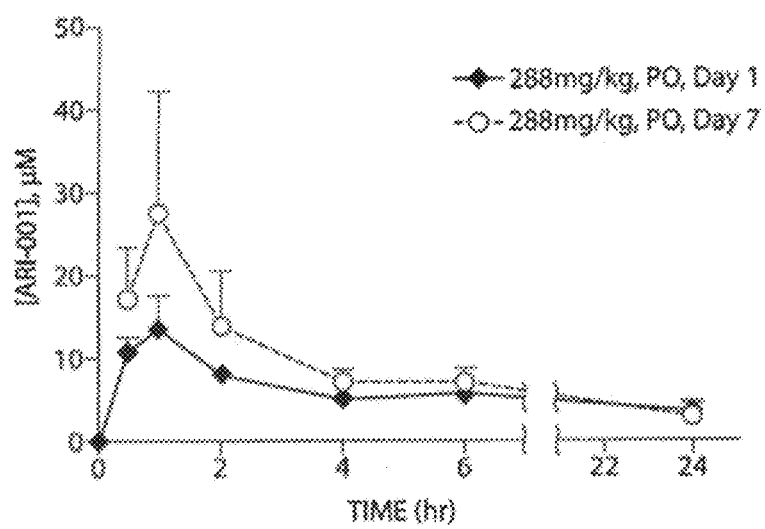
FIG. 20. Plasma concentrations of ARI-001 after repeated daily administration of 288 mg/kg orally to fasted monkeys. Values are mean with standard error. (♦) Samples drawn on day 1. (○) Samples drawn on day 7.

ARI-001 was administered to monkeys via oral gavage once per day for a total of seven days. Blood samples were collected after the first and after the last administrations to measure plasma concentrations of ARI-001. There was very little difference between the plasma concentrations on day 1 versus day 7. The greatest point of discrepancy was in the $C_{max}$ value, which was higher on day 7 than on day 1. The concentrations 24 hours after either the first or the last doses were essentially identical. See FIG. 20.

Example 6

Figure 21:
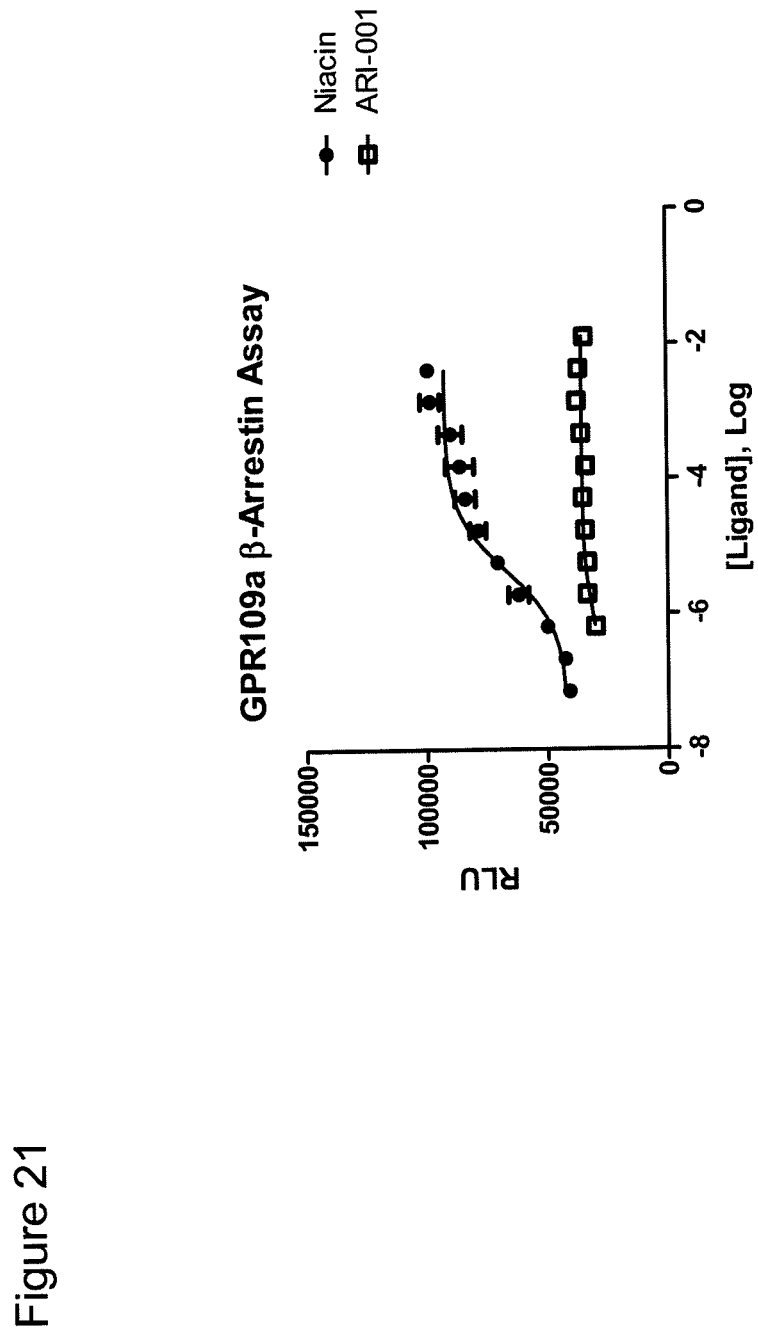
FIG. 21. ARI-001 fails to recruit beta-arrestin to the cell membrane of cells expressing the niacin receptor GPR109A. Ligand refers to niacin or ARI-001, as indicated. RLU, relative light units, as measured in chemiluminescent read-out for G protein-coupled receptor activity.

ARI-001 Fails to Recruit β-Arrestin to the Cell Membrane of Cells Expressing High Affinity Niacin Receptor GPR109A It has been demonstrated that niacin-induced cutaneous flushing is mediated by activation of the niacin receptor, GPR109A, in a β-arrestin-dependent manner. Walters R W et al. (2009) *J Clin Invest* 119:1312-21. Assay-ready PathHunter eXpress β-Arrestin cells expressing GPR109A were plated at 10,000 cells/well in a 96-well plate and stimulated with either niacin or ARI-001, each over a range of concentrations, for 90 minutes. G protein-coupled receptor (GPCR) activity was detected by measuring the interaction of β-arrestin with the activated GPCR using β-galactosidase enzyme fragment complementation. Following stimulation with either niacin or ARI-001, signal was detected using the chemiluminescent PathHunter Detection Reagents. Representative results are shown in FIG. 21.

Unlike niacin, stimulation of GPR109A with ARI-001 at concentrations up to 10 mM failed to recruit β-arrestin to the membrane of cells expressing GPR109A. Since niacin-induced flushing is known to be mediated by activation of GPR109A in a β-arrestin-dependent manner, this finding is consistent with the observation that ARI-001 has greatly reduced flushing side effect compared to niacin.

Example 7

Summary of Pharmacological Studies of ARI-001 in Animal Models

A number of pharmacokinetic, safety, and efficacy studies for ARI-001 have been completed in a variety of animals, including mice, rats, Golden Syrian hamsters, dogs, and monkeys. Overall, results from these studies have established the following.

ARI-001 decreased plasma levels of total cholesterol, LDL-C, TG and FFA while increasing the absolute level of HDL-C and HDL-C/TC ratio. The lipid altering effects of a once-daily dose of ARI-001 were more pronounced than the lipid effects observed with nearly 2-fold higher dose of niacin given once a day.

ARI-001 given once daily for 28 days produced a greater change in plasma lipid levels compared with the same dose of ARI-001 given once daily for 18 days.

ARI-001 given once daily produced highly significant changes in plasma lipids, greater than or equal to the lipid altering effects observed with the same total dose of ARI-001 given twice daily. Additionally, once daily ARI-001 was more potent than niacin in effecting desirable lipid changes.

Changes in plasma levels of TC, HDL-C, TG, LDL-C and FFA correlated with plasma concentrations of ARI-001 present in plasma Plasma and liver concentrations of ARI-001 are proportionately related.

Liver concentration of ARI-001 correlated with decreases in plasma TC, LDL-C, TG and FFA and increases in plasma HDL-C.

ARI-001 showed no evidence of capillary vasodilation or hyperemia (a proxy of flush) in experiments using Doppler capillary blood flow measurements in mice. Additionally, clinical symptoms of "flushing" were not observed over 28 days in rats or dogs.

Example 8

Human Clinical Trial with ARI-001

A randomized, double-blind, placebo-controlled study is performed with sequential escalating doses by cohort with observations for 30 hours post dosing and return visit on 8th day. Study subjects are healthy male and female adult volunteers, age 18-60 years, with LDL-C>130 mg/dL and weight <85 kg. Subjects are randomly assigned to receive study drug or placebo.

Five periods of single dose escalation, with 8 subjects per cohort (6 drug: 2 placebo) involve a total 40 subjects. Appropriately blinded matching placebos are provided. Cohort 1 receives 500 mg of ARI-001 formulated as a single oral tablet, plus eleven placebo tablets; Cohort 2, 1000 mg taken as two 500 mg tablets of ARI-001, plus ten placebo tablets; Cohort 3, 2000 mg taken as four 500 mg tablets of ARI-001, plus eight placebo tablets; Cohort 4, 4000 mg taken as eight 500 mg tablets of ARI-001, plus four placebo tablets; Corhort 5, 6000 mg taken as twelve 500 mg tablets of ARI-001. Placebo-only subjects take twelve placebo tablets. Each tablet is a compressed, film-coated tablet suitable for oral administration.

Primary objectives of the study are to evaluate the safety and tolerability of single doses of ARI-001 in healthy adult volunteers, at doses ranging from 500 mg to 6000 mg.

Secondary objectives of the study are to establish the pharmacokinetic profile of ARI-001 in blood after a single dose in healthy volunteers; observe changes in fasting triglycerides, free fatty acid and other lipid biomarkers; correlate the dose level and plasma drug exposures over time with any changes in fasting triglycerides, free fatty acid and other lipid biomarkers; and establish the effect of ARI-001 on symptoms of flushing by visual analog score (VAS).

Pharmacokinetic samples are collected at 0-45 min pre-dose and at 0.5, 1, 1.5, 2, 4, 6, 8, 12, 24, 30 and 168 hours after dosing. The actual time of each plasma collection is recorded.

At each collection, 3 mL of blood is collected into a Vacutainer tube containing EDTA (purple top) and refrigerated immediately. Within 30 minutes of collection, the plasma fraction is separated by centrifugation at 2,000 rpm for 15 minutes at 4° C. Analysis of all samples is performed at a central laboratory.

On Day 1, pre-dose, the following procedures are performed:

Clinical laboratory tests including liver function (ALT, AST, serum bilirubin), CK, hematology, APTT, PT, urinalysis and lipid chemistry panel (LDL-C, HDL-C, free fatty acids, triglycerides, LPA and ApoA-1)

12-lead ECG

Vital signs

VAS

Baseline plasma PK

Urine collection for baseline PK between midnight and 0 hours (dosing)

After study drug administration, the following procedures are performed.

Clinical laboratory tests including liver function (ALT, AST, serum bilirubin), CK, hematology and APTT, PT at 6, 12 and 24 hours post-dose Lipid chemistry panel (LDL-C, HDL-C, free fatty acids, triglycerides, Lp(a) and ApoA-1) at 4, 12 and 24 hours post-dose 12-lead ECG at 1, 2, 4, 6, 8, 12 and 24 hours post-dose Urinalysis at 24 hours post-dose Vital signs at 6, 12, 24 and 30 hours post-dose VAS at 0.25, 0.5, 1, 2, 4, 8, 12 and 24 hours post-dose Physical examination at 24 hours post-dose and a brief clinical examination at 30 hours post-dose Collect blood sample for PK at 0.5, 1, 1.5, 2, 4, 6, 8, 12, 24 and 30 hours posts-dose Collect blood sample for troponin at 4 hours post-dose Collect urine for PK in 6 hour intervals at 0 to 6, 6 to 12, 12 to 18, 18 to 24, and 24 to 30 hours after dosing.

Preliminary results from this human clinical trial include the remarkable observation that no patients exhibited any signs of flushing at any dose of ARI-001, up to and including the 6000 mg dose.

Figure 22:
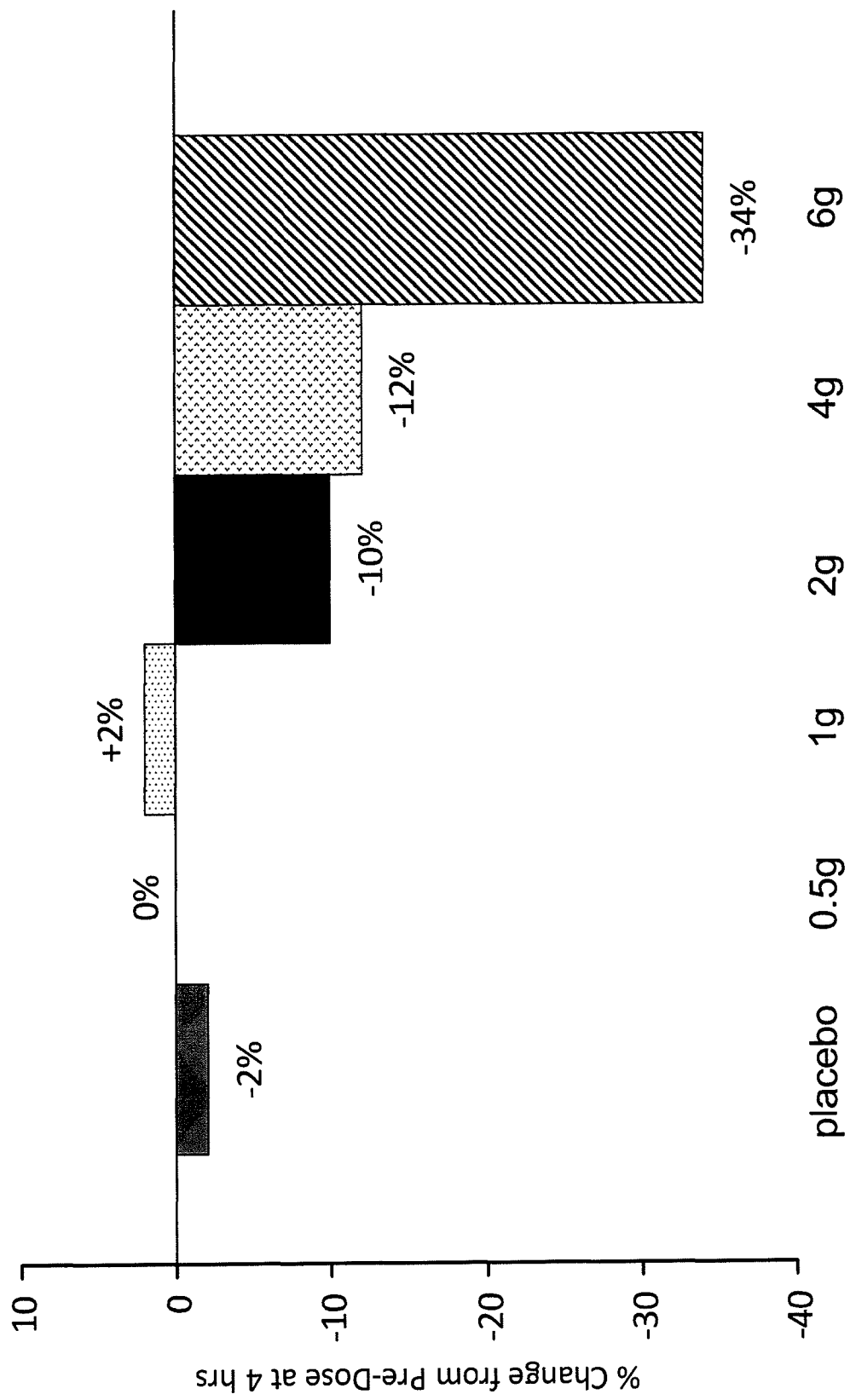
FIG. 22. Dose response for triglyceride lowering on single oral doses of ARI-001 to human patients. The percent change is the mean percent change in triglycerides at 4 hours post dose.

Additional preliminary results are shown in FIG. 22, which illustrates dose response for triglyceride lowering in humans on single oral doses of ARI-001 as measured 4 hours after dosing.

Figure 23:
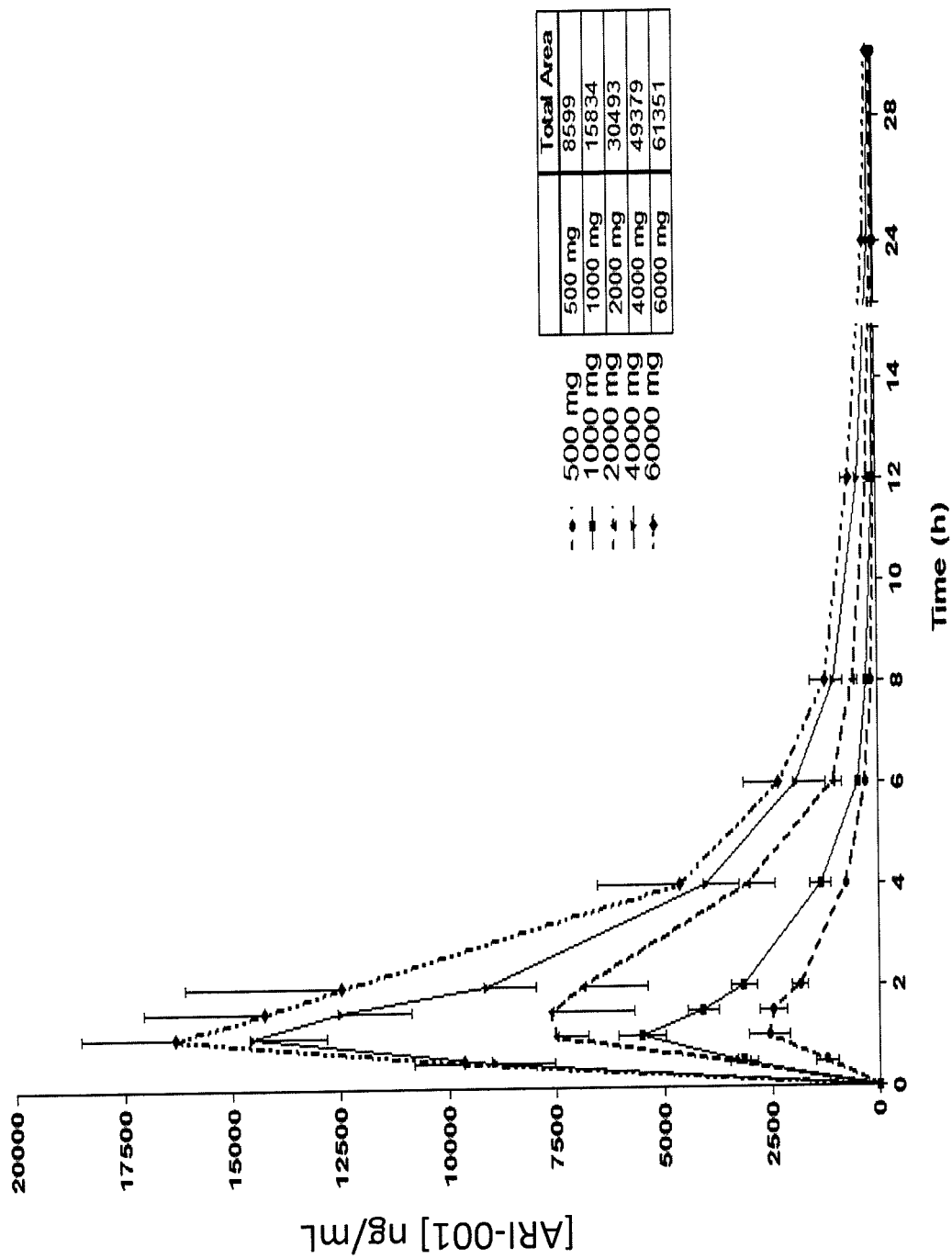
FIG. 23. Serum concentration of ARI-001 over time following single oral administration of indicated amounts of ARI-001 to human patients.

Further preliminary results are shown in FIG. 23, which illustrates serum concentration of ARI-001 as measured over 24 hours in humans following single oral doses, ranging from 500 mg to 6000 mg, of ARI-001. $C_{max}$ for the 2000 mg dose of ARI-001 was about 7500 ng/mL (7.5 mg/mL); $C_{max}$ for 1500 mg of niacin (roughly equimolar dose) was about 30,000 ng/mL (30 mg/mL).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

We claim:

1. A method of reducing a serum or plasma level of at least one lipid selected from the group consisting of total cholesterol, low-density lipoprotein (LDL) cholesterol, triglycerides, and lipoprotein (a), comprising orally administering to a human in need thereof an effective amount of a niacin analog or a pharmaceutically acceptable salt thereof, wherein said oral administration is characterized by reduced flushing and reduced hepatocellular damage, as compared to oral administration of an equimolar dose of immediate-release niacin, wherein the niacin analog is represented by structure I:

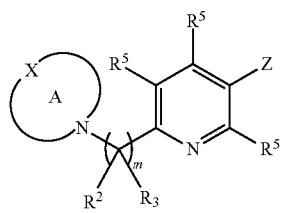

wherein

A is a heterocyclyl or heteroaryl, optionally deuterated, containing from 5 to 12 ring atoms, including X and N, which is optionally substituted with 1-3 substituents, independently selected from the group consisting of alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;

X is O, S, N or N($R^6$);

Z is

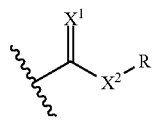

or an isostere of a carboxyl group;

$X^1$ is O or S;

$X^2$ is O or S;

R is hydrogen, alkyl, haloalkyl, alkenyl, alkynyl, carbocyclyl, heterocyclyl, heterocyclylalkyl, aryl, aralkyl, heteroaryl, heteroaralkyl, fused bicyclyl, carboxyalkyl, or arylalkenylaryl;

$R^2$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;

$R^3$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;

$R^5$ is selected independently for each occurrence from the group consisting of hydrogen, alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;

$R^6$ is hydrogen or lower alkyl;

m is 1, 2, 3, or 4; and peak concentration ($C_{max}$) for the niacin analog is 40 percent or less of $C_{max}$ for the equimolar oral dose of immediate-release niacin.

2. The method of claim 1, wherein the ratio of peak concentration to area under the curve at 24 hours ($C_{max}/AUC_{0-24}$) for the niacin analog is 0.35 $h^{-1}$ or less.

3. The method of claim 1, wherein the time to peak concentration ($t_{max}$) for the niacin analog is in the range of 1 to 5 hours.

4. The method of claim 1, wherein the niacin analog has an $EC_{50}$ for β-arrestin-mediated GPR109A function which is at least 10 times greater than the $EC_{50}$ of niacin for β-arrestin-mediated GPR109A function.

5. The method of claim 1, wherein the niacin analog when administered orally to a human also increases a serum or plasma level of high-density lipoprotein (HDL) cholesterol.

6. The method of claim 1, wherein said oral administration is characterized by substantially no increase in serum levels of aspartate aminotransferase (AST), alanine aminotransferase (ALT), or both.

7. The method of claim 1, further comprising administering to the human a statin.

8. The method of claim 7, wherein the statin is selected from the group consisting of atorvastatin, cerivastatin, fluvastatin, lovastatin, mevastatin, pitavastatin, pravastatin, rosuvastatin and simvastatin.

9. A method of reducing a serum or plasma level of at least one lipid selected from the group consisting of total cholesterol, low-density lipoprotein (LDL) cholesterol, triglycerides, and lipoprotein (a), comprising orally administering to a human in need thereof an effective amount of a niacin analog or a pharmaceutically acceptable salt thereof, wherein said oral administration is characterized by reduced flushing and reduced hepatocellular damage, as compared to oral administration of an equimolar dose of immediate-release niacin, wherein the niacin analog is represented by structure I:

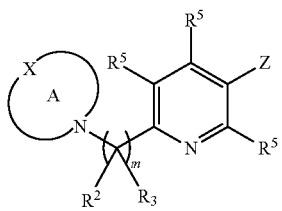

wherein
A is a heterocyclyl or heteroaryl, optionally deuterated, containing from 5 to 12 ring atoms, including X and N, which is optionally substituted with 1-3 substituents, independently selected from the group consisting of alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;
X is O, S, N or N(R$^6$);
Z is

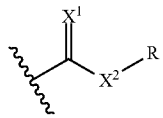

or an isostere of a carboxyl group;
X$^1$ is O or S;
X$^2$ is O or S;
R is hydrogen, alkyl, haloalkyl, alkenyl, alkynyl, carbocyclyl, heterocyclyl, heterocyclylalkyl, aryl, aralkyl, heteroaryl, heteroaralkyl, fused bicyclyl, carboxyalkyl, or arylalkenylaryl;
R$^2$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;
R$^3$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;
R$^5$ is selected independently for each occurrence from the group consisting of hydrogen, alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;
R$^6$ is hydrogen or lower alkyl;
m is 1, 2, 3, or 4; and
the ratio of peak concentration to area under the curve at 24 hours ($C_{max}/AUC_{0-24}$) for the niacin analog is 0.35 h$^{-1}$ or less.

10. The method of claim 9, wherein the time to peak concentration ($t_{max}$) for the niacin analog is in the range of 1 to 5 hours.

11. The method of claim 9, wherein the niacin analog has an EC$_{50}$ for β-arrestin-mediated GPR109A function which is at least 10 times greater than the EC$_{50}$ of niacin for β-arrestin-mediated GPR109A function.

12. The method of claim 9, wherein the niacin analog when administered orally to a human also increases a serum or plasma level of high-density lipoprotein (HDL) cholesterol.

13. The method of claim 9, wherein said oral administration is characterized by substantially no increase in serum levels of aspartate aminotransferase (AST), alanine aminotransferase (ALT), or both.

14. The method of claim 9, further comprising administering to the human a statin.

15. The method of claim 14, wherein the statin is selected from the group consisting of atorvastatin, cerivastatin, fluvastatin, lovastatin, mevastatin, pitavastatin, pravastatin, rosuvastatin and simvastatin.

16. A method of reducing a serum or plasma level of at least one lipid selected from the group consisting of total cholesterol, low-density lipoprotein (LDL) cholesterol, triglycerides, and lipoprotein (a), comprising orally administering to a human in need thereof an effective amount of a niacin analog or a pharmaceutically acceptable salt thereof, wherein said oral administration is characterized by reduced flushing and reduced hepatocellular damage, as compared to oral administration of an equimolar dose of immediate-release niacin, wherein the niacin analog is represented by structure I:

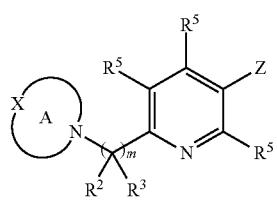

wherein
A is a heterocyclyl or heteroaryl, optionally deuterated, containing from 5 to 12 ring atoms, including X and N, which is optionally substituted with 1-3 substituents, independently selected from the group consisting of alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;

X is O, S, N or N($R^6$);

Z is

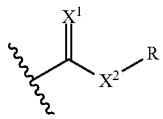

or an isostere of a carboxyl group;

$X^1$ is O or S;

$X^2$ is O or S;

R is hydrogen, alkyl, haloalkyl, alkenyl, alkynyl, carbocyclyl, heterocyclyl, heterocyclylalkyl, aryl, aralkyl, heteroaryl, heteroaralkyl, fused bicyclyl, carboxyalkyl, or arylalkenylaryl;

$R^2$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;

$R^3$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;

$R^5$ is selected independently for each occurrence from the group consisting of hydrogen, alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;

$R^6$ is hydrogen or lower alkyl;

m is 1, 2, 3, or 4; and the time to peak concentration ($t_{max}$) for the niacin analog is in the range of 1 to 5 hours.

17. The method of claim 16, wherein the niacin analog has an $EC_{50}$ for β-arrestin-mediated GPR109A function which is at least 10 times greater than the $EC_{50}$ of niacin for β-arrestin-mediated GPR109A function.

18. The method of claim 16, wherein the niacin analog when administered orally to a human also increases a serum or plasma level of high-density lipoprotein (HDL) cholesterol.

19. The method of claim 16, wherein said oral administration is characterized by substantially no increase in serum levels of aspartate aminotransferase (AST), alanine aminotransferase (ALT), or both.

20. The method of claim 16, further comprising administering to the human a statin.

21. The method of claim 20, wherein the statin is selected from the group consisting of atorvastatin, cerivastatin, fluvastatin, lovastatin, mevastatin, pitavastatin, pravastatin, rosuvastatin and simvastatin.

22. A method of reducing a serum or plasma level of at least one lipid selected from the group consisting of total cholesterol, low-density lipoprotein (LDL) cholesterol, triglycerides, and lipoprotein (a), comprising orally administering to a human in need thereof an effective amount of a niacin analog or a pharmaceutically acceptable salt thereof, wherein said oral administration is characterized by reduced flushing and reduced hepatocellular damage, as compared to oral administration of an equimolar dose of immediate-release niacin, wherein the niacin analog is represented by structure I:

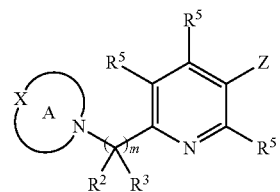

wherein

A is a heterocyclyl or heteroaryl, optionally deuterated, containing from 5 to 12 ring atoms, including X and N, which is optionally substituted with 1-3 substituents, independently selected from the group consisting of alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;

X is O, S, N or N($R^6$);
Z is

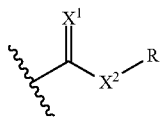

or an isostere of a carboxyl group;

$X^1$ is O or S;
$X^2$ is O or S;
R is hydrogen, alkyl, haloalkyl, alkenyl, alkynyl, carbocyclyl, heterocyclyl, heterocyclylalkyl, aryl, aralkyl, heteroaryl, heteroaralkyl, fused bicyclyl, carboxyalkyl, or arylalkenylaryl;
$R^2$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;
$R^3$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;
$R^5$ is selected independently for each occurrence from the group consisting of hydrogen, alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;
$R^6$ is hydrogen or lower alkyl;
m is 1, 2, 3, or 4; and
the niacin analog has an $EC_{50}$ for β-arrestin-mediated GPR109A function which is at least 10 times greater than the $EC_{50}$ of niacin for β-arrestin-mediated GPR109A function.

23. The method of claim 22, wherein the niacin analog when administered orally to a human also increases a serum or plasma level of high-density lipoprotein (HDL) cholesterol.

24. The method of claim 22, wherein said oral administration is characterized by substantially no increase in serum levels of aspartate aminotransferase (AST), alanine aminotransferase (ALT), or both.

25. The method of claim 22, further comprising administering to the human a statin.

26. The method of claim 25, wherein the statin is selected from the group consisting of atorvastatin, cerivastatin, fluvastatin, lovastatin, mevastatin, pitavastatin, pravastatin, rosuvastatin and simvastatin.

27. A method of reducing a serum or plasma level of at least one lipid selected from the group consisting of total cholesterol, low-density lipoprotein (LDL) cholesterol, triglycerides, and lipoprotein (a), comprising orally administering to a human in need thereof an effective amount of a niacin analog or a pharmaceutically acceptable salt thereof, wherein said oral administration is characterized by reduced flushing and reduced hepatocellular damage, as compared to oral administration of an equimolar dose of immediate-release niacin, wherein the niacin analog is represented by structure I:

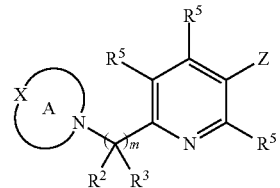

wherein
A is a heterocyclyl or heteroaryl, optionally deuterated, containing from 5 to 12 ring atoms, including X and N, which is optionally substituted with 1-3 substituents, independently selected from the group consisting of alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;

X is O, S, N or N($R^6$);
Z is

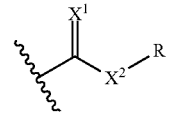

or an isostere of a carboxyl group;
$X^1$ is O or S;
$X^2$ is O or S;
R is hydrogen, alkyl, haloalkyl, alkenyl, alkynyl, carbocyclyl, heterocyclyl, heterocyclylalkyl, aryl, aralkyl, heteroaryl, heteroaralkyl, fused bicyclyl, carboxyalkyl, or arylalkenylaryl;
$R^2$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;
$R^3$ is hydrogen, lower alkyl, lower alkenyl, lower alkynyl, halogen, hydroxyl, amine, carboxyl, cycloalkyl, aryl, heteroaryl, aralkyl, heteroaralkyl, cyano, or nitro;
$R^5$ is selected independently for each occurrence from the group consisting of hydrogen, alkyl, alkenyl, alkynyl, aryl, heteroaryl, aralkyl, heteroaralkyl, halogen, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amine, alkylamine, arylamine, heteroarylamine, aralkylamine, heteroaralkylamine, alkenylamine, alkynylamine, formylamine, acylamine, carboxyl, alkyloxycarbonyl, aryloxycarbonyl, heteroaryloxycarbonyl, aralkyloxycarbonyl, heteroaralkyloxycarbonyl, amido, alkylaminecarbonyl, arylaminecarbonyl, heteroarylaminecarbonyl, aralkylaminecarbonyl, and heteroaralkylaminecarbonyl;

$R^6$ is hydrogen or lower alkyl;

m is 1, 2, 3, or 4; and said oral administration is characterized by substantially no increase in serum levels of aspartate aminotransferase (AST), alanine aminotransferase (ALT), or both.

28. The method of claim 27, further comprising administering to the human a statin.

29. The method of claim 28, wherein the statin is selected from the group consisting of atorvastatin, cerivastatin, fluvastatin, lovastatin, mevastatin, pitavastatin, pravastatin, rosuvastatin and simvastatin.

* * * * *